United States Patent
Verkman et al.

(10) Patent No.: US 8,129,365 B2
(45) Date of Patent: Mar. 6, 2012

(54) WATER-SOLUBLE, FLUORESCENT COMPOUNDS FOR DETECTION OF POTASSIUM IONS

(75) Inventors: Alan Verkman, San Francisco, CA (US); Prashant A. Padmawar, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 836 days.

(21) Appl. No.: 12/088,929

(22) PCT Filed: Oct. 11, 2006

(86) PCT No.: PCT/US2006/039973
§ 371 (c)(1),
(2), (4) Date: Jul. 23, 2008

(87) PCT Pub. No.: WO2007/044866
PCT Pub. Date: Apr. 19, 2007

(65) Prior Publication Data
US 2008/0311041 A1    Dec. 18, 2008

Related U.S. Application Data

(60) Provisional application No. 60/725,725, filed on Oct. 11, 2005.

(51) Int. Cl.
*A61K 31/33* (2006.01)
*C07D 491/02* (2006.01)
(52) U.S. Cl. ........................ 514/183; 540/469
(58) Field of Classification Search .................. None
See application file for complete search history.

(56) References Cited

U.S. PATENT DOCUMENTS

| | | | |
|---|---|---|---|
| 4,945,171 | A | 7/1990 | Haugland et al. |
| 5,162,525 | A | 11/1992 | Masilamani et al. |
| 5,220,012 | A | 6/1993 | Mathis et al. |
| 5,227,487 | A | 7/1993 | Haugland et al. |
| 5,439,828 | A | 8/1995 | Masilamani et al. |
| 5,457,185 | A | 10/1995 | Lehn et al. |
| 5,948,906 | A | 9/1999 | Tsien et al. |
| 6,001,999 | A | 12/1999 | Wolfbeis et al. |
| 6,211,359 | B1 | 4/2001 | He et al. |
| 6,399,392 | B1 | 6/2002 | Haugland et al. |
| 2004/0180391 | A1 | 9/2004 | Gratzl et al. |

FOREIGN PATENT DOCUMENTS
EP    1081152    3/2001

OTHER PUBLICATIONS

Carpenter. European Journal of Organic Chemistry, 2011, 7, 1242-48.*
Lehn et al., J. Amer. Chem. Soc. 97, 6700-6207 (1975).
Somjen et al., J. Neurophysiol. 53, 1098-1108 (1985).
Milito et al., J. Cereb. Blood Flow Metab. 8, 155-162 (1988).
Bryan et al., Biosensors 4:169-179 (1989).
Lohr et al., Acc. Chem. Res. 18:65-72 (1985).
Minta et al., J. Biol. Chem. 264, 9449-19457 (1989).
Stringer et al., Epilepsy Res. 4, 177-186 (1989).
de Silva et al., Tetrahedron Lett. 31:5193-5196 (1990).
Izatt et. al., Chem Rev. 85, 271-339 (1985).
Nicholson, J. Neurosci. Methods 48, 199-213 (1993).
de Silva, A.P. et al., Chem. Rev. 97, 1515-1566 (1997).
Ma et al., J. Clin. Invest. 100, 957-962 (1997).
Nagelhus et al., Glia 26, 47-54 (1999).
Sick et al., Stroke 30, 2416-2422 (1999).
Kager et al., J. Neurophysiol. 84, 495-512 (2000).
Manley et al., Nat Med. 6, 159-163 (2000).
Li et al., J. Biol. Chem. 276, 31233-31237 (2001).
Bolay et al., Nat. Med. 8, 136-142 (2002).
Amiry-Moghaddam et al., Proc. Natl. Acad. Sci. USA 100, 13615-13620 (2003).
He, et al., J. Am. Chem. Soc. 125, 1468-1469 (2003).
Binder et al., Neuroreport 15:259-262 (2004).
Binder et al., J. Neurosci. 24:8049-8056 (2004).
Connors et al., J. Biol. Chem. 279, 28387-28392 (2004).
Gursoy-Ozdemir et al., J Clin. Invest. 113, 1447-1455 (2004).
Papadopoulos et al., FASEB Journal 18, 1291-1293 (2004).
Eid, T. et al., Proc. Natl. Acad. Sci. USA 102, 1193-1198 (2005).
International Search Report (ISR), Jun. 3, 2007.
Written Opinion of the International Searching Authority, Jun. 3, 2007.
International Preliminary Report on Patentability, Chapter I (IPRP), Apr. 16, 2008.

* cited by examiner

*Primary Examiner* — Noble Jarrell
(74) *Attorney, Agent, or Firm* — Carol L. Francis; Bozicevic, Field & Francis LLP

(57) ABSTRACT

The invention provides chromoionophore compounds comprising a triazacryptand (TAC) K$^+$ ionophore conjugated to at least a first chromophoric moiety (e.g., xanthylium dyes and derivatives thereof). In related embodiments, the chromoionophore compounds further comprise a second chromophoric moiety which is insensitive to potassium binding by the TAC ionophore, thus providing for dual wavelength detection and absolute determination of K$^+$ concentration. The invention further provides methods and kits for the determination of K$^+$ concentrations in biological systems, either in vitro or in vivo, using embodiments of inventive chromoionophores.

54 Claims, 21 Drawing Sheets f

Alexa fluor 610

WATER-SOLUBLE, FLUORESCENT COMPOUNDS FOR DETECTION OF POTASSIUM IONS

CROSS-REFERENCE TO RELATED APPLICATION

This application claims priority benefit to U.S. provisional application Ser. No. 60/725,725, filed Oct. 11, 2005, which application is incorporated herein by reference.

STATEMENT REGARDING FEDERALLY SPONSORED RESEARCH

This invention was made with government support under grant number R01 EB00415, awarded by the National Institutes of Health. The government has certain rights in this invention.

BACKGROUND OF THE INVENTION

The measurement of potassium ion ($K^+$) levels in biological samples, either in vivo or in vitro, is of great interest, particularly given the impact ion levels have on many aspects of homeostasis. For example, regulation of $K^+$ in cellular and extracellular compartments is of central importance in volume homeostasis, fluid transport and neuromuscular signaling. Rapid changes in extracellular space (ECS) $K^+$ concentration ($[K^+]_o$) occur in the central nervous system during neural activity, with abnormally sustained and spatially-propagating elevations in $[K+]_o$ seen in seizures and spreading depression (Somjen et al. *J. Neurophysiol.* 53, 1098-1108 (1985); Kager et al. *J. Neurophysiol.* 84, 495-512 (2000)). Assessment of $K^+$ concentration is particularly challenging in these contexts, both by virtue of being an in vivo measurement, as well as requiring both spatial and temporal real-time $K^+$ concentration determination.

$K^+$-sensitive, double-barreled microelectrodes have been the gold standard for in situ biological $K^+$ measurements (Nicholson *J. Neurosci. Methods* 48, 199-213 (1993); Sick et al. *Stroke* 30, 2416-2422 (1999). Although accurate measurement of $K^+$ concentration is possible using microelectrodes, their fabrication is technically challenging and their use involves direct invasion of a single measurement site. A $K^+$-sensing fluorescent dye has been developed for cytoplasmic $K^+$ (Minta et al. *J. Biol. Chem.* 264, 9449-19457 (1989)), though few applications have been reported because of its low fluorescence and poor $K^+$-to-$Na^+$ selectively.

Chromoionophores, and particularly fluoroionophores have gained great interest in use in detection of ion concentrations. Exemplary of such compounds are those having an ionophore portion, which binds an ion of interest, and a fluorophore portion, which provides a fluorescent signal in response to the ion-binding event. Cryptands are one type of ionophore that has been used to create families of chromoionophores (see, e.g., U.S. Pat. No. 6,211,359). These crown ether ionophores form complexes with cations whose ion radius corresponds to that of the cavity formed by the cryptand (Lehn et al. *J. Amer. Chem. Soc.,* 97:6700-6207 (1975)). Ionic radii of the alkali metals Li, Na, K and Rb are 0.78, 0.98, 1.33 and 1.49 Å, respectively (Izatt et. al *Chem Rev* 1985, 85, 271-339). It is possible to tailor the ether chains of the crown ether or cryptand to target particular cation.

The chemical attributes required for a chromoionophore for a biological application, such as imaging of $K^+$ concentrations in the ECS of the brain, for example, include bright long-wavelength fluorescence, high $K^+$ sensitivity in the physiological concentration range (e.g., up to about 150 mM, with concentrations of about 40 mM in the brain and 120 mM in the extracellular space of other tissues such as airways/lung), pH insensitivity, rapid response, water solubility, and a high $K^+$-to-$Na^+$ selectivity. Additionally, for in vivo imaging of an ECS, the chromoionophore must be membrane impermeable and non-toxic. To date, and to the best of the inventors' knowledge, none of the known chromoionophores using cryptands possess the attributes required for a biological application, such as medical imaging.

For instance, de Silva et al. (*Tetrahedron Lett.* 1990, 31, 5193-5196) used diazacryptands having aniline-type nitrogens in the crown ether ring for potassium binding. These diazacryptands suffered from sodium interference while determination of potassium ions in the physiological concentration range.

Masilamani et al (U.S. Pat. Nos. 5,439,828, and 5,162,525) describe the utility of diazacryptand functionalized with fluorescent coumarins. These diazacryptand fluoroionophores showed selective for lithium, sodium and potassium ions depending on their molecular structure. The disadvantage of these compounds included a high pH sensitivity and an excitation wavelength at about 330 nm, which is significantly lower than the targeted excitation wavelength of about 500 nm or greater.

He et al (U.S. Pat. No. 6,211,359; see also He et al. *J. Am. Chem. Soc.* 125:1468-1469 (2003)) showed use of triazacryptand as an ionophore for potassium measurement covalently linked via an alkyl spacer to a napthilimide chromophore, which in turn was conjugated to cellulose. These compounds of He et al. are water insoluble, and the conjugated compounds bound to cellulose exhibited relatively low $K^+$-to-$Na^+$ selectivity.

There is a great need for development of alternative methods to measure $K^+$ concentration in biological samples under physiological conditions. In particular there is a need for methods to measure $K^+$ concentration in living systems, particularly in the brain ECS, which is the small contiguous space between brain cells where rapid changes in $[K^+]_o$ occur in normal neural activity and in diseases such as epilepsy. Specifically, there is a need for a $K^+$-sensing compound that provides a long wavelength fluorescent signal, is water soluble, membrane impermeant, and is highly potassium selective, insensitive to sodium concentrations and other biologically-relevant cations or anions, and insensitive to pH in the physiological range. Further, such a $K^+$-sensing fluorescent dye should be non-toxic and suitable for use in vivo for a variety of measurements, such as detection of propagating $K^+$ waves in the brain ECS. The present invention addresses these needs.

LITERATURE

Lehn et al. *J. Amer. Chem. Soc.* 97, 6700-6207 (1975); Somjen et al. *J. Neurophysiol.* 53, 1098-1108 (1985); Milito et al. *J. Cereb. Blood Flow Metab.* 8, 155-162 (1988); Bryan et al. Biosensors 4:169-179 (1989); Lohr et al. *Acc. Chem. Res.* 18:65-72 (1985); Minta et al. *J. Biol. Chem.* 264, 9449-19457 (1989); Stringer et al. *Epilepsy Res.* 4, 177-186 (1989); de Silva et al. *Tetrahedron Lett.* 31:5193-5196 (1990); Izatt et. al. *Chem Rev* 1985, 85, 271-339 Nicholson *J. Neurosci. Methods* 48, 199-213 (1993); de Silva, A. P. et al. *Chem. Rev.* 97, 1515-1566 (1997); Ma, et al. *J. Clin. Invest.* 100, 957-962 (1997); Nagelhus et al. *Glia* 26, 47-54 (1999); Sick et al. *Stroke* 30, 2416-2422 (1999); Kager et al. *J. Neurophysiol.* 84, 495-512 (2000); Manley et al. *Nat Med.* 6, 159-163 (2000); Li et al. *J. Biol. Chem.* 276, 31233-31237 (2001);

Bolay et al. *Nat. Med.* 8, 136-142 (2002); Amiry-Moghaddam et al. *Proc. Natl. Acad. Sci. USA* 100, 13615-13620 (2003); He, et al. *J. Am. Chem. Soc.* 125, 1468-1469 (2003); Binder et al. *Neuroreport* 15:259-262 (2004); Binder et al. J. Neurosci. 24:8049-8056 (2004); Connors et al. *J. Biol. Chem.* 279, 28387-28392 (2004); Gursoy-Ozdemir et al. *J Clin. Invest.* 113, 1447-1455 (2004); Papadopoulos et al. *FASEB Journal* 18, 1291-1293 (2004); Eid, T. et al. Proc. Natl. Acad. Sci. USA 102, 1193-1198 (2005);

U.S. Pat. Nos. 4,9455,171; 5,220,012; 5,227,487; 5,439, 828; 5,162,525; 5,457,185; 5,948,906; 6,211,359; 6,001,999; 6,211,359 and 6,399,392. EP1081152.

SUMMARY OF THE INVENTION

The invention provides chromoionophore compounds comprising a triazacryptand (TAC) K+ ionophore conjugated to at least a first chromophoric moiety (e.g., xanthylium dyes and derivatives thereof). In related embodiments, the chromoionophore compounds further comprise a second chromophoric moiety which is insensitive to potassium binding by the TAC ionophore, thus providing for dual wavelength detection and absolute determination of K+ concentration. The invention further provides methods and kits for the determination of K+ concentrations in biological systems, either in vitro or in vivo, using embodiments of the inventive chromoionophores.

In one aspect the invention features a potassium-sensitive chromoionophore comprising the formula below, as well as pharmaceutically acceptable salts thereof:

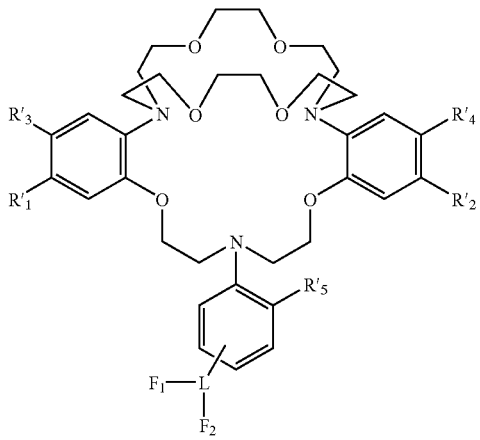

wherein $F_1$ and $F_2$ each represent a chromophoric moiety, where $F_2$ may be present or absent;

$R'_1$ and $R'_2$ are lower alkyls and $R'_3$ and $R'_4$ independently selected from H or a lower alkyl; or, when $F_2$ is absent, $R'_1$ and $R'_2$ are independently selected from a lower alkyl or $F_3$, and $R'_3$ and $R'_4$ are independently H or lower alkyls; or when $F_2$ is absent, $R'_1$ and $R'_2$ are lower alkyls, and $R'_3$ and $R'_4$ are independently selected from a lower alkyl or $F_3$, wherein $F_3$ is of the formula

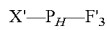

where X' is a reactive group, such as amine, succinimidyl ester, or aldehyde, wherein an X' of particular interest is

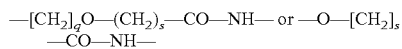

where q is an integer from 1 to 2; s is an integer from 2 to 6; $P_H$ is selected from a hydrophilic, water-soluble polymer; and $F'_3$ is a chromophoric moiety insensitive to pH and to potassium binding by the chromoionophore, where $F'_3$ provides a detectable signal that is different from a detectable signal of $F_1$;

$R'_5$ is a substituted or unsubstituted alkyl (e.g. lower alkyl), alkoxy (e.g. lower alkoxy), alkoxyalkoxy, alkoxyaryl, t-alkylester (e.g. t-butyl ester of carboxyloweralkoxy, t-alkylester of carboxyalkoxyalkoxy, succinimidylester of carboxyalkoxy, succinimidylester of carboxyalkoxyalkoxy, aminoalkoxy, aminoalkoxyalkoxy, mercaptoalkoxy, or mercaptoalkoxyalkoxy;

L is a linker selected from a substituted or unsubstituted lower alkyl of the formula —$(CH_2)_v$— or —$(CH_2)_w$—NH—, where v is 0, 1, or 2 and w is 1 or 2; a substituted phenyl group; or a bifunctional group; and $F_1$ is a chromophoric moiety which provides a detectable fluorescent signal upon excitation when potassium is bound to the ionophore, wherein when $F_2$ and $F_3$ are absent, $F_1$ is comprises the formula:

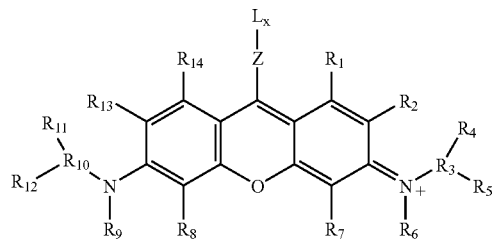

where $L_x$ indicates binding to the linker L;

$R_1$ and $R_{14}$ are each independently selected from H or a lower alkyl;

$R_2$ and $R_{13}$ are each independently selected from H or a lower alkyl unless:

$R_2$ and $R_{13}$ are joined to form a quinolizine ring system that includes $R_3$, $R_6$, and $R_7$, and $R_8$, $R_9$, and $R_{10}$, respectively, to provide one or two quinolizine ring systems in the compound; or $R_2$ and $R_{13}$ are joined to form in the compound pyridine or thieno-pyridine ring systems that include $R_3$ and $R_{10}$, respectively, to provide one or two pyridine ring systems or one or two thieno-pyridine ring systems in the compound, and wherein the thieno-pyridine ring systems are thieno-quinoline ring systems;

wherein when $R_2$ and $R_{13}$ are present in ring structures, at least one of the ring structures contains a positively charged amine, and when $R_2$ and $R_{13}$ are joined to form pyridine ring systems that include $R_3$ and $R_{10}$ respectively the pyridine ring systems are substituted by a methylene or polymethylene group that is substituted by an anionic moiety, e.g. —$CH_2SO_3^-$;

$R_4$, $R_5$, $R_{11}$, and $R_{12}$ are independently selected from H or a lower alkyl, and are present when $R_2$ and $R_{13}$ are joined in ring structures with $R_3$ and $R_{10}$, respectively, otherwise $R_4$, $R_5$ $R_{11}$, and $R_{12}$ are absent;

$R_3$, $R_6$, $R_9$, and $R_{10}$ are independently selected from a lower alkyl if "N" is not part of a ring structure; and $R_7$ and $R_9$ are independently selected from H or a lower alkyl if $R_7$ and $R_8$ are not part of a ring structure with $R_6$ and $R_9$, respectively;

Z is of the formula:

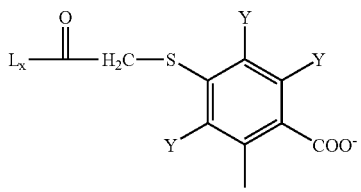

wherein Y are each independently halides, and $L_x$ indicates binding to the linker L, and Z is present when $R_2$ and $R_{13}$ are joined to form pyridine ring systems that include $R_3$ and $R_{10}$, respectively; and $F_2$, when present, is of the formula $X-P_H-F_2'$, where X is an alkyl benzamide, succinimidyl ester, or aldehyde;

$P_H$ is a hydrophilic, water-soluble polymer, and $F'_2$ is a chromophoric moiety that provides a stable detectable signal insensitive to potassium binding and pH, where $F'_2$ provides a detectable signal distinguishable from the detectable signal of $F'_1$.

In related embodiments, $R'_5$ of the chromoionophore is of the formula:

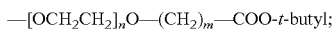

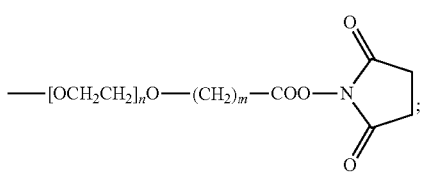

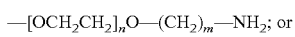

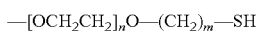

n is 0 or 1, and m is an integer from 1 to 6.

In further related embodiments, $P_H$ of the chromoionophore is dextran, polyethylene oxide, polyethyleneimine (PEI), polylactide, polyglycolide, or polylactide glycolide acid (PLGA).

In still further related embodiments, where $F_2$ of the formula above is absent, $R'_1$ and $R'_2$ are lower alkyls, $R'_3$ and $R'_4$ are independently H or a lower alkyl, and $F_1$ comprises the formula:

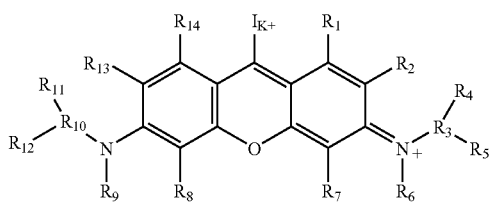

where:

$R_1$ and $R_{14}$ are each independently selected from H or a lower alkyl;

$R_2$ and $R_{13}$ are each independently selected from H or a lower alkyl unless:

$R_2$ and $R_{13}$ are joined to form quinolizine ring systems that include $R_3$, $R_6$, and $R_7$, and $R_8$, $R_9$, and $R_{10}$, respectively, to provide one or two quinolizine ring systems in the compound; or $R_2$ and $R_{13}$ are joined to form in the compound pyridine or thieno-pyridine ring systems that include $R_3$ and $R_{10}$, respectively, to provide one or two pyridine ring systems or one or two thieno-pyridine ring systems in the compound, and wherein the thieno-pyridine ring systems are thieno-quinoline ring systems;

wherein when $R_2$ and $R_{13}$ are present in ring structures, at least one of the ring structures contains a positively charged amine, and when $R_2$ and $R_{13}$ are joined to form pyridine ring systems that include $R_3$ and $R_{10}$, respectively, the pyridine ring systems are substituted by a methylene or polymethylene group that is substituted by an anionic moiety, e.g. $-CH_2SO_3-$;

$R_4$, $R_5$, $R_{11}$, and $R_{12}$ are independently selected from H or a lower alkyl, and are present when $R_2$ and $R_{13}$ are joined in a ring structure with $R_3$ and $R_{10}$, respectively, otherwise $R_4$, $R_5$, $R_{11}$, and $R_{12}$ are absent;

$R_3$, $R_6$, $R_9$, and $R_{10}$ are independently selected from a lower alkyl if "N" is not part of a ring structure;

$R_7$ and $R_9$ are independently selected from H or a lower alkyl if $R_7$ and $R_8$ are not part of a ring structure with $R_6$ and $R_9$, respectively; and $I_{K+}$ represents the position of binding to the ionophore through L.

In still further related embodiments, $R_1$, $R_2$, $R_7$, $R_8$, $R_{13}$, and $R_{14}$ of the chromoionophore of the formula above are each independently selected from H or a lower alkyl; $R_3$, $R_6$, $R_9$, and $R_{10}$ are independently selected from a lower alkyl; and $R_4$, $R_5$, $R_{11}$, and $R_{12}$ are absent. In related embodiments, $R_1$ and $R_{14}$ of the chromoionophore of the formula above are each independently selected from H or a lower alkyl; $R_2$ and $R_{13}$ are joined to form quinolizine ring systems with $R_3$, $R_6$, and $R_7$, and $R_8$, $R_9$, and $R_{10}$, respectively to provide two quinolizine ring systems in the compound; or $R_4$, $R_5$, $R_{11}$, and $R_{12}$ are independently selected from H or a lower alkyl. In further embodiments, $R_1$ and $R_{14}$ are each independently selected from H or a lower alkyl; $R_2$ and $R_{13}$ are joined in thieno-pyridine rings that include $R_3$ and $R_{10}$, respectively to provide two thieno-quinoline ring systems in the chromoionophore; $R_4$, $R_5$, $R_{11}$, and $R_{12}$ are independently selected from H or a lower alkyl. In another related embodiment, wherein $R'_1$ and $R'_2$ are each methyl, and $R'_5$ is $-O(CH_2)_2O-CH_3$.

In another aspect of the invention the invention features a potassium-sensitive chromoionophore comprising the formula below, as well as pharmaceutically acceptable salts thereof:

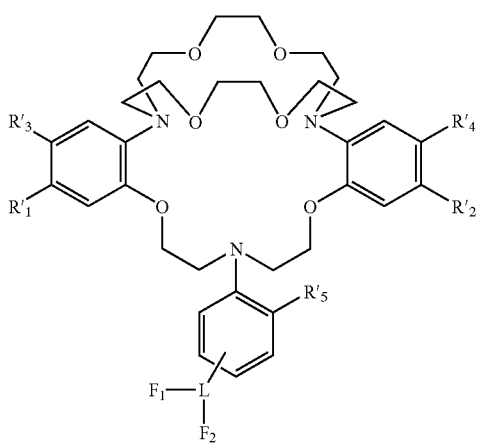

wherein $F_1$ and $F_2$ each represent a chromophoric moiety, where $F_2$ may be present or absent;

$R'_1$ and $R'_2$ are lower alkyls and $R'_3$ and $R'_4$ independently selected from H or a lower alkyl; or, when $F_2$ is absent, $R'_1$ and $R'_2$ are independently selected from a lower alkyl or $F_3$, and $R'_3$ and $R_{14}$ are independently H or lower alkyls; or when $F_2$ is absent, $R'_1$ and $R'_2$ are lower alkyls, and $R'_3$ and $R'_4$ are independently selected from a lower alkyl or $F_3$, wherein $F_3$ is of the formula

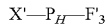
$X'-P_H-F'_3$ where X' is a reactive group, such as amine, amide, succinimidyl ester, or aldehyde, wherein an X' of particular interest is $-[CH_2]_qO-(CH_2)_s-CO-NH-$, $-O-[CH_2]_s-CO-NH-$, or $-[CH_2]_s-CO-NH-$, where q is an integer from 1 to 2 and s is an integer from 2 to 6; $P_H$ is selected from a hydrophilic, water-soluble polymer; and $F'_3$ is a chromophoric moiety insensitive to pH and to potassium binding by the chromoionophore, where $F'_3$ provides a detectable signal that is different from a detectable signal of $F_1$;

$R'_5$ is a substituted or unsubstituted alkyl (e.g. lower alkyl), alkoxy (e.g. lower alkoxy), alkoxyalkoxy, alkoxyaryl, t-alkylester (e.g. t-butyl ester of carboxyloweralkoxy, t-alkylester of carboxyalkoxyalkoxy, succinimidylester of carboxyalkoxy, succinimidylester of carboxyalkoxyalkoxy, aminoalkoxy, aminoalkoxyalkoxy, mercaptoalkoxy, or mercaptoalkoxyalkoxy;

L is a linker selected from a substituted or unsubstituted lower alkyl of the formula $-(CH_2)_v-$ or $-(CH_2)_wNH-$, where v is 0, 1, or 2 and w is 1 or 2; and $F_1$ is a chromophoric moiety which provides a detectable fluorescent signal upon excitation when potassium is bound to the ionophore, wherein when $F_2$ and $F_3$ are absent, $F_1$ is comprises the formulae:

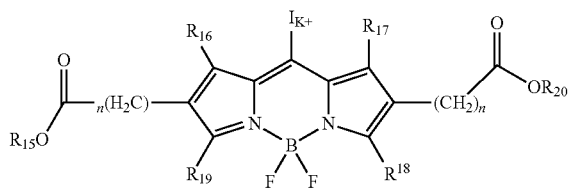

where:

each $R(R_{15}, R_{16}, R_{17}, R_{18}, R_{19}$ and $R_{20})$ is independently selected from H or lower alkyl, and when attached to an oxygen atom of one or both carboxyl groups ($R_{15}, R_{20}$), R is further independently selected from an alkali metal cation, n is an integer from 0 to 6 (i.e., 0, 1, 2, 3, 4, 5, or 6); and $I_{K+}$ represents the position of binding to the ionophore through L;

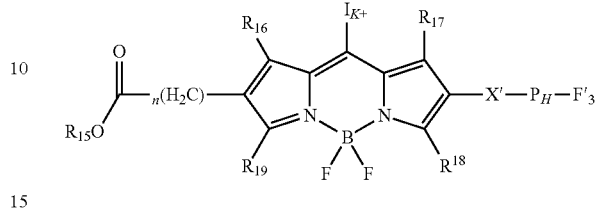

where:

each $R(R_{15}, R_{16}, R_{17}, R_{18}$, and $R_{19})$ is independently selected from H or lower alkyl, and when attached to the oxygen atom of the carboxyl group ($R_{15}$), R is further independently selected from an alkali metal cation, n is an integer from 0 to 6 (i.e., 0, 1, 2, 3, 4, 5, or 6);

$I_{K+}$ represents the position of binding to the ionophore through L; and

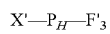
$X'-P_H-F'_3$ is as defined above;
and

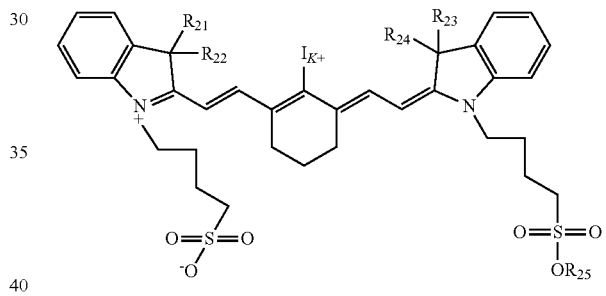

where:

each R ($R_{21}, R_{22}, R_{23}, R_{24}$, and $R_{25}$) is independently selected from H or lower alkyl, and $R_{25}$ is further independently selected from an alkali metal cation, n is an integer from 0 to 6 (i.e., 0, 1, 2, 3, 4, 5, or 6); and $I_{K+}$ represents the position of binding to the ionophore through L; and $F_2$, when present, is of the formula $X-P_H-F'_2$, where X is an alkyl benzamide, succinimidyl ester, or aldehyde;
$P_H$ is a hydrophilic, water-soluble polymer, and
$F'_2$ is a chromophoric moiety that provides a stable detectable signal insensitive to potassium binding and pH, where $F'_2$ provides a detectable signal distinguishable from the detectable signal of $F'_1$.

Other cyanine dyes bearing various substituents on the indole ring nitrogens, e.g., N-benzyl or N-phenyl, are also suitable.

In further embodiments, the invention provides a composition containing a chromoionophore of the invention in a physiologically compatible solution. In further embodiments, the invention provides a pharmaceutically acceptable composition comprising a chromoionophore of the invention.

In other aspects the invention features methods of assessing extracellular potassium ion concentrations in vivo, by delivering a chromoionophore of the invention to an extracellular fluid compartment of a subject; and detecting the presence or absence of a potassium-sensitive detectable signal emitted from the chromoionophore (following excitation), wherein intensity of the detectable signal is indicative of the concentration of potassium ions in the compartment. In related embodiments, detection is accomplished by imaging through one or more tissues of the subject (e.g., skin, bone, and the like), and as such provides for a minimally invasive method of assessing potassium levels in a subject. In further related embodiments, the method including administering a candidate agent to the subject to assess the effect of the candidate agent upon extracellular potassium concentrations in the extracellular fluid compartment. The chromoionophore can be provided in a physiologically acceptable solution, and may include one or more components of a biological sample of the subject.

In another aspect, the invention provides methods for assessing extracellular potassium ion concentrations in a cell or tissue culture by contacting a cell or tissue culture with a chromoionophore of the invention, and detecting the presence of absence of a potassium-sensitive detectable signal emitted from the chromoionophore, wherein intensity of the detectable signal is indicative of the extracellular concentration of potassium ions in the culture. This aspect of the invention can also involve contacting the cell or tissue culture with a candidate agent to assess the effect of the candidate agent upon extracellular potassium concentrations. The invention also features kits comprising a chromoionophore of the invention in a container.

In general, the invention provides for compositions of a chromoionophore of the invention in a physiologically compatible solution, providing ease of use to the end user, and providing for use in vivo, e.g., to assess concentrations of an alkali ion, especially a potassium ion, in a biological compartment. Chromoionophores of the invention can also be used in solutions that mimic or are isotonic with a physiological condition.

Additionally, methods for the determination of $K^+$ concentration in biological systems using of the inventive chromoionophores and compositions containing them are also provided. In some methods, the determination is done in vivo, while others are in vitro. In some embodiments, the subject of interest may be a non-human animal. In other embodiments the subject animal is a mammal. Exemplary methods include screening for agents that modulate $K^+$.

The invention also provides for kits, which may include compounds, compositions, and instructions for executing the methods disclosed herein.

The invention is advantageous in that it provides water soluble, chromoionophores suitable for use in vivo, which exhibit marked increases in fluorescence from a potassium-sensitive chromophore in a very short period of time (e.g., on the order of milliseconds to seconds).

The invention is also advantageous in that the long excitation wavelengths of the chromoionophores allow for imaging through tissues, making the chromoionophores suitable for use in minimally invasive or non-invasive procedures.

These and other aspects and advantages of the invention will be made apparent from the detailed description below.

BRIEF DESCRIPTION OF THE DRAWINGS

The invention will be more fully understood by reference to the following drawings, which are for illustrative purposes only.

Figure 1:
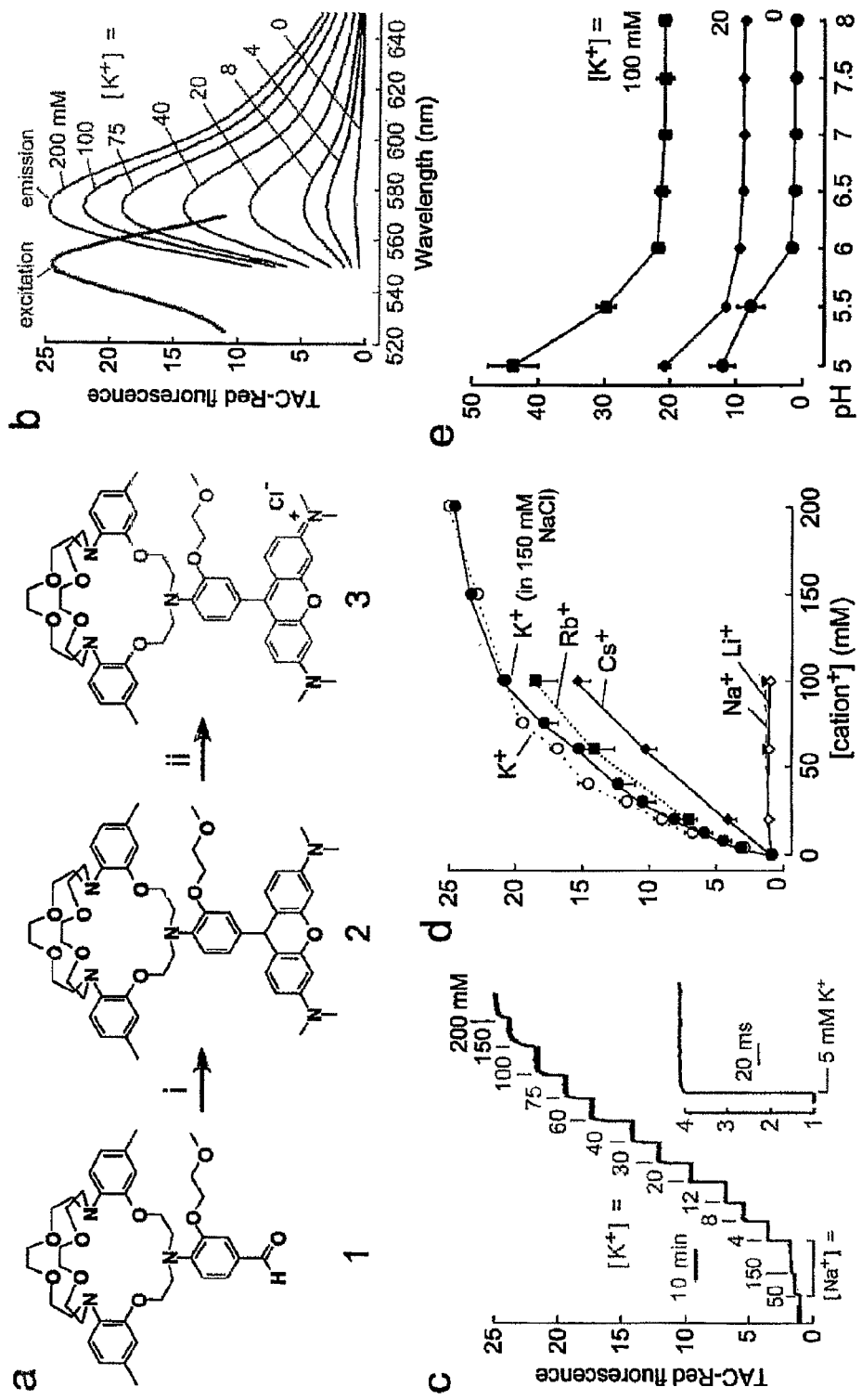
FIG. 1 provides illustrations relating to synthesis and spectroscopic properties of a triazacryptand-based long-wavelength $K^+$-sensing fluorescent indicator TAC-Red. Panel a: Schematic of synthesis of TAC-Red. Panel b: Excitation and emission spectra of 7 µM TAC-Red in 5 mM HEPES pH 7.04 containing indicated [$K^+$]. Panel c: Titration of TAC-Red showing serial additions of NaCl following by KCl. Panel c Inset shows response of TAC-Red fluorescence by stop-flow analysis to an increase in $K^+$ from 0 to 5 mM. Panel d: Titration of TAC-Red fluorescence as a function of cation concentration. Panel e: Dependence of TAC-Red fluorescence on solution pH at indicated $K^+$ concentrations. Panel f: Alternate synthetic route for synthesis of TAC-Red.
Figure 1:
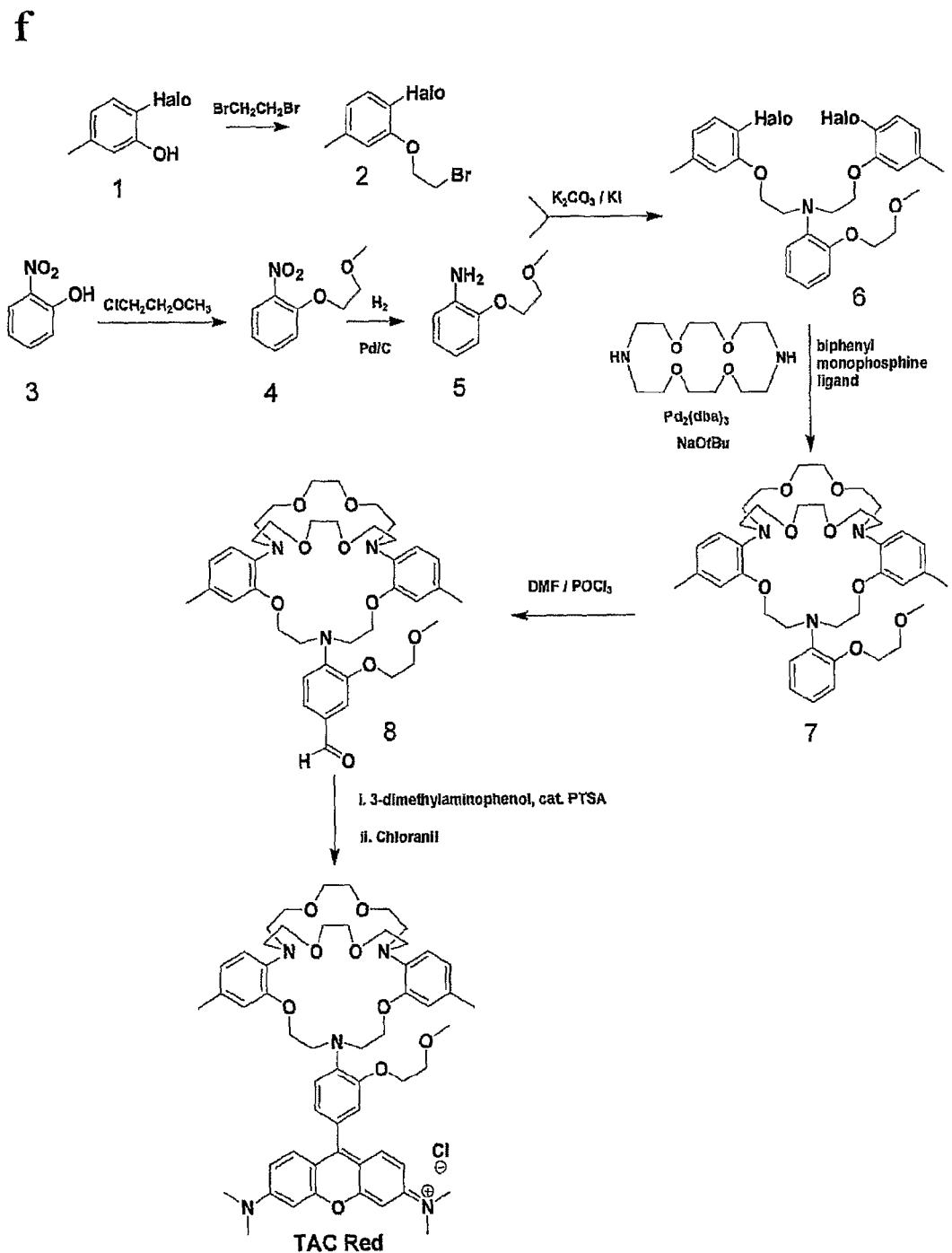

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It should be noted that, as used herein and in the appended claims, the singular forms "a", "and", and "the" include plural referents unless the context clearly dictates otherwise. Thus, for example, reference to "a compound" includes a plurality of such compounds, and reference to "the cell" includes reference to one or more cells and equivalents thereof known to those skilled in the art, and so forth.

The publications discussed herein are provided solely for their disclosure prior to the filing date of the present application, and are incorporated herein by reference. Nothing herein is to be construed as an admission that the present invention is not entitled to antedate such publication by virtue of prior invention. Further, the dates of publication provided may be different from the actual publication dates that may need to be independently confirmed.

DEFINITIONS

"Potassium ionophore" as used herein refers to an ionophore that selectively binds potassium over other alkali ions, especially biologically relevant alkali ions such as sodium.

By "selectively binds" or "specifically binds" in the context of the potassium-binding chromoionophore conjugates of the invention is meant that the conjugate binds potassium preferentially when in the presence of sodium, and preferably in the presence of increasing concentrations of sodium ions.

"Chromophore" and "dye" are used interchangeable herein to generally refer to a chemical group capable of selective light absorption resulting in colored detectable signal, and encompasses fluorochromes (also referred to as fluorophores).

"Fluorochrome" and "fluorophore" refer to any of a group of compounds (often referred to as fluorescent dyes) which emit light via fluorescence, usually only after excitation, and are generally used as, for example, a label in examination of tissues and cells by fluorescence microscopy. Reference to "fluorochrome" or "fluorophore" in the context of the chromophores of the conjugates of the invention is not meant to be limiting, but rather is exemplary.

"Luminescence" refers to the emission of light that does not derive energy from the temperature of the emitting body, as in phosphorescence, fluorescence, and bioluminescence. Luminescence is generally caused by chemical, biochemical, or crystallographic changes, the motions of subatomic particles, or radiation-induced excitation of an atomic system.

"Fluorescence" is a luminescence involving an optical phenomenon in which a molecule absorbs a high-energy photon and re-emits it as a lower-energy (longer-wavelength) photon. The energy difference between the absorbed and emitted photons ends up as molecular vibrations (heat).

Chromoionophore" as used herein refers to a conjugate of an ionophore and at least one chromophore (e.g., fluorophore or luminophore), and may further include a water soluble polymer (e.g., dextran) or other moieties of interest. The term "conjugate" is often used herein to refer to a chromoionophore of the invention. An ionophore present in a chromoionophore is often referred to herein without limitation as a "chromoionophoric moiety". A chromophore present in a chromoionophore is often referred to herein without limitation as a "ionophoric moiety".

"Fluoroionophore" as used herein refers to a conjugate of an ionophore and at least one fluorophore, and may further include a water soluble polymer (e.g., dextran) or other moieties of interest. The term "conjugate" is often used herein to refer to a fluoroionophore of the invention.

"Long wavelength excitation" as used in the context of the chromoionophore conjugates of the present invention refers to an excitation wavelength that is suitable for use in an in vivo setting, and elicits emission spectra from a chromophore moiety at an excitation wavelength so as to minimize background fluorescence (e.g., as from cellular fluorescence), interference by hemoglobin oxygenation, photobleaching, and light-induced injury of the tissues in the area of analysis of potassium concentrations. Usually, "long wavelength excitation" refers to an excitation wavelength of at least about 500 nm or greater, at least about 650 nm or greater, at least about 700 nm or greater, and the like.

The term "membrane impermeable" in reference to the chromoionophoric, potassium indicator compounds of the invention indicates that the compound does not cross a cell membrane (particularly a mammalian cell membrane) of an intact cell to a significant or detectable degree. This characteristic provides that detection of potassium using the inventive compounds is indicative of potassium that is extracellular, with little or no signal generated by the compound in response to the intracellular potassium that may be present in intact cells.

The term "modulates", as in, for example, "modulates potassium levels" particularly in reference to an agent (e.g., a candidate agent) is meant that the agent directly or indirectly effects an increase or decrease in an associated cellular event, e.g., a cellular event that affects (directly or indirectly) potassium levels, particularly potassium levels in an extracellular space of a biological compartment.

The term "stimulus" refers to an environmental condition, e.g., exposure to an agent, temperature, light, osmolarity, and the like, which may elicit a response, e.g., modulation of potassium concentration.

The term "biological compartment" generally refers to a space that is defined by a surrounding tissue or membrane, e.g., as in a space surrounding or within an organ. The space defined in such biological compartments is often referred to as an extracellular fluid compartment.

A "biological sample" encompasses a variety of sample types obtained from an individual and can be used in a diagnostic or monitoring assay. The definition encompasses includes samples that have been manipulated in any way after their procurement, such as by treatment with reagents; washed; or enrichment for certain cell populations. The term "biological sample" encompasses a clinical sample, and also includes cells in situ or ex vivo, including organs, tissues, culture, cell supernatants, tissue samples (e.g., biopsy specimen), and the like.

The term "physiological conditions" is meant to encompass those conditions compatible with living cells, e.g., predominantly aqueous conditions of a temperature, pH, salinity, etc. that are compatible with living cells. A "physiologically acceptable solution" is one that is compatible with, and thus suitable for contacting, living cells, including living cells in vivo. In some embodiments, particularly where the solution is for in vivo delivery, a physiologically acceptable solution contains one or more components from a biological sample. "Components of a biological sample" includes both naturally-occurring and artificial substances obtained from or that mimic components in a biological sample, e.g., serum, fetal calf serum, NuSerum, cerebrospinal fluid, artificial cerebrospinal fluid, and the like). For example, where the solution is to be delivered to the brain, the physiologically acceptable solution can contain naturally-occurring or artificial cerebrospinal fluid.

As used herein, "contacting" has its normal meaning and refers to combining two or more entities (e.g., a chromoionophore conjugate and a cell (e.g., in a tissue), a chromoionophore conjugate, a candidate agent, and a cell, etc.). Contacting can occur in vivo (e.g., in situ (e.g., in a space defined in a biological compartment)) or in vitro (e.g., in an organ culture).

The term "agent" includes any substance, molecule, element, compound, entity, or a combination thereof. It includes, but is not limited to, e.g., proteins (including antibodies), oligopeptides, small organic molecules, polysaccharides, polynucleotides (e.g., DNA or RNA, including polynucleotides encoding a gene product of interest, or which act as a cell modulator without transcription or without translation), and the like. It can be a natural product, a synthetic compound, or a chemical compound, or a combination of two or more substances. Unless otherwise specified, the terms "agent," "substance," and "compound" can be used interchangeably.

The term "analog" is used herein to refer to a molecule that structurally resembles a molecule of interest but which has been modified by replacing a specific substituent of the reference molecule with an alternate substituent. Compared to the starting molecule, an analog may exhibit the same, similar, or altered or improved utility. Synthesis and screening of analogs is an approach that is well known in the art.

The terms "subject" and "patient" refer to a member or members of any animal (mammalian or non-mammalian) species with which a conjugate of the invention finds use (e.g., to examine a potassium level in a biological compartment of a subject and/or in a biological sample obtained from a subject). Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be of particular interest (e.g., in the context of experimental investigations).

A "pharmaceutically acceptable excipient," "pharmaceutically acceptable diluent," and "pharmaceutically acceptable carrier" are used interchangeably herein and without limitation to refer to an excipient, diluent, or carrier useful in preparing a composition for administration to a subject that is generally safe, non-toxic and neither biologically nor otherwise undesirable, and include those acceptable for veterinary use as well as human pharmaceutical use. Of particular interest in the present invention are "pharmaceutically acceptable excipients," "pharmaceutically acceptable diluents," and "pharmaceutically acceptable carriers" that are present in a composition containing a chromoionophore of the invention, where the composition is to be delivered to a biological compartment (e.g., in a living animal or to a tissue ex vivo (e.g., as in an organ culture). In general, the "pharmaceutically acceptable excipient," "pharmaceutically acceptable diluent," or "pharmaceutically acceptable carrier" are selected so as not to substantially interfere with the potassium-binding or luminescent (fluorescent) properties of the chromoionophore with which it may be used (e.g., in a composition).

A "pharmaceutically acceptable salt" of a compound means a salt that is pharmaceutically acceptable as defined above, and does not significantly negatively affect the desired characteristics of the chromoionophore compound with which it is associated. In general, since the chromoionophores of the invention contain at least one positively charged amine group, salts of interest are generally amino salts, particularly those formed with a suitable anion, so as to provide for a substantially neutrally charged compound. Such salts are generally acid halide salts, such as a chloride salt. In general, any conventional pharmaceutically acceptable salt is contemplated.

As used herein, a "pharmaceutical composition" is meant to encompass a composition suitable for administration to a subject. In general a "pharmaceutical composition" is sterile, and preferably free of contaminants that are capable of eliciting an undesirable response within the subject or a tissue in or derived from the subject (e.g., the compound(s) in the pharmaceutical composition is pharmaceutical grade). Pharmaceutical compositions can be designed for administration to a subject (e.g., to accomplish delivery of a chromoionophore in the composition) by a number of different routes, which routes are usually parenteral or topical, and include any route that provides for delivery of the composition to a biological compartment.

The term "organic group" and "organic radical" as used herein means any carbon-containing group, including hydrocarbon groups that are classified as an aliphatic group, cyclic group, aromatic group, functionalized derivatives thereof and/or various combination thereof.

The term "aliphatic group" means a saturated or unsaturated linear or branched hydrocarbon group and encompasses alkyl, alkenyl, and alkynyl groups, for example.

The term "alkyl group" means a substituted or unsubstituted, saturated linear or branched hydrocarbon group or chain (e.g., $C_1$ to $C_8$) including, for example, methyl, ethyl, propyl, hexyl, nonyl, isopropyl, tert-butyl, heptyl, iso-propyl, n-octyl, dodecyl, octadecyl, amyl, 2-ethylhexyl, and the like.

"Lower alkyl" as used herein generally refers to an alkyl group of $C_1$ to $C_6$, $C_1$ to $C_5$, or $C_1$ to $C_4$, which may be linear ($C_1$ to $C_6$, $C_1$ to $C_5$, or $C_1$ to $C_4$) or branched ($C_2$ to $C_6$, $C_2$ to $C_5$, or $C_2$ to $C_4$).

The term "substituted alkyl" means the above defined alkyl group substituted from one to three times by a hydroxy, protected hydroxy, amino, protected amino, cyano, halo, trifluoromethyl, mono-substituted amino, di-substituted amino, lower alkoxy, lower alkylthio, carboxy, protected carboxy, or a carboxy, amino, and/or hydroxy salt.

The term "alkenyl group" means an unsaturated, linear or branched hydrocarbon group with one or more carbon-carbon double bonds, such as a vinyl group.

The term "alkynyl group" means an unsaturated, linear or branched hydrocarbon group with one or more carbon-carbon triple bonds.

The term "cyclic group" means a closed ring hydrocarbon group that is classified as an alicyclic group, aromatic group, or heterocyclic group.

The term "alicyclic group" means a cyclic hydrocarbon group having properties resembling those of aliphatic groups.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl) hexyl, and the like.

As used in conjunction with the substituents for the heteroaryl rings, the terms "substituted (cycloalkyl)alkyl" and "substituted cycloalkyl" are as defined below substituted with the same groups as listed for a "substituted alkyl" group.

The term "aromatic group" or "aryl group" means a mono- or polycyclic aromatic hydrocarbon group, and may include one or more heteroatoms, and which are further defined below.

The term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms. The term "heterocyclic group" means a closed ring hydrocarbon in which one or more of the atoms in the ring are an element other than carbon (e.g., nitrogen, sulfur, oxygen, etc.), and are further defined below. The five-membered or six-membered rings (which can be optionally substituted) can also or alternatively optionally be fused to an aromatic 5-membered or 6-membered ring system. For example, the rings can be optionally fused to an aromatic 5-membered or 6-membered ring system, such as quinolizine ring systems, thieno-pyridine ring systems, pyridine ring systems, or a triazole ring system.

The terms "quinolizine ring systems" and "thieno-pyridine ring systems" refer to polycyclic ring structures having a quinolizine structure and a thieno-pyridine structure, respectively. The terms include the presence of additional ring(s) fused to the quinolizine structure and/or thieno-pyridine structure and further include unsaturated, as well as fully or partially saturated, ring systems.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are amino, protected amino, amino salts, mono-substituted amino, di-substituted amino; from one to three halo, trihalomethyl; carboxy, protected carboxy, carboxylate salts; hydroxy, protected hydroxy, salts of a hydroxy group; lower alkoxy, lower alkylthio, alkyl, substituted alkyl, cycloalkyl, substituted cycloalkyl, (cycloalkyl)alkyl, substituted (cycloalkyl)alkyl; phenyl, substituted phenyl, phenylalkyl, and (substituted phenyl)alkyl; or thiol; usually amino, carboxy or thiol in the context of the chromophores useful in the present invention. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

The term "(substituted phenyl)alkyl" means one of the above substituted phenyl groups attached to one of the above-described alkyl groups.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

DETAILED DESCRIPTION OF THE INVENTION

Introduction

The invention provides chromoionophore compounds comprising a triazacryptand ("TAC") $K^+$-binding ionophore conjugated to at least a first chromophoric moiety (e.g., xanthylium, julolidine, or rhodamine), which compounds may further comprise a second chromophoric moiety to provide for a dual wavelength conjugate, which can facilitate absolute determination of $K^+$ concentration. The invention further provides methods and kits for use in the determination of $K^+$ concentrations in biological systems, either in vitro or in vivo, using embodiments of inventive chromoionophores.

The compositions and methods of the invention will now be described in more detail.

Chromoionophore Compounds for Detection of Potassium

The compounds of the invention are generally interchangeably referred to herein as "chromoionophore", then this would be changed to "potassium-binding chromoionophores", "potassium chromoionophores", "fluorescent potassium indicators", or "chromoionophore conjugates". In embodiments of particular interest, the compounds include a potassium-binding ionophore covalently bound to a chromophore, and are referred to interchangeably herein as "potassium-binding fluoroionophores", "potassium fluoroionophores", "fluorescent potassium indicators", or "fluoroionophore conjugates". Reference to fluoroionophore and like terms herein is meant to be exemplary of the chromoionophores of the invention.

The general aim of the invention is to provide a chromoionophore conjugate compound composed of a $K^+$-binding ionophore (such as a triaza-cryptand ("TAC")) covalently linked to a long-wavelength excitation chromophore (e.g., having an excitation wavelength of at least 500 nm or greater, usually at least 520 nm or greater, usually at least 530 nm or greater, more usually 540 nm or greater), so that the resulting conjugate is water-soluble, selectively binds potassium over a wide concentration range (including a physiologically relevant range) of from 0 to about 150 mM, usually up to about 120 mM or 140 mM, is insensitive to pH, exhibits a high $K^+$-to-$Na^+$ selectivity, provides for a rapid change in intensity of a detectable signal in response to changes in $K^+$ (but preferably little or no detectable change in fluorescence in response to changes in other environmental conditions, such as increasing $Na^+$, changes in pH, and the like).

The properties of the chromoionophores of the invention desirably include a change in fluorescence of at least 5-fold, at least 10-fold, or at least 12-fold, usually at least 14-fold or greater over a potassium concentration range of about 0-150 mM, 0-100 mM, 0-75 mM, or 0-65 mM, usually 0-50 mM, 0-45 mM, or 0-40 mM.

The chromoionophores of the invention also preferably exhibit a $K^+$-to-$Na^+$ selectivity ratio of at least 10, 20, 25, 30 or more, usually at least 30 (e.g., the signal intensity in response to potassium is about 30-fold greater than the signal intensity in the presence of the same concentration of sodium). The chromoionophores also preferable exhibit a rapid response under changing potassium concentration issues, e.g., an observable change in fluorescence intensity within milliseconds (ms) (e.g., less than 1 ms, 10 ms, 50 ms, 100 ms, etc.), within a few seconds, e.g., within 1 second, 4 seconds, 6 seconds, 8 seconds, 10 seconds, 12 seconds, 15 seconds, 24 seconds, 30 seconds, 36 seconds, 48 seconds, 54 seconds, or less.

The chromoionophores of the invention also should exhibit stability of fluorescent signal (i.e., little or no detectable change in intensity) in the presence of other alkali ions, divalent cations and various anions, including changes in pH. Of particular interest are chromoionophores that exhibit a stable fluorescent signal in the presence of changes in physiological pH, where the physiological range of pH in most biological compartments is between about 6.5 and 7.5, usually around 6.8. Also, particularly for in vivo applications, the chromoionophores should be sufficiently water soluble, membrane impermeant, and non-toxic (so as to reduce changes in the physiological environment by virtue of the presence of the chromoionophore).

In one aspect, the invention provides a chromoionophore having the characteristics described above, and containing a potassium-binding ionophore covalently attached to a chromophore. In another aspect, the invention provides a chromoionophore having the characteristics described above, as well as two different chromophores covalently linked to the conjugate. In this aspect, the conjugates can provide for a first detectable signal when potassium is bound to the ionophore portion of the conjugate, and a second detectable signal that is substantially insensitive to potassium concentrations. Such conjugates, which may be referred to as "dual wavelength chromophores" or "dual wavelength potassium indicators", can be used to determine an absolute value of potassium in biological systems. For example, analysis of the ratio of fluorescence intensity of the first detectable signal to the fluorescence intensity of the second detectable signal can be used to assess the potassium concentration.

In some embodiments, water solubility is provided or enhanced by including a water soluble polymer in the conjugate (e.g., dextran).

In one embodiment of particular interest, the chromoionophores of the invention can be represented by the formula:

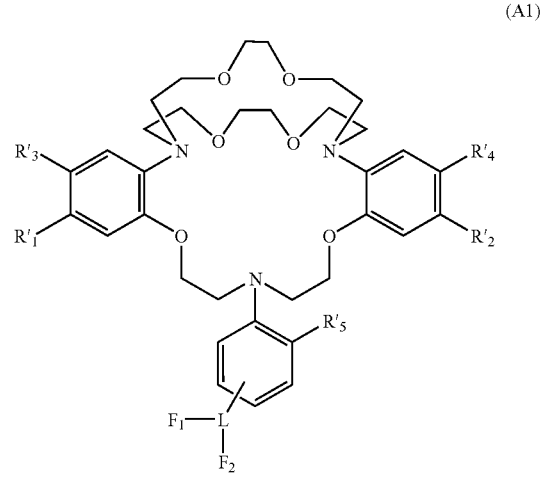

(A1)

wherein $R'_1$ and $R'_2$ are lower alkyls and $R'_3$ and $R'_4$ independently selected from H or a lower alkyl; or, when $F_2$ is absent, $R'_1$ and $R'_2$ are independently selected from a lower alkyl or $F_3$, and $R'_3$ and $R'_4$ are independently H or lower alkyls; or when $F_2$ is absent, $R'_1$ and $R'_2$ are lower alkyls, and $R'_3$ and $R'_4$ are independently selected from a lower alkyl or $F_3$, wherein $F_3$ is of the formula

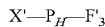

where

X' is a reactive group, such as amine, amide, succinimidyl ester, or aldehyde, wherein an X' of particular interest is

or

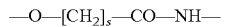

where q is 1 or 2;

s is an integer from 2 to 6;

$P_H$ is selected from a hydrophilic, water-soluble polymer, such as dextran, polyethylene oxide, polyethyleneimine (PEI), polylactide, polyglycolide, PLGA, and the like; and $F'_3$ is a chromophoric moiety insensitive to potassium binding by the compound and pH, and is usually a green dye such as a boron-dipyrromethene dye (BODIPY) or green rhodamine, preferably BODIPY, or a red dye such as tetramethylrhodamine (TMR), where $F'_3$ provides a detectable signal that is different from (i.e., can be distinguished from), the detectable signal of $F_1$, wherein when more than one of $R'_1$, $R'_2$, $R'_3$ and $R'_4$ are $F_3$, $F'_3$ is preferably the same chromophoric moiety;

$R'_5$ is a substituted or unsubstituted alkyl (e.g. lower alkyl), alkoxy (e.g. lower alkoxy), alkoxyalkoxy, alkoxyaryl, t-alkylester (e.g. t-butyl ester of carboxyloweralkoxy, t-alkylester of carboxyalkoxyalkoxy, succinimidylester of carboxyalkoxy, succinimidylester of carboxyalkoxyalkoxy, aminoalkoxy, aminoalkoxyalkoxy, mercaptoalkoxy, or mercaptoalkoxyalkoxy, where exemplary $R'_5$ groups include —[OCH$_2$CH$_2$]$_n$OCH$_3$;

—[OCH$_2$CH$_2$]$_n$O—(CH$_2$)$_m$—COO-t-butyl;

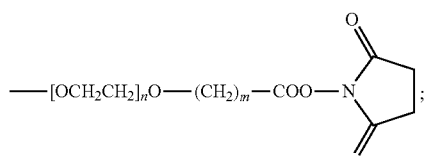

—[OCH$_2$CH$_2$]$_n$O—(CH$_2$)$_m$—NH$_2$; or

—[OCH$_2$CH$_2$]$_n$O—(CH$_2$)$_m$—SH where n is 0 or 1, usually 1;

m is an integer from 0 to 6 (i.e., 0, 1, 2, 3, 4, 5, or 6);

L is a "linker" which attaches the ionophore and chromophore(s), which linker can be a single covalent bond (C—C) (particularly where $F_2$ is absent) or a substituted or unsubstituted lower alkyl of the formula —(CH$_2$)$_v$— or —(CH$_2$)$_w$-NH$_2$—, where v is 0, 1, or 2 and w is 1 or 2; a substituted phenyl group; or a bifunctional group (e.g., p-amino-benzoic acid or esters thereof, diaminoalkyl, and the like); and at least one chromophoric moiety $F_1$ is attached to L, with a second chromophoric moiety, $F_2$, being optionally present, wherein when $F_1$ is the only chromophoric moiety (e.g., when $F_2$ is absent and none of $R'_1$ or $R'_2$, $R'_3$, or $R'_4$ is a chromophoric moiety (i.e., when both $F_2$ and $F_3$ are absent)), then $F_1$ is a chromophoric moiety as exemplified by Formulae II, V, VI, VII, or VIII below;

when the compound comprises two or more chromophoric moieties (e.g., when $F_2$ is present or when at least one of $R'_1$ or $R'_2$, $R'_3$, or $R'_4$ comprise a chromophoric moiety), then $F_1$ may be any suitable chromophore which can provide a detectable fluorescent signal upon potassium binding to the ionophore, preferably within the fluorescence spectrum from about 550 nm to 750 nm (e.g., rhodamine, Texas red type and Alexa fluor), which chromophores can be coupled to the conjugate through, for example, a reactive succinimidyl ester to react with the free amine of L (see, e.g., FIG. 13); and $F_2$, when present (in a dual wavelength conjugate of the invention), is of the formula

where

X selected from a reactive group, such as amine, amide, succinimidyl ester, or aldehyde;

$P_H$ is selected from a hydrophilic, water-soluble polymer, such as dextran, polyethylene oxide, polyethyleneimine (PEI), polylactide, polyglycolide, PLGA, and the like; and $F'_2$ is selected from a dye insensitive to potassium binding and pH, and is usually a green dye such as a boron-dipyrrpmethene (BODIPY) dye or green rhodamine, preferably BODIPY, such as "Lime", where $F'_2$ provides a detectable signal that is different from, and can be distinguished from, the detectable signal of $F_1$.

The chromoionophores of the invention are described in more detail below.

Chromoionophores Having a Single Chromophoric Moiety "Single Wavelength Chromoionophores")

In one aspect, the invention provides chromoionophores having a single chromophore (e.g., a fluorophore or luminiphore, usually a fluorophore) covalently bound through a single covalent bond (referred to as a "linker") to a TAC ionophore. Such chromoionophores can be described by the general formula:

$$I_K\text{-L-D} \qquad (A2)$$

where $I_K$ in Formula A2 is a potassium-binding TAC ionophore;

L is a "linker" which can be a single covalent bond (C—C) or a substituted or unsubstituted lower alkyl of the formula —(CH$_2$)$_v$— or —(CH$_2$)$_w$-NH—, where v is 0, 1, or 2 and w is 1 or 2; a substituted phenyl, or a bifunctional group (e.g., p-amino-benzoic acid or esters thereof, diaminoalkyl, and the like); and D is a chromophore (also referred to herein as a "dye") having a long-wavelength excitation spectra, and comprises at least one positive charge (e.g., so as to provide for enhanced water solubility).

The ionophoric moieties ($I_K$) and chromophoric moieties (D) are described in more detail below.

Potassium-Binding Ionophoric Moieties for Use in Single-Wavelength Chromoionophores The chromoionophore of the invention generally include a potassium-binding triazacryptand ("TAC") ionophore moiety conjugated to at least one chromophore. In general the TAC ionophore can be any suitable potassium-binding TAC moiety that can provide for the desired characteristics of the conjugates of the invention (e.g., potassium selectivity, sodium and pH insensitivity, etc.). Exemplary TAC ionophores are described in, for example, U.S. Pat. No. 6,211,359. Of particular interest is the TAC ionophore of the chromoionophore of the invention is of the general Formula I as follows:

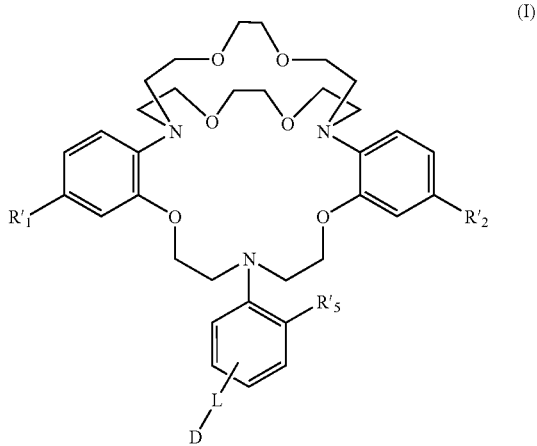

(I)

where: $R'_1$, $R'_2$ are independently selected from a lower alkyl, are usually the same, and are preferably methyl;

L is a "linker" as defined above in Formulae A1 and A2, where embodiments of particular interest include those in which L is a single covalent bond or a substituted or unsubstituted lower alkyl of the formula —$(CH_2)_v$— or —$(CH_2)_w$—$NH_2$—, where v is 0, 1, or 2 and w is 1 or 2; and $R'_5$ is a substituted or unsubstituted alkyl (e.g. lower alkyl), alkoxy (e.g. lower alkoxy), alkoxyalkoxy, alkoxyaryl, t-alkylester (e.g. t-butyl ester of carboxyloweralkoxy, t-alkylester of carboxyalkoxyalkoxy, succinimidylester of carboxyalkoxy, succinimidylester of carboxyalkoxyalkoxy, aminoalkoxy, aminoalkoxyalkoxy, mercaptoalkoxy, or mercaptoalkoxyalkoxy, where exemplary $R'_5$ groups include

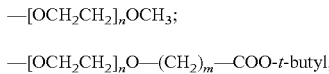

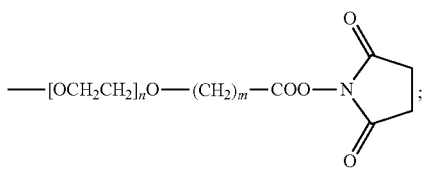

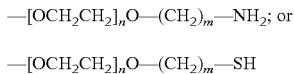

n is 0 or 1, usually 1;

m is an integer from 0 to 6 (i.e., 0, 1, 2, 3, 4, 5, or 6);

D represents a chromophore moiety (e.g., as set out in Formula II below), where D may be provided in the para or meta, usually the para, position relative to the amine substituent, and where the ionophore is linked to the chromophore by a single covalent bond (which may be referred to herein as a "linker", as in the formula $I_{K+}$-L-D set out in Formula 1a below).

Exemplary chromophoric moieties suitable for use in Formula I include xanthylium-based dyes (e.g., rhodamine dyes); BODIPY dyes; cyanine near infrared dyes; and derivatives thereof. In general, the chromophore moiety is one that has a relatively long excitation wavelength. In embodiments of particular interest, -L-D is in the para position relative to the amine of the ionophoric moiety.

In embodiments of specific interest, the ionophore of the chromoionophore is of the forula:

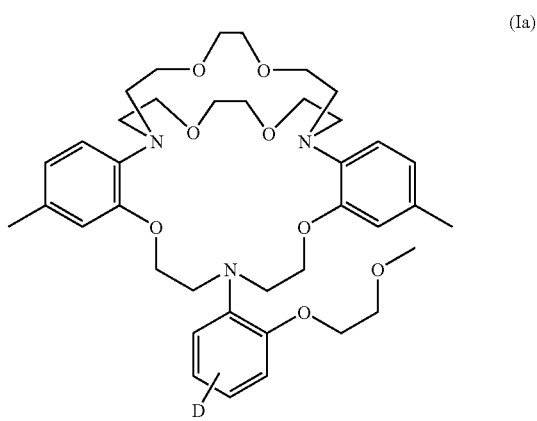

(Ia)

where D represents a chromophore as set out in Formula II below, where D may be provided in the para or meta, preferably the para, position relative to the amine substituent.

Chromoionophoric Moieties for Use in Chromoionophores Having a Single Chromophore Conjugated to an Ionophoric Moiety In specific embodiments, where the chromoionophore has a single chromophoric moiety, the chromophoric moiety can be any suitable chromophore, preferably one that has a long excitation wavelength. Such chromophores include xanthene- or xanthylium-based dyes, polypyrrole-based dyes, and cyanine near infrared dyes. Specific exemplary chromophores include julolidine, Alexa Fluor, a BODIPY such as "Lime", and IR-783.

Exemplary chromophores of particular interest for use in single wavelength chromoionophores of the invention include those of the formula:

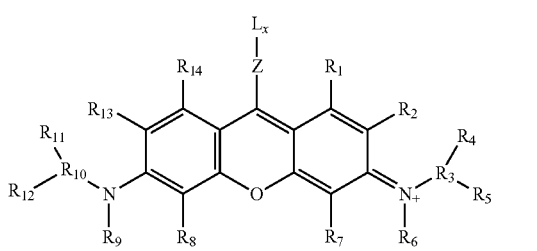

(IIa)

where $L_x$ indicates binding to the linker L;

$R_1$ and $R_{14}$ are each independently selected from H or a lower alkyl;

$R_2$ and $R_{13}$ are joined to form quinolizine ring systems that includes $R_3$, $R_6$, and $R_7$, and $R_8$, $R_9$, and $R_{10}$, respectively, to provide one or two substituted or unsubstituted, usually unsubstituted, quinolizine ring systems in the compound; or $R_2$ and $R_{13}$ are joined to form in the compound pyridine or thieno-pyridine ring systems that include $R_3$ and $R_{10}$, respectively, to provide one or two pyridine ring systems or one or two thieno-pyridine ring systems in the compound, and wherein the thieno-pyridine ring systems are thieno-quinoline ring systems;

wherein when $R_2$ and $R_{13}$ are present in ring structures, usually form the same ring structures, and at least one of the ring structures contains a positively charged amine, and when $R_2$ and $R_{13}$ are joined to form pyridine ring systems that include $R_3$ and $R_{10}$, respectively, the pyridine ring systems are substituted by a methylene or polymethylene group that is substituted by an anionic moiety, e.g. —$CH_2SO_3^-$;

$R_4$, $R_5$ $R_{11}$, and $R_{12}$ are independently selected from H or a lower alkyl, and are present when $R_2$ and $R_{13}$ are joined in a ring structure with $R_3$ and $R_{10}$, respectively, otherwise $R_4$, $R_5$, $R_{11}$, and $R_{12}$ are absent;

$R_3$, $R_6$, $R_9$, and $R_{10}$ are independently selected from a lower alkyl if "N" is not part of a ring structure; and $R_7$ and $R_8$ are independently selected from H or a lower alkyl if $R_7$ and $R_8$ are not part of a ring structure with $R_6$ and $R_9$, respectively; and Z is of the formula:

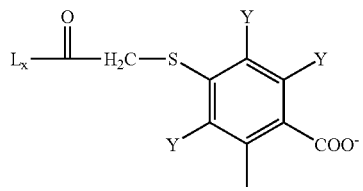

wherein Y are each independently halides (e.g., Cl, Br, particularly Cl), $L_x$ indicates binding to the linker L in the compound (see, e.g., Formula A1), and Z is present when $R_2$ and $R_{13}$ are joined to form pyridine ring systems that include $R_3$ and $R_{10}$, respectively.

In other embodiments, the single wavelength compounds are generally described by Formula (IIb), Formula (IIc), and Formula (IId) as follows:

where:

$R_1$ and $R_{14}$ are each independently selected from H or a lower alkyl, and are each generally the same, and usually are H or methyl, usually H;

$R_2$ and $R_{13}$ are each independently selected from H or a lower alkyl, and are each generally the same, and usually are H or methyl, and usually are H, unless:

$R_2$ and $R_{13}$ are joined to form quinolizine ring systems that include $R_3$, $R_6$, and $R_7$, and $R_8$, $R_9$, and $R_{10}$, respectively, to provide one or two quinolizine ring systems in the compound; or $R_2$ and $R_{13}$ are joined to form in the compound pyridine or thieno-pyridine ring systems that include $R_3$ and $R_{10}$, respectively, to provide one or two pyridine ring systems or one or two thieno-pyridine ring systems in the compound, and wherein the thieno-pyridine ring systems are thieno-quinoline ring systems;

wherein when $R_2$ and $R_{13}$ are present in ring structures, at least one of the ring structures contains a positively charged amine, and when $R_2$ and $R_{13}$ are joined to form pyridine ring systems that include $R_3$ and $R_{10}$, respectively, the pyridine ring systems are substituted by a methylene or polymethylene group that is substituted by an anionic moiety, e.g. —$CH_2SO_3^-$; where $R_2$ and $R_{13}$, when present in ring structures, usually form the same ring structures with the proviso that at least one ring structure (e.g., the ring structure including $R_{13}$) contains a positively charged amine as set out in Formula II above;

$R_4$, $R_5$ $R_{11}$, and $R_{12}$ are independently selected from H or a lower alkyl (usually methyl), may be the same moieties, and are present when $R_2$ and $R_{13}$ are joined in a ring structure with $R_3$ and $R_{10}$, respectively, (or, stated differently, when "N" is part of a ring structure), particularly when the ring structure is a thieno-pyridine structure (to provide a thieno-quinoline ring in the compound, in which $R_4$, $R_5$ $R_{11}$, and $R_{12}$ are usually methyl), otherwise $R_4$, $R_5$ $R_{11}$, and $R_{12}$ are absent;

$R_3$, $R_6$, $R_9$, and $R_{10}$ are independently selected from a lower alkyl, usually methyl, if "N" is not part of a ring structure;

$R_7$ and $R_8$ are independently selected from H or a lower alkyl if $R_7$ and $R_8$ are not part of a ring structure with $R_6$ and $R_9$, respectively; and $I_{K+}$ represents binding to the linker L in the Formula above (e.g., to bind to a triazacryptand ionophoric moiety);

(IIb)

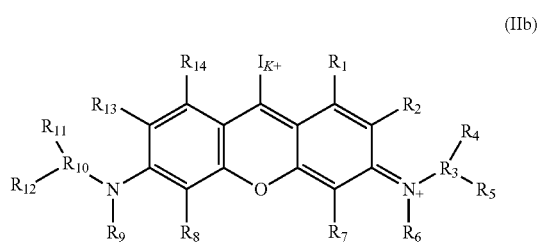

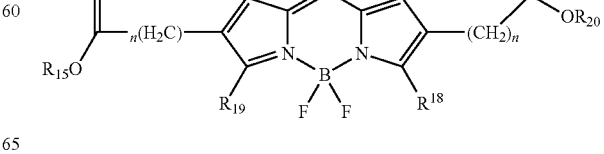

(IIc)

where:

each R ($R_{15}$, $R_{16}$, $R_{17}$, $R_{18}$, $R_{19}$ and $R_{20}$) is independently selected from H or lower alkyl, and when attached to an oxygen atom of one or both carboxyl groups ($R_{15}$, $R_{20}$), R is further independently selected from an alkali metal cation, n is an integer from 0 to 6 (i.e., 0, 1, 2, 3, 4, 5, or 6); and zwitterionic-like structures where the chromoionophore includes a carboxy or sulfonic acid function to provide for enhanced water solubility.

Table I below provides a listing of exemplary chromoionophores of Formula II, where the ionophore, ($I_{K+}$) in the formula, is given by Formula I above. "C" refers to the compound designation for purposes of reference in the table.

TABLE 1

| "C" | $R_1$ | $R_2$ | $R_3$ | $R_4$ | $R_5$ | $R_6$ | $R_7$ | $R_8$ | $R_9$ | $R_{10}$ | $R_{11}$ | $R_{12}$ | $R_{13}$ | $R_{14}$ |
|---|---|---|---|---|---|---|---|---|---|---|---|---|---|---|
| C1 | —H | H | —CH or $CH_3$ | $X^1$ | X | —$CH_3$ | H | H | —$CH_3$ | —CH or $CH_3$ | X | X | H | H— |
| C1a | —$CH_3$ | —$CH_3$ | CH or $CH_3$ | X | X | H | —$CH_3$ | —$CH_3$ | H | —CH or $CH_3$ | X | X | H | —$CH_3$ |
| C1b | ethyl | —$CH_3$ | CH or $CH_3$ | X | X | ethyl | ethyl | ethyl | ethyl | —CH or $CH_3$ | X | X | —$CH_3$ | ethyl |
| C1c | —H | H | ethyl | X | X | ethyl | H | H | ethyl | ethyl | X | X | H | H |
| C2 | —H | $DQ^2$ | DQ | $X^1$ | X | DQ | DQ | DQ | DQ | DQ | X | X | DQ | H |
| C2a | —$CH_3$ | DQ | DQ | X | X | DQ | DQ | DQ | DQ | DQ | X | X | DQ | —$CH_3$ |
| C2b | ethyl | DQ | DQ | X | X | DQ | DQ | DQ' | DQ' | DQ' | X | X | DQ | ethyl |
| C3 | —H | $TQ^3$ | TQ | $CH_3$ | $CH_3$ | —$CH_3$ | H | H | —$CH_3$ | TQ | $CH_3$ | $CH_3$ | TQ | H |
| C3a | —$CH_3$ | TQ | TQ | H | H | ethyl | —$CH_3$ | H | ethyl | TQ' | H | H | TQ | —$CH_3$ |
| C3b | ethyl | TQ | TQ | ethyl | ethyl | —H | —$CH_3$ | —$CH_3$ | —H | TQ | ethyl | ethyl | TQ | ethyl |

[1] X indicates the group is absent (such that $R_3$ and $R_{10}$ will be $CH_3$).

$I_{K+}$ represents binding to the linker L in the Formula above (e.g., to bind to a triazacryptand ionophoric moiety);

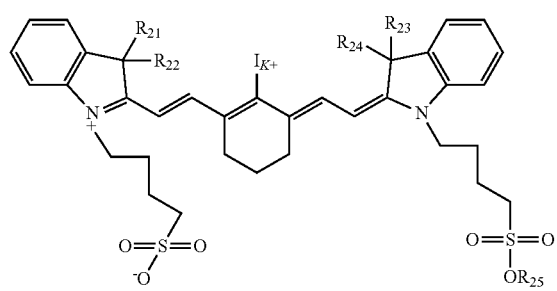

where:

each R ($R_{21}$, $R_{22}$, $R_{23}$, $R_{24}$, and $R_{25}$) is independently selected from H or lower alkyl, and $R_{25}$ is further independently selected from an alkali metal cation, n is an integer from 0 to 6 (i.e., 0, 1, 2, 3, 4, 5, or 6); and $I_{K+}$ represents binding to the linker L in the Formula above (e.g., to bind to a triazacryptand ionophoric moiety).

Other cyanine dyes bearing various substituents on the indole ring nitrogens, e.g., N-benzyl or N-phenyl, are also suitable.

The chromoionophores of the invention can be provided as any suitable salt, usually a halide salt, more usually a pharmaceutically acceptable salt, including halide salts such as a chloride salt, perchlorate salt, and the like. For example, the chromoionophores of the invention can form zwitterionic or

[2] DQ indicates a fused quinolizine ring structure:

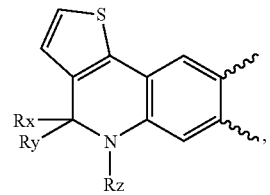

which structure is composed of $R_2$, $R_3$, $R_6$, and $R_7$ or composed of $R_8$, $R_9$, $R_{10}$, and $R_{13}$, as indicated. Where $R_2$, $R_3$, $R_6$, and $R_7$ are present as DQ, then $R_4$ and $R_5$ are absent, as indicated by "X" in the table above. Where $R_8$, $R_9$, $R_{10}$, and $R_{13}$ are present as DQ, then $R_{11}$ and $R_{12}$ are absent, as indicated by "X".

[3.] TQ indicates the structure:

in which $R_{10}$ and $R_{13}$, or $R_2$ and $R_3$, are fused to provide a thieno-quinoline ring and wherein $R_x$, $R_y$, and $R_z$ are $R_4$, $R_5$, and $R_6$, respectively, or $R_9$, $R_{11}$, and $R_{12}$, respectively.

Exemplary chromoionophores taken from a combination of Formula I and Formulae IIb, IIc, and IId, exemplified by their chloride salts, include those illustrated below:
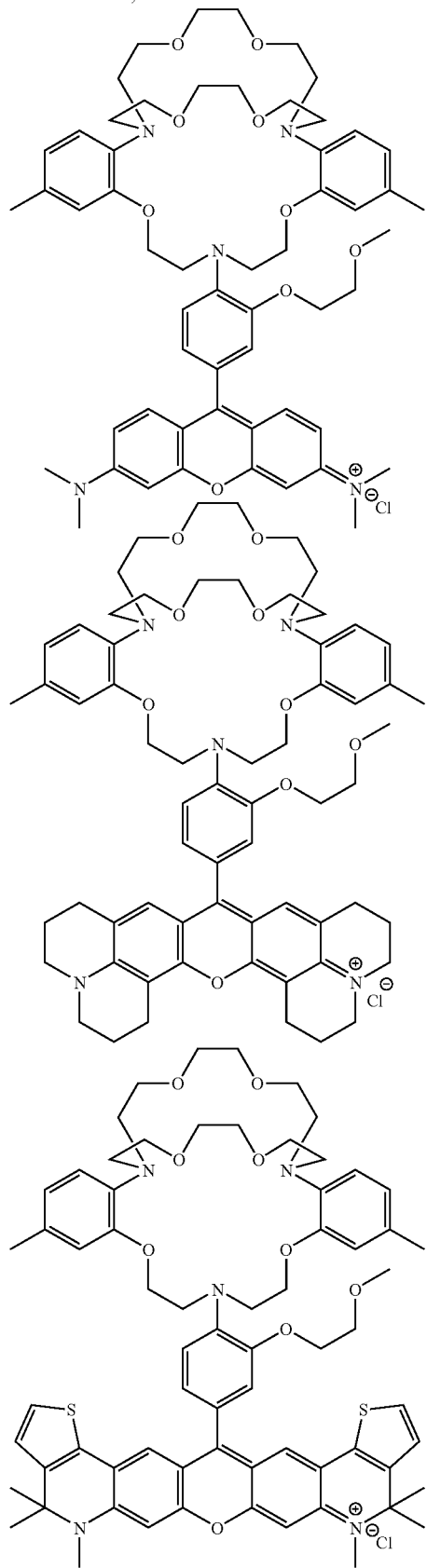
-continued
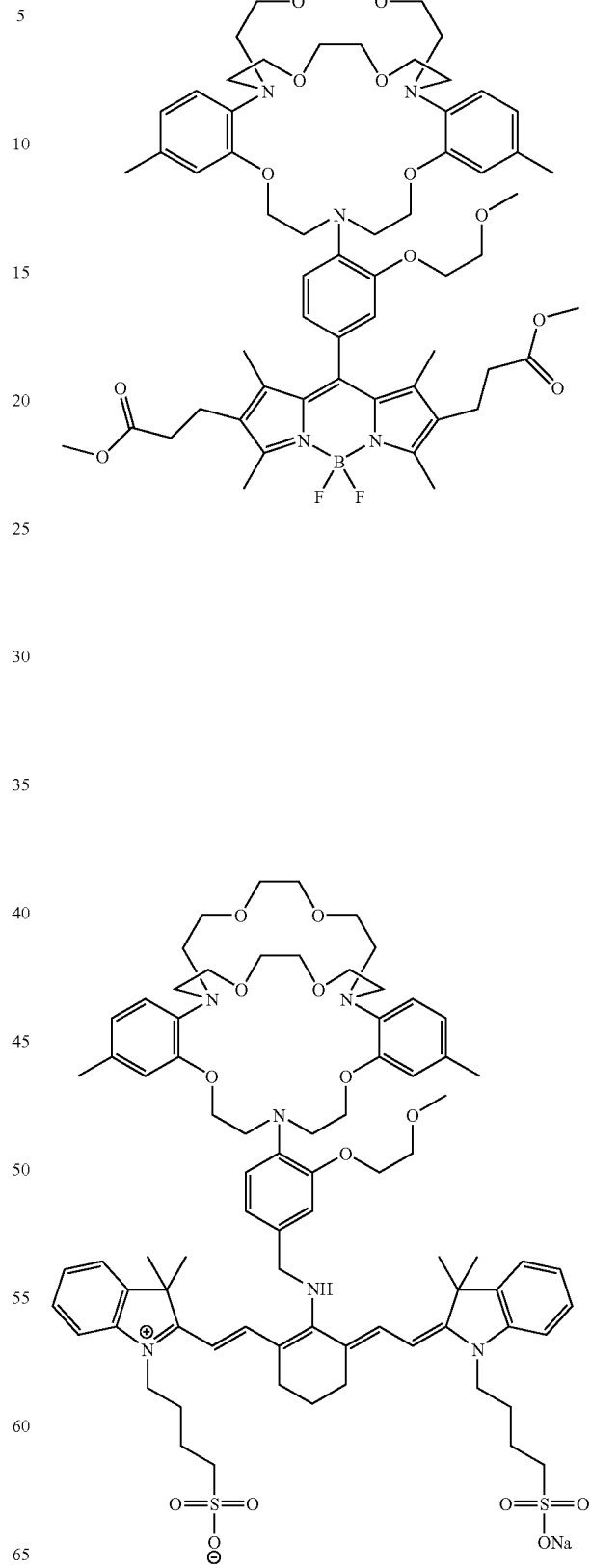

Chromoionophores Having Two Chromophores Conjugated to an Ionophore ("Dual Wavelength Chromoionophores")

In another aspect, the invention provides chromoionophores having an ionophore covalently bound through a "linker" to two different chromophores (e.g., two fluorophores or luminiphores, usually fluorophores). Such chromoionophores of the invention are represented by Formula A1 above, where the $F_2$ is present.

In addition to the characteristics described above with respect to potassium binding under physiological conditions, sodium and pH insensitivity, long excitation wavelength, and the like, such chromoionophores have two chromophores also provide for two distinguishable detectable signals.

Specifically, these double chromophore conjugates can provide for a first detectable signal that is sensitive to potassium binding to the ionophore portion of the conjugate, and a second detectable signal that is substantially insensitive to potassium concentrations. "Sensitive to potassium binding" as used here means that a detectable signal of the chromophoric moiety is modulated, usually increased in intensity, when potassium is bound to the TAC ionophoric moiety. "Insensitive to potassium binding" as used here means that a detectable signal of the chromophoric moiety is not significantly modulated, i.e., either increased or decreased, when potassium is bound to the TAC ionophoric moiety. Such conjugates, which may be referred to as "dual wavelength chromophores" or "dual wavelength potassium indicators", can be used to determine an absolute value of potassium in biological systems.

In general, the chromophores of dual wavelength conjugates are selected so as to provide for distinguishably different emission spectra to facilitate detection of a distinct signal from each of the two dyes (e.g., through use of different filters in the imaging system), which distinct signals can be used as an internal control signal and "test" signal. For example, analysis of the ratio of fluorescence intensity of the first detectable signal to the fluorescence intensity of the second detectable signal can be used to assess the potassium concentration. For example, where the first chromophore is a red dye (e.g., rhodamine) and the second chromophore is a green dye (e.g., BODIPY), then the dual wavelength chromoionophore can be provided such that an increase in fluorescence intensity in the red region is indicative of an increase in potassium, while the intensity of green fluorescence remains substantially unchanged or, if changed, serves as a baseline by which the red fluorescence signal is calibrated.

In general, in most embodiments of the dual wavelength chromoionophores of the invention water solubility is provided or enhanced by including a water soluble polymer in the conjugate (e.g., dextran).

In general, dual wavelength chromoionophores of the invention can be described by the general formula of A1 above. Further exemplary embodiments, and further details of the dual wavelength chromoionophores of the invention are described below in more detail.

Generally, the ionophoric moiety and two different chromophoric moieties are provided as a branched structure, which are covalently joined by an amide group (which may be referred to herein as a central amide linker). Each of the chromophoric moieties (referred to herein as "dyes" for convenience) can be joined to the central amide linker by an additional linker. Usually at least one of the arms of the conjugate includes a water soluble polymer, which is positioned between the dye and its linker. Dual wavelength chromoionophores of the invention may thus be described by the general formula:

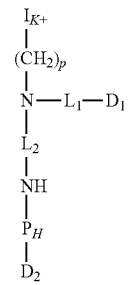

(III)

where
$I_{K+}$ is a triazacryptand (TAC) ionophoric moiety, usually a triazacryptand ionophoric moiety of Formula IV below:
—$(CH_2)_p$— is exemplary of a linker "L" in Formula A1 above, where p is 0, 1 or 2, usually 1 or 2;
$L_1$ is a first "linker", which can be a substituted or unsubstituted aryl group, usually a substituted phenyl group, which is coupled to a chromophore $D_1$ (e.g., such as a xanthylium to construct a rhodamine unit as exemplified in FIG. 18).
$L_2$ is a second "linker", which can be a substituted or unsubstituted aryl group, usually an unsubstituted phenyl group or —CO—$(CH_2)$—COO-t-butyl or derivative thereof (e.g., where t-butyl group is cleaved to produce an acid for generation of amide linkage with amino-dextran-linked green dye for $D_2$);
$P_H$ is a water soluble polymer, such as dextran, polyethylene oxide, polylactide, polyglycolide, and polyethyleneimine where $L_2$ and $P_H$ are covalently bound through an amide linkage.

$D_1$ and $D_2$ are different chromophoric moieties having detectably distinct emission wavelengths, e.g., such that, for example, $D_1$ provides an emission wavelength in the "red" range and $D_2$ provides an emission wavelength in the "green" range. $D_1$ is selected to be sensitive to binding of potassium to the ionophoric moiety, such that detectable signal the dye which will be modulated in emission intensity according to whether the ionophoric moiety is bound (increase intensity) or unbound (decreased intensity) by potassium. $D_2$ is selected to be a potassium insensitive dye and vice versa. $L_1$ is generally selected so as to maintain potassium sensitivity of $D_1$, e.g., by selection of a moiety that provides for electron transfer to the dye, and can be, for example, a single covalent bond attached to TMR (see, e.g., FIG. 18).

In an exemplary embodiment, dual wavelength chromoionophores of the invention are described by the formula:

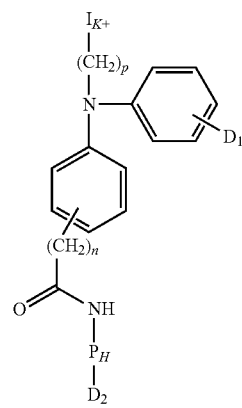

(IIIa)

where $I_{K+}$ is a triazacryptand (TAC) ionophoric moiety, usually a triazacryptand ionophoric moiety, e.g., as set out in Formula IV below;

n is 0, 1, 2, 3, 4 or more, usually at least 3 or 4;

p is 1, or 2, the phenyl groups joined at the central amine serve as the "linkers" $L_1$ (e.g. for the attachment of a potassium sensitive dye (e.g., red dye)) and $L_2$ (e.g., for attachment of a potassium insensitive dye (e.g., green dye)) in Formula III, where the dye-containing moieties are independently positioned para or meta to the central amine, with each of the dye-containing moieties usually being positioned para to the central amine;

$P_H$ is a hydrophilic, water soluble polymer, such as dextran and other polymers exemplified in the formulae above, where $P_H$ is covalently bound to the phenyl linker through a nitrogen of an amide group;

$D_1$ and $D_2$ are different chromophoric moieties as described above, where $D_1$ is sensitive to potassium binding by the TAC ionophoric moiety, and $D_2$ is substantially insensitive to potassium binding by the TAC ionophoric moiety.

In another embodiment, dual wavelength chromoionophores of the invention may also be described by the general formula (IIIb):

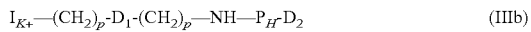
(IIIb)

where $I_{K+}$ is a triazacryptand (TAC) ionophoric moiety, usually a triazacryptand ionophoric moiety of Formula IV below;

—$(CH_2)_p$— is exemplary of a linker "L" in Formula A1 above, where p is 0, 1 or 2;

$P_H$ is a hydrophilic, water soluble polymer, such as dextran and other polymers exemplified in the formulae above, where $P_H$ is covalently bound to the $(CH_2)_p$ linker through a nitrogen of an amide group;

$D_1$ and $D_2$ are different chromophoric moieties as described above, where $D_1$ is sensitive to potassium binding by the TAC ionophoric moiety, and $D_2$ is substantially insensitive to potassium binding by the TAC ionophoric moiety.

The components of dual wavelength chromoionophores of the invention are described in more detail below.

Potassium-Binding Ionophoric Moieties for Use in Dual-Wavelength Chromoionophores The dual wavelength chromoionophores of the invention generally include a potassium-binding triazacryptand ("TAC") ionophoric moiety as described for the single wavelength conjugates described above. In general, the TAC ionophoric moiety is any suitable potassium-binding TAC moiety that can provide for the desired characteristics of the dual wavelength conjugates of the invention (e.g., potassium selectivity, sodium and pH insensitivity, etc.). Exemplary TAC ionophores are described in, for example, U.S. Pat. No. 6,211,359. Of particular interest is the TAC ionophore of the chromoionophore of the invention is of the general Formula I, as described above. TAC ionophores of particular interest can also be described according to Formula (IV) as follows:

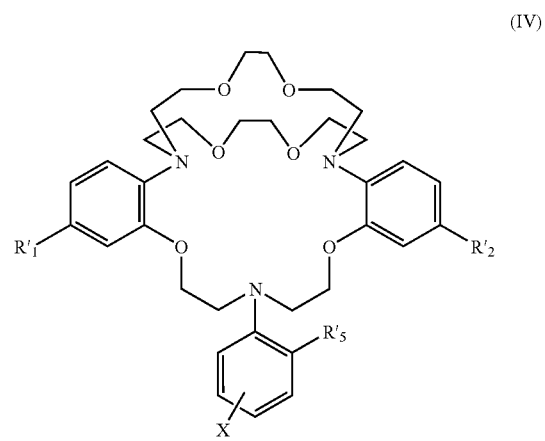
(IV)

where: $R'_1$, $R'_2$ are independently a lower alkyl, are usually the same, and are preferably methyl;

$R'_5$ is a substituted or unsubstituted alkyl (e.g. lower alkyl), alkoxy (e.g. lower alkoxy), alkoxyalkoxy, alkoxyaryl, t-alkylester (e.g. t-butyl ester of carboxyloweralkoxy, t-alkylester of carboxyalkoxyalkoxy, succinimidylester of carboxyalkoxy, succinimidylester of carboxyalkoxyalkoxy, aminoalkoxy, aminoalkoxyalkoxy, mercaptoalkoxy, or mercaptoalkoxyalkoxy, whee exemplary $R'_5$ groups include

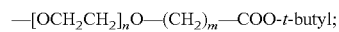

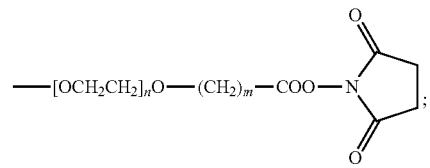

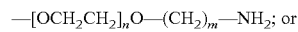

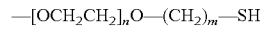

where n is 1 m is an integer from 0 to 6 (i.e., 0, 1, 2, 3, 4, 5, or 6); and

X represents the position of at which the TAC ionophoric moiety is bound to the dual wavelength conjugate, usually through a single covalent bond or an alkyl linker to a tertiary amine, as set out in Formulae III and IIIa above, and may be in the para or meta position, usually the para position, relative to the amine substituent.

In embodiments of specific interest, the ionophore of the chromoionophore is of the formula:

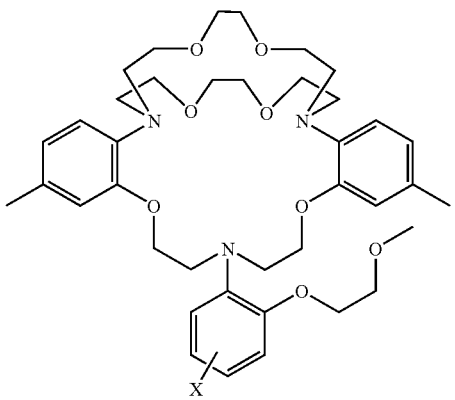

(IVa)

where X is as defined above in Formula IV, and may be in the para or meta position, usually the para position, relative to the amine substituent.

Chromophoric Moieties for Use in Dual Wavelength Chromoionophores of the Invention The chromophoric moieties of the dual wavelength chromoionophores of the invention can be any suitable chromophore, including those described above for single wavelength chromoionophores of the invention. Suitable chromophores are known in the art.

As discussed, the potassium-binding sensitive chromophoric moiety and the potassium-binding insensitive chromophoric moiety(ies) should be selected so that the detectable signal elicited from the potassium binding-insensitive chromophoric moiety(ies) in the absence of potassium (or below the threshold of potassium sensitivity of the ionophoric moiety) is different from a detectable signal from the potassium-binding sensitive chromophoric moiety. In this way the potassium binding-insensitive chromophoric moiety(ies) can serve as a reference or internal control in determining potassium levels, and can also confirm the presence (qualitatively or quantitatively) of the chromoionophore.

In specific embodiments, the subject compounds are generally described by Formula V as follows:

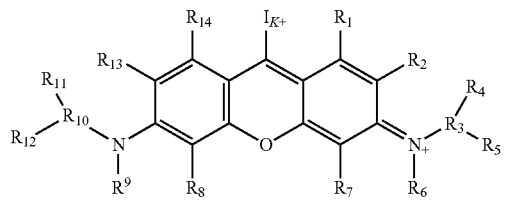

(V)

where $I_{K+}$ represents a covalent linkage to construct dual wavelength chromoionophore of the invention as represented in the formulae above such that the chromophore of Formula V, is $D_1$ in Formula III or is $F_1$ in Formula A1 above;

$R_1$ and $R_{14}$ are each independently selected from H or a lower alkyl, and are each generally the same, and usually are H or methyl, usually H;

$R_2$ and $R_{13}$ are each independently selected from H or a lower alkyl, and are each generally the same, and usually are H or methyl, and usually are H, unless:

$R_2$ and $R_{13}$ are joined to form quinolizine ring systems that include $R_3$, $R_6$, and $R_7$, and $R_8$, $R_9$, and $R_{10}$, respectively, to provide one or two substituted or unsubstituted, usually unsubstituted, quinolizine ring systems in the compound; or $R_2$ and $R_{13}$ are joined to form in the compound pyridine or thieno-pyridine ring systems that include $R_3$ and $R_{10}$, respectively, to provide one or two pyridine ring systems or one or two thieno-pyridine ring systems in the compound, and wherein the thieno-pyridine ring systems are thieno-quinoline ring systems;

wherein when $R_2$ and $R_{13}$ are present in ring structures, at least one of the ring structures contains a positively charged amine, and when $R_2$ and $R_{13}$ are joined to form one or two pyridine ring systems that include $R_3$ and $R_{10}$, respectively, the pyridine ring systems are substituted by a methylene or polymethylene group that is substituted by an anionic moiety, e.g. —$CH_2SO_3^-$;

where $R_2$ and $R_{13}$ when present in ring structures usually form the same ring structures with the proviso that the ring structure including $R_{13}$ contains a positively charged amine as set out in Formula II above;

$R_4$, $R_5$ $R_{11}$, and $R_{12}$ are independently selected from H or a lower alkyl (usually methyl), may be the same moieties, and are present when $R_2$ and $R_{13}$ are joined in a ring structure with $R_3$ and $R_{10}$, respectively, (or, stated differently, when "N" is part of a ring structure), particularly when the ring structure is a thieno-pyridine structure (to provide one or two thieno-quinoline ring systems in the compound, in which $R_4$, $R_5$, $R_{11}$, and $R_{12}$ are usually methyl), otherwise $R_4$, $R_5$ $R_{11}$, and $R_{12}$ are absent;

$R_3$, $R_6$, $R_9$, and $R_{10}$ are independently selected from a lower alkyl, usually methyl, if "N" is not part of a ring structure; and $R_7$ and $R_8$ are independently selected from H or a lower alkyl if $R_7$ and $R_8$ are not part of a ring structure with $R_6$ and $R_9$, respectively.

In another embodiment, the chromophoric moiety is represented by the formula:

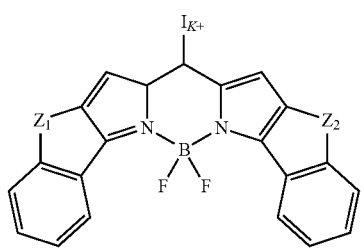

(VI)

where $I_{K+}$ represents a covalent attachment to construct the dual wavelength chromoionophore of the invention, as represented in the formulae above such that the chromophore of Formula VI, $D_1$ in Formula III or is $F_1$ in Formula A1 above; and $Z_1$ and $Z_2$ are O or S, usually O.

In another embodiment, the chromophoric moiety is represented by the formula:

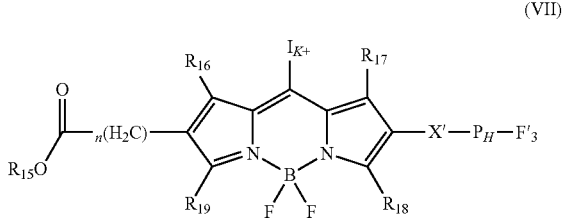

(VII)

where $I_{K+}$ represents a covalent attachment to construct a dual wavelength chromoionophore of the invention, as represented in the formulae above such that the chromophore of Formula VII, is $D_1$ in Formula IIIb or is $F_1$ in Formula A1 above; and each R ($R_{15}$, $R_{16}$, $R_{17}$, $R_{18}$, and $R_{19}$) is independently selected from H or lower alkyl, usually methyl, and when attached to an oxygen atom of the carboxyl group ($R_{15}$), R is further independently selected from an alkali metal cation, usually a $Na^+$ or $Li^+$ cation; and n is an integer from 0 to 6 (i.e., 0, 1, 2, 3, 4, 5, or 6), usually 2; X' is a reactive group, selected from an amine, amide, succinimidyl ester, or aldehyde, $P_H$ is selected from a hydrophilic, water-soluble polymer; and $F'_3$ is a chromophoric moiety insensitive to pH and to potassium binding by the chromoionophore, where $F'_3$ provides a detectable signal that is different from a detectable signal of $F_1$.

In one embodiment of particular interest, D1 of Formula III or IIIa is provided by the dye of Formula V or Formula VI and D2 of Formula III or IIIa is provided by the green BODIPY dye which will be potassium insensitive. In an alternative embodiment, $D_1$ of Formula III or IIIa is provided by the dye of Formula VI.

The chromoionophores of the invention can be provided as any suitable salt, usually a halide salt, more usually a pharmaceutically acceptable salt, including halide salts such as a chloride salt.

In specific exemplary embodiments, chromoionophores taken from a combination of Formulae IV, V, VI, and VII include:

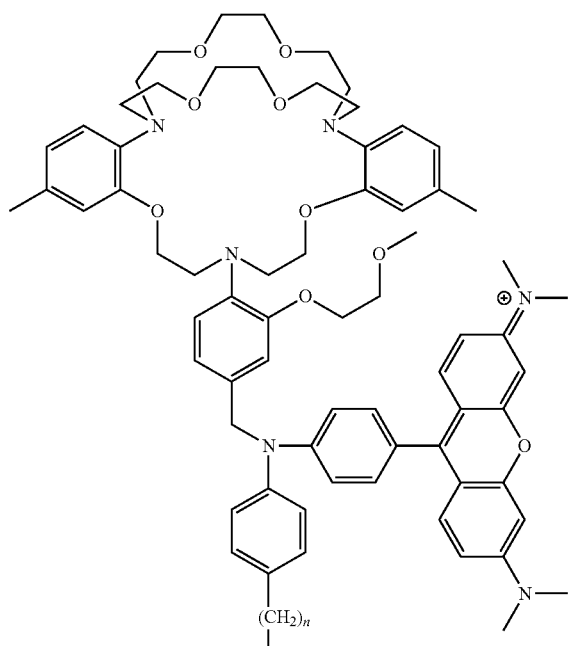

(VIII)

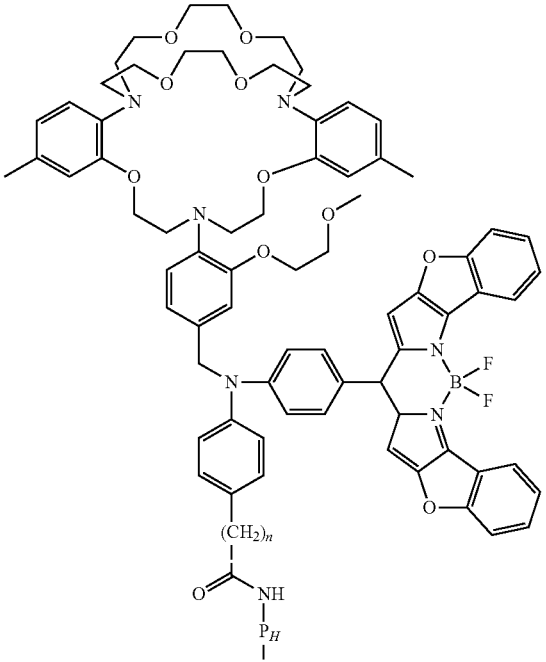

(IX)

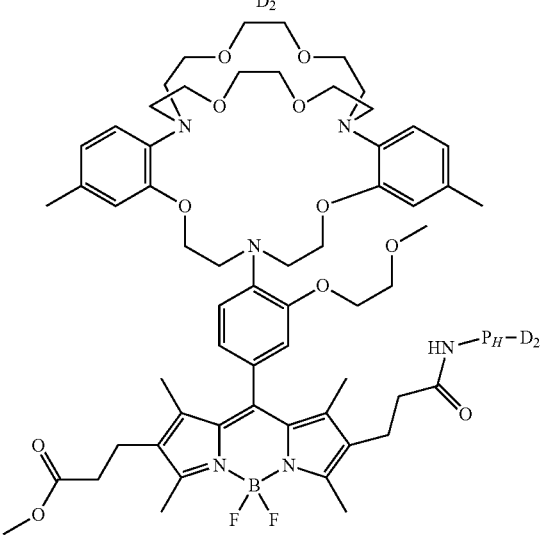

where n is 0, 1, 2, 3, 4 or more, usually 0, 1, 2, 3, or 4, at least 3 or 4; and $P_H$ is a water soluble polymer and $D_2$ is a chromophore different from the chromophore at position $D_1$ and with a detectably different emission wavelength. For example, $D_2$ in Formula VIII can be a green dye (e.g., BODIPY or green rhodamine, preferably BODIPY), and D2 in formula X can be a red dye (e.g., tetramethylrhodamine).

Water-Soluble Polymers for Use in Dual-Wavelength Chromoionophores

The water soluble polymer ($P_H$ in the Formulae above) can be any suitable polymer which, when included in a chromoionophore conjugate of the invention, provides for enhanced water solubility of the conjugate. Exemplary water soluble polymers include dextran, polyethylene oxide, polylactide, polyglycolide, PLGA, PEI, and the like.

Kits

Kits with the subject chromoionophore compounds of the invention, which may be provided in a container or vial (preferably sterile), and may be further provided in physiologically compatible solutions, preferably pharmaceutically acceptable solutions, for use as indicators in methods of assessing potassium concentrations, e.g., as described below. In such kits, in addition to the containers containing the solutions of the compounds, the kit can include an informational package insert describing the methods for using the inventive chromoionophores for the in vivo and in vitro determination of $K^+$ concentrations.

Methods of Use

The chromoionophores of the invention find use in a variety of applications, including in vivo and in situ applications, as well as in in vitro applications, particularly those involving biological samples that are provided in conditions mimicking physiological conditions. In general, the chromoionophores of the invention can be used to assess potassium concentrations with the proviso that the sample in which potassium concentration is to be assessed is one in which a chromoionophore can be accumulated at a concentration sufficient to allow for detection of a signal or change in signal associated with potassium concentrations or change in potassium concentrations (e.g., by fluorescence microscopy). The methods described herein can be carried out to provide a qualitative or quantitative assessment of potassium ion concentrations.

Methods for $[K^+]_o$ Measurements in a Biological Compartments

The chromoionophores of the invention can be used to assess potassium concentrations, as well as changes in potassium concentrations over a selected period of time, in a biological compartments which define an extracellular fluid compartment, which may be present in vivo or, as in the case of an organ culture, in situ. In embodiments of particular interest, chromoionophores of the invention are used for high-throughput screening to detect potassium efflux from cells to identify, for example, small molecule inhibitors of potassium channels or potassium-coupled transporters.

As discussed above, the chromoionophores of the invention are particularly suitable for such applications, since the long-wavelength excitation (about 500 nm or greater) and bright fluorescence minimizes background cellular fluorescence, interference by hemoglobin oxygenation, light-induced injury of tissues, and photobleaching. The chromoionophores of the invention are also water soluble and membrane impermeant, providing for assessment of extracellular potassium concentrations independent of intracellular potassium concentrations.

In general, in this aspect the invention provides a method of assessing a potassium concentration in a biological compartment, e.g., an extracellular fluid compartment, where the method involves introducing a chromoionophore of the invention into an extracellular fluid compartment of an organ or tissue, and assessing the potassium concentration in the compartment. In some embodiments, the methods further involve subjecting the organ or tissue to a stimulus or agent (e.g., a candidate agent), and assessing the potassium concentration, where a change in potassium concentration in the presence of the stimulus or agent as compared to a potassium concentration in the absence of the stimulus indicates the stimulus modulates extracellular potassium concentrations (e.g., affects potassium transport across cells into (or out of) the extracellular space.

The chromoionophores of the invention are for potassium measurements in many types of biological compartments. In one embodiment, the biological compartment is an extracellular fluid compartment. Extracellular fluid compartments can occur naturally, or can be provided (e.g., by application of, for example, a tourniquet, or through surgery (e.g., in a non-human animal)). Extracellular fluid compartments of a biological compartment include, for example, any space of an organ which is defined by an overlying tissue structure (e.g., as with the brain cortex and the pericardium), and, where assessment over a period of time is desired, are areas in which flow of physiological fluids (e.g., blood, lymph, CSF, etc.) is sufficiently slow (or can be made to be sufficiently slow) such that potassium levels can be assessed over a desired period of time.

Exemplary extracellular fluid compartments (e.g., which may be naturally defined by a biological compartment or can be made by modification of tissues) include those of the central nervous system (e.g., brain cortex, brain ventricle, and the like; epidural space; and the like; spaces which can be created in the brain or spine which are sufficiently stagnate with respect to cerebrospinal fluid (CSF) turnover; and the like), heart (e.g., epidural space, pericardial space, and the like); skeletal or smooth muscle (especially skeletal muscle); kidney (e.g., the space defined by the kidney capsule and renal cortex); ovaries; testicles; pancreas; lymph nodes; blood; pancreas; lung (e.g., pleural space); joint capsules; and the like.

Biological compartments also include compartments in solid organs (e.g., kidney) that define a space outside cells, and may contain extracellular matrix.

Methods for delivery of an agent to an extracellular fluid compartment (including those naturally defined by a biological compartment, or provided artificially) are known in the art, and can be readily adapted for use with the chromoionophores of the invention. In some embodiments it may be desirable to provide the chromoionophore in a solution including a sample of the extracellular fluid found in the extracellular fluid compartment into which the chromoionophore is to be introduced. Methods for assessing changes in a detectable signal, such as that provided by the chromoionophores of the invention, in the context of such extracellular fluid compartments are also known in the art and can be readily adapted for use with the chromoionophores of the invention.

The methods of the invention can be used in, for example, intraoperative potassium mapping in a subject (e.g., in a human subject) having a seizure (e.g., an epileptic seizure), undergoing neurosurgery, or other situations in which assessment of potassium levels in a subject are of interest in the context of diagnosis or therapy.

In general, the long excitation wavelength of the chromoionophores of the invention can be used in minimally invasive or non-invasive procedures following delivery of the chromoionophore to a tissue of interest. For example, the chromoionophores of the invention can be introduced into a biological compartment of the brain, and imaging of potassium concentrations and changes in potassium concentrations accomplished through the intact skull.

Methods for $[K^+]_o$ Measurements In Vitro

Assessment of potassium concentrations, and particularly changes in potassium concentrations, can also be assessed in vitro. For example, the chromoionophores of the invention can be used in connected with assessing potassium levels in an extracellular fluid space of a cultured organ. In another example, the chromoionophores of the invention can be used in connection with other biological samples, including samples that contain cells which may effects a change in potassium concentrations in culture medium (e.g., in response to an agent or other stimulus). In a further example, the chromoionophores of the invention can be used as sensors of potassium or changes in potassium concentrations in a biological sample, e.g., to sense blood potassium levels in a patient.

For example, changes in potassium levels in a culture of cells (e.g., immune cells, e.g., leukocytes, lymphocyte, monocytes (e.g., macrophages), and the like; muscle cells (e.g., cardiomyocytes); and the like) can be assessed by including a chromoionophore of the invention in the culture medium. The cell culture is then contacted with a stimulus or an agent (e.g., a candidate agent, as described in more detail below), and the effect upon potassium in the culture medium assessed. A change in potassium concentration in the presence of the stimulus or agent as compared to a potassium concentration in the absence of the stimulus or agent indicates the stimulus or agent modulates extracellular potassium concentrations (e.g., affects potassium transport across cells into (or out of) the culture medium. The invention also contemplates methods in which cells are first washed to deplete extracellular potassium, and then culture medium containing a chromoionophore of the invention added to the washed cells. Extracellular potassium can then be monitored by following accumulation of potassium in the culture medium.

Methods for assessing changes in a detectable signal, such as that provided by the chromoionophores of the invention, in the context of in vitro assays as described herein, are known in the art and can be readily adapted for use with the methods using the chromoionophores of the invention.

The chromoionophores of the invention can also be used in connection with a support on which the chromoionophore is immobilized. For example, the chromoionophore can be attached covalently to an appropriately modified glass surface or non-covalently by depositing the compound onto the surface with appropriate solvents Methods for accomplishing immobilization of a compound to a surface suitable for use with the present invention are known in the art and can be readily adapted to the present invention.

For example, a chromoionophore of the invention can be immobilized on a tip of a fiberoptic sensor so that the changes in intensity of the detectable signal(s) of the chromoionophore can be detected (e.g., a detectable signal of a single wavelength chromoionophore of the invention, or the two different detectable signals of the dual wavelength chromoionophores of the invention). This embodiment finds particular use in connection with fiberoptic endoscopes, where the endoscope can be inserted into a body cavity or passageway, and the presence or absence of a detectable signal(s) generated by the immobilized chromoionophore in response to potassium concentrations in the extracellular space detected using the fiberoptic system.

Another embodiment, the chromoionophore is immobilized on a support which present in a system for analysis of potassium concentration in a sample. In general, such systems are used by contacting a sample with the surface of the support on which the chromoionophore is immobilized, and detecting the presence or absence of a detectable signal(s) of the chromoionophore. The presence or absence of the detectable signal(s), as well as the intensity of the detectable signal(s), is indicative of the concentration of potassium in the sample. Exemplary systems contemplated in this aspect of the invention include microfluidic devices, such as may be useful in high throughput analysis of samples.

As will be appreciated, the methods can also be readily adapted to assess changes in extracellular potassium levels over a period of time. In general, such methods involve assessing an extracellular potassium concentration at a first time point and at a later second time point, and determining the change in concentration (e.g., such that a higher potassium concentration at the second time point relative to the first time point is indicative of an increase in extracellular potassium concentration during the period between the second and first time points, and a lower potassium concentration at the second time point relative to the first time point is indicative of a decrease in extracellular potassium concentration during the period between the second and first time points). In these embodiments, the time period over which a change in extracellular potassium concentrations is assessed can vary, and can be on the order of milliseconds (ms) (e.g., 1 ms, 5 ms, 10 ms, 50 ms, 100 ms, etc.), a few seconds (e.g., 4 sec, 6 sec, 12 sec, 24 sec, 30 sec, 45 sec, etc.), a few minutes (e.g., 1 min, 2 mins, 5 mins, 10 mins, etc.), or longer.

Methods of Use of Chromoionophores Involving Assessing the Effect of Candidate Agents Upon Potassium Exchange in a Cell or Tissue As discussed above, the chromoionophores of the invention find use in methods of screening candidate agents for activity in modulating extracellular potassium levels (i.e., increasing or decreasing extracellular potassium levels). Such screening methods can be used to, for example, identify modulators of potassium channels or potassium-coupled transporters. In general, an agent is identified as one having activity in increasing extracellular potassium levels where the agent provides for an at least transient increase in extracellular potassium concentration of at least about 10%, at least about 20%, at least about 40%, at least about 60%, at least about 80%, at least about 100%, at least about 150% or more, or at least about 10-fold or by at least about 20-fold, or more, as compared to controls. Similarly, an agent is identified as one having activity in causing a decrease in extracellular potassium levels (e.g., by causing an potassium influx into the cells or tissue or blocking the potassium efflux by inhibition of potassium channels) where the agent provides for an at least transient decrease in extracellular potassium concentration of at least about 10%, at least about 20%, at least about 40%, at least about 60%, at least about 80%, at least about 90% or more as compared to controls. By "transient" is meant that the change in potassium concentrations may occur over only a matter of seconds to minutes, and may return to a potassium concentration the same or similar to that prior to application of the stimulus or agent.

In general, the candidate agent is added to the biological sample before, with or after the chromoionophore is added. Changes in potassium concentrations can be observed over any desired period of time, with changes in potassium levels usually being detectable within a few seconds to a few minutes. However, the methods of the invention are not so limited, and can involve assessing changes in potassium concentrations over a longer period of timer, e.g., at least about 5 minutes, at least about 10 minutes, at least about 30 minutes, at least about 1 hr, at least about 2 hr, at least about 4 hr, at least about 8 hr, at least about 12 hr or at least about 24 hr or more after the method is initiated by providing the chromoionophore and candidate agent into contact with the cells or tissue.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents may be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidition, etc. to produce structural analogs.

The compounds and methods disclosed herein can be readily adapted to provide high throughput screening to identify modulators of any of a number of potassium channels or potassium-coupled transporters, of which numerous types are known in the art. The methods and compounds of the invention can be used to assess activity of potassium channels or potassium-coupled transporters that are endogenous to a cell (e.g., cultured cell) or tissue, or that are present as a result of expression from a recombinant construct present in the cell. In general, primary cell cultures, immortalized cell cultures, or tissues can be used in assays.

Potassium channels suitable for screening will be readily apparent and known to the ordinarily skilled artisan. In general, potassium channels are located in all or nearly all cell types, and may be regulated by voltage, ATP concentration, or second messengers such as $Ca^{2+}$ and cAMP. In non-excitable tissue, potassium channels are involved in protein synthesis, control of endocrine secretions, and the maintenance of osmotic equilibrium across membranes. In neurons and other excitable cells, in addition to regulating action potentials and repolarizing membranes, potassium channels are responsible for setting resting membrane potential.

Potassium channel subunits of the Shaker-like superfamily share a characteristic six transmembrane/1 pore domain structure. Four subunits combine as homo- or heterotetramers to form functional K channels. These pore-forming subunits also associate with various cytoplasmic b subunits that alter channel inactivation kinetics. The Shaker-like channel family includes the voltage-gated potassium channels as well as the delayed rectifier type channels such as the human ether-a-go-go related gene (HERG) associated with long QT, a cardiac dysrythmia syndrome (Curran, M. E. (1998) Curr. Opin. Biotechnol. 9:565-572; Kaczorowski, G. J. and M. L. Garcia (1999) Curr. Opin. Chem. Biol. 3:448-458).

A second superfamily of potassium channels is composed of the inward rectifying channels (Kir). Kir channels have the property of preferentially conducting $K^+$ currents in the inward direction. These proteins are composed of a potassium selective pore domain and two transmembrane domains, which correspond to the fifth and sixth transmembrane domains of voltage-gated potassium channels. Kir subunits also associate as tetramers. The Kir family includes ROMK1, mutations in which lead to Bartter syndrome, a renal tubular disorder. Kir channels are also involved in regulation of cardiac pacemaker activity, seizures and epilepsy, and insulin regulation.

The TWIK potassium channel family includes the mammalian TWIK-1, TREK-1 and TASK proteins. Members of this family possess an overall structure with four transmembrane domains and two P domains.

Further exemplary potassium channels are described US 2006/0216690 and US 2006/0216689. The table below provides a summary of exemplary potassium channels and channel subtypes.

| Channel Type | Sub-type/Alternate names | Accession No. | Reference |
|---|---|---|---|
| ATP regulated | rKir1.1 (ROMK1)(rat) | U12541 | US 5,356,775 |
| | hKir1.1 (ROMK1)(human) | | US 5,882,873 |
| | Kir1.2 | U73191 | |
| | Kir1.3 | U73193 | |
| II. | β-cell | | US 5,744,594 |
| III. | hβIR | | US 5,917,027 |
| IV. | HuK$_{ATP}$-1 | | EP 0768 379 |
| Constitutively Active | Kir2.1 (IRK1) | U12507 | US 5,492,825 |
| | | | US 5,670,335 |
| | Kir2.2 | X78461 | |
| | Kir2.3 | U07364 | |
| G-protein Regulated | Kir3.1 (GIK1, KGA) | U01071 | US 5,728,535 |
| | Kir3.2 | U11859 | US 5,734,021 |
| | Kir3.3 | U11869 | US 5,744,324 |
| | Kir3.4 (CIR) | X83584 | US 5,747,278 |
| | Kir4.1 (BIR10) | X83585 | |
| | Kir5.1 (BIR9) | X83581 | |
| | Kir6.1 | D42145 | |
| | Kir6.2 | D5081 | |
| | Kir7.1 | | EP 0 922 763 |
| Voltage Regulated | | | |
| KCNA1 | hKv1.1 (RCK1, RBK1, MBK1, MK1, HuK1) | L02750 | |
| KCNA2 | Kv1.2 (RBK2, RBK5, NGK1, HuKIV) | | |
| KCNA3 | Kv1.3 (KV3, RGK5, HuKIII, HPCN3) | | |
| KCNA4 | Kv1.4 (RCK4, RHK1, HuKII) | | |
| KCNA5 | Kv1.5 (KV1, HPCN1, HK2) | | |

-continued

| Channel Type | Sub-type/Alternate names | Accession No. | Reference |
|---|---|---|---|
| KCNA6 | Kv1.6 (KV2, RCK2, HBK2) | | |
| KCNA7 | Kv1.7 (MK6, RK6, HaK6) | | US 5,559,009 |
| Kv2 (Shab) | | | |
| KCNB1 | Kv2.1 (DRK1, mShab) | M64228 | |
| KCNB2 | Ky2.2 (CDRK1) | | |
| | K channel 2 | | US 5,710,019 |
| Kv3 (Shaw) | | | |
| KCNC1 | Ky3.1 (NGK2) | | |
| KCNC2 | Ky3.2 (RKShIIIA) | X60796 | |
| KCNC3 | Kv3.3 (KShIIID) | | |
| KCNC4 | Kv3.4 (Raw 3) | | |
| Kv4 (Shal) | | | |
| KCND1 | Kv4.1 (mShal, KSh1VA) | M64226 | |
| KCND2 | Kv4.2 (RK5, Rat Shal 1) | | |
| KCND3 | Kv4.3 (KShIVB) | | |
| | hKv5.1 (IK8) | | WO 99/41372 |
| | Kv6.1 (K13) | | |
| | Kv7 | | |
| | Kv8.1 | | |
| | Kv9 | | |
| Delayed Rectifier | KvLQT1 | AF000571 | US 5,599,673 |
| | HERG (erg) | U04270 | WO 99/20760 |
| Calcium regulated | | | |
| $Ca^{2+}$ Regulated - Big | BKCa (hSLO) | U11717 | |
| | HBKb3 (β-subunit) | | WO/99/42575 |
| | Maxi-K | | US 5,776,734 |
| | | | US 5,637, 470 |
| $Ca^{2+}$ Regulated Small | | | |
| KCNN1 | SKCa1 | U69883 | |
| KCNN2 | SKCa2 | U69882 | |
| KCNN3 | SKCa3 | U69884 | |
| KCKN4 | SKCa4 (1KCal) | | Muscle Nerve 1999 22(6): 742-50 |
| | TWIK1 | U33632 | |

Use of Dual Wavelength Chromoionophores of the Invention in Determination of Absolute Potassium Concentration The dual wavelength chromoionophores of the invention provide two detectable signals—one that is sensitive to potassium binding by the ionophore and one that is insensitive to potassium binding. Such chromoionophores provide the ability to determine the absolute potassium concentration in an environment of interest (in vitro or in vivo). The detectable signals from each of the chromophores (e.g., detection and measurement of intensity of fluorescence at the two colors) can be performed either simultaneously in a microscope (e.g., using beamsplitters and dual cameras or equivalent) or serially (e.g., using rapid filter changing systems). The ratio of the two signals (after background is subtracted, e.g., from an unstained sample) is computed, and the ratio used to determine absolute potassium concentration. A separate general calibration of signal ratio vs. potassium concentration is generated to allow determination of potassium concentration from signal ratio.

Variations of the methods of the invention using the chromoionophores of the invention will be readily appreciated by the ordinarily skilled artisan, and are contemplated by the present invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods and materials are used in the examples below.

TAC-Red $[K^+]_o$ measurements in brain cortex. Wildtype and AQP4 null mice in a CD1 genetic background (30-35 g body weight/age 10-12 weeks) were used (described in Ma et al. Ma et al. *J. Clin. Invest.* 100, 957-962 (1997)). These mice are phenotypically normal at baseline and have normal brain architecture; however they manifest altered brain swelling in response to cytotoxic and vasogenic forms of edema. Mice were anesthetized with 2,2,2-tribromoethanol (125 mg/kg, intraperitoneal (ip)) and the head was immobilized in a standard mouse stereotactic frame. Body temperature was maintained at 36-37° C. using a heating pad. The skull was exposed by a midline skin incision. A 2.7 mm diameter circular area of the thin, semi-translucent skull bone located 0.5 mm lateral to the midline and 1 mm posterior to the bregma was removed using a microdrill under microscope to expose intact dura with underlying brain. A separate small burr hole (0.8 mm diameter) used to initiate cortical spreading depression was made 2 mm posterior to the edge of the larger craniectomy. The skin flaps of the lager craniectomy were held open with a cylindrical dam to create a pocket for dye loading.

The ECS was dye-stained by 5 min incubation with aCSF (in mM: NaCl, 145; KCl, 4; $MgCl_2$, 1; $CaCl_2$, 2.5; $KH_2PO_4$, 1; glucose, 10; pH 7.4) containing about 50 μM TAC-Red. After loading, the dural surface was washed with dye-free aCSF, the skin flaps were removed, and the stereotactic frame was transferred to the stage of a Nikon SMZ1500 stereo epifluorescence microscope. Freshly cut brain slices showed TAC-Red staining down to >500 μm beneath the brain surface.

Fluorescence was measured using a 1.6× objective lens (working distance 24 mm, numerical aperture 0.21), and custom filter set for TAC-Red (HQ, Chroma). The illumination source was X-cite 120 light source with neutral density filters placed to eliminate photobleaching. Fluorescence was imaged using a 14-bit 1024×1024 pixel cooled CCD camera (CoolSnap HQ, Photometrics). Generally full-field images were obtained every 2 s with acquisition time 300 ms.

Image analysis. Spreading depression was produced by pinprick using a 30-gauge needle. A series of up to 360 images was stacked to create videos from which the direction of $K^+$ wave propagation could be visualized. For analysis of the kinetics of $[K^+]_o$ rise/fall during spreading depression, time courses of pixel intensities were obtained from at least 12 randomly chosen locations from each video. Half-times ($t_{1/2}$) for the increasing and decreasing phases of TAC-Red fluorescence were determined by exponential regression analysis. For analysis of $K^+$ wave velocity, temporal profiles were obtained from 3 or more locations along the direction of wave propagation. Velocity was computed from linear regression of spatial vs. temporal displacement.

$K^+$ measurements using double-barreled microelectrodes. Recordings of extracellular potential and $[K^+]_o$ were carried out using double-barreled $K^+$-selective microelectrodes (tip diameter 5 μm) as described (Milito et al. *J. Cereb. Blood Flow Metab.* 8, 155-162 (1988); Stringer et al. *Epilepsy Res.* 4, 177-186 (1989)). One barrel of the microelectrodes contained a $K^+$ ion exchanger (IE190, WPI, FL) and the reference barrel was filled with 150 mM NaCl. Cortical field potentials and $[K^+]_o$-dependent signals were recorded using a high input impedance dual electrometer (FD230, electrometer, WPI, FL) and MP150 amplifier (Biopac system, CA). Electrodes were calibrated in each experiment. Mice were anesthesized and prepared as described above, with a ground Ag/AgCl electrode inserted subcutaneously and the $K^+$ microelectrode inserted about 400 μm deep.

TAC-Red as an indicator for measurement of $K^+$ channel function for high-throughput screening applications. CHO-K1 cells (ATCC CCL-61) were cultured in Ham's F12 media supplemented with 10% fetal bovine serum, 100 U/ml penicillin and 100 μg/ml streptomycin at 37° C. in a 5% $CO_2$/95% air atmosphere and used at ~90% confluence. For measurements using epifluorescence microscopy cells were grown until reaching confluency on 18-mm diameter round glass coverslips. For fluorescence plate reader assays cells were cultured on Costar 96-well black plates with a clear flat bottom and used when just confluent.

The following buffers were used for $K^+$ transport measurements:

0 $K^+$ buffer: glucose 6 mM, $CaCl_2$ 2 mM, $MgCl_2$ 1 mM, choline chloride 5 mM, NaCl 137.6 mM, HEPES 10 mM pH 7.4;

0 $Na^+$ 0 $K^+$ buffer: glucose 6 mM, $CaCl_2$ 2 mM, $MgCl_2$ 1 mM, choline chloride 142.6 mM, HEPES 10 mM, pH 7.4;

High $K^+$ buffer: glucose 6 mM, $CaCl_2$ 2 mM, $MgCl_2$ 1 mM, KCl 100 mM, NaCl 42.6 mM, HEPES 10 mM pH 7.4;

$Na^+K^+$ buffer: glucose 6 mM, $CaCl_2$ 2 mM, $MgCl_2$ 1 mM, KCl 5 mM, NaCl 137.6 mM, HEPES 10 mM pH 7.4.

Example 1

TAC Red Conjugate and Spectroscopic Analysis

FIG. 1, Panel a provides a schematic of the synthesis of the TAC-Red chromoionophore of the invention. Aldehyde ionophore 1 was synthesized as described in He et al. *J. Am. Chem. Soc.* 125, 1468-1469 (2003). TAC-Red was synthesised by condensation of 3-dimethylaminophenol with ionophore 1 to give compound 2, which on oxidation with tetrachloro-1,4-benzoquinone gave TAC-Red 3.

Compound 2, 9-[4-(6,7,9,10,12,13,20,21,23,24-decahydro-2,17-dimethyl-5,14-(ethanoxyethanoxyethano)-5H, 14H,22H-dibenzo[h,q][1,4,10,16,7,13,19]tetraoxatriazacyclo-heneicosin-22-yl)-3-(2-methoxyethoxy)phenyl]-N,N,N', N'-tetramethyl-9H-xanthene-3,6-diamine, was synthesized by stirring aldehyde 1 (100 mg, 0.138 mmol) and 3-dimethylaminophenol (41 mg, 0.303 mmol) in 5 ml propionic acid with catalytic amount p-toluene sulfonic acid (PTSA) for 20 h at 60° C. After cooling, compound 2 was precipitated with 3M sodium acetate and the precipitated solid was collected by centrifugation, washed with water and dried, giving approximately 0.130 gm of a brownish-rose coloured solid, which was used immediately for subsequent reaction.

TAC-Red, {6-Dimethylamino-9-[4-(6,7,9,10,12,13,20,21, 23,24-decahydro-2,17-dimethyl-5,14-(ethanoxyethanoxyethano)-5H,14H,22H-dibenzo[h,q][1,4,10,16,7,13,19]tetraoxatriazacyclo-heneicosin-22-yl)-3-(2-methoxyethoxy) phenyl]xanthen-3-ylidene}dimethylammonium chloride, was synthesized by stirring compound 2 (130 mg, 0.135 mmol) and tetrachloro-1,4-benzoquinone (66 mg, 0.271 mmol) in methanol:chloroform (1:1) at ambient temperature for 15 h. Excess tetrachloro-1,4-benzoquinone was removed by filtration and reaction mixture was concentrated under reduced pressure. The residue was purified twice by chromatography on silica gel using $CHCl_3$:MeOH:AcOH (9:1:0.1) as eluent to get 7 mg of TAC-Red as a crimson to dark violet semisolid (overall yield about 5%). 1H NMR (400 MHz, $CD_3OD$, ppm) δ 7.8-6.7 (m, 15H), 4.2-2.8 (m, 51H), 2.28 (s, 6H); ESMS calculated for $^{12}C_{56}^{1}H_{72}^{14}N_5^{16}O_9$.Cl m/z 994.5; found, m/z 959 ($M^+$-Cl).

The TAC-Red compound was subjected to spectroscopic analysis. Fluorescence measurements were carried out by standard procedures using a FluoroMax-3 fluorimeter. Fluorescence titrations were carried out at 540 nm excitation and 574 nm emission wavelengths using aqueous solution containing about 7 μM at pH 7.0 (buffered with 5 mM HEPES) unless titrated with NaOH/HCl to other pH.

Spectra in FIG. 1, Panel b were obtained using balanced KCl/choline Cl to keep ionic strength constant at 300 mM. The titration in FIG. 1, panel c was done by adding indicated NaCl/KCl from concentrated stock solutions. The data in FIG. 1, panel d were obtained at constant ionic strength (300 mM) using NaCl or choline Cl to balance the KCl.

TAC-Red fluorescence increased by more than 23-fold with $K^+$ concentration increasing from 0-200 mM (FIG. 1, panel b), with excellent $K^+$ sensitivity in the range of $K^+$ (0-40 mM) expected in the brain ECS. FIG. 1, panel c shows that TAC-Red fluorescence was increased slightly by 50 and 150 mM Na$^+$, having a K$^+$-to-Na$^+$ selectivity ratio of about 37 at 50 mM. The TAC-Red fluorescence response was rapid when K$^+$ was increased from 0 to 5 mM in a stop-flow measurement (FIG. 1, panel c, inset), with greater than 90% of the fluorescence increase occurring in under 1 ms. Thus, the chromoionophore provided a soluble indicator which exhibits both very rapid changes in detectable signal intensity in response to changes in potassium concentrations, and also exhibited very good selectivity for potassium over sodium.

FIG. 1, panel d shows a titration of TAC-Red fluorescence vs. K$^+$ concentration. The presence of 150 mM Na$^+$ (in place of 150 mM choline$^+$) did not affect TAC-Red fluorescence vs. K$^+$. Titrations with monovalent cations showed specificity for K$^+$, Rb$^+$ and Cs$^+$ over Na$^+$ and Li$^+$ (FIG. 1, panel d). TAC-Red fluorescence was not sensitive to divalent cations (Ca$^{++}$ or Mg$^{++}$) or various anions, or to pH in the range 6-8 (FIG. 1, panel e). TAC-Red was membrane impermeant, as expected for the bulky triazacryptand-rosamine conjugate, as demonstrated by <1% transport across Fisher rat thyroid epithelial cell monolayers in 6 hours. TAC-Red did not affect cell viability or growth, indicating low cellular toxicity.

An alternate synthesis of the TAC-Red chromoionophore of the invention is shown in FIG. 1, Panel f.

4-methyl-2-halophenol 1 can be alkylated with excess 1,2-dibromoethane to give bromoethoxyhalophenylether 2 and used for dialkylation with aniline 5 to give dihalophenoxyalkyl aniline 6. Compound 6 can be treated with commercially available 1,4,10,13-tetraoxa-7,16-diazacyclooctadecane in the presence of palladium catalyst and biphenyl monophosphine ligand to give potassium ionophore 7. Compound 7 can be formylated with DMF/POCl$_3$ to give ionophore aldehyde 8, which can be conveniently used for synthesis of TAC-Red using 3-dimethylaminophenol, catalytic PTSA, and subsequent treatment with chloranil.

Example 2

TAC-Julolidine Red or TAC-Crimson Conjugate

Figure 9:
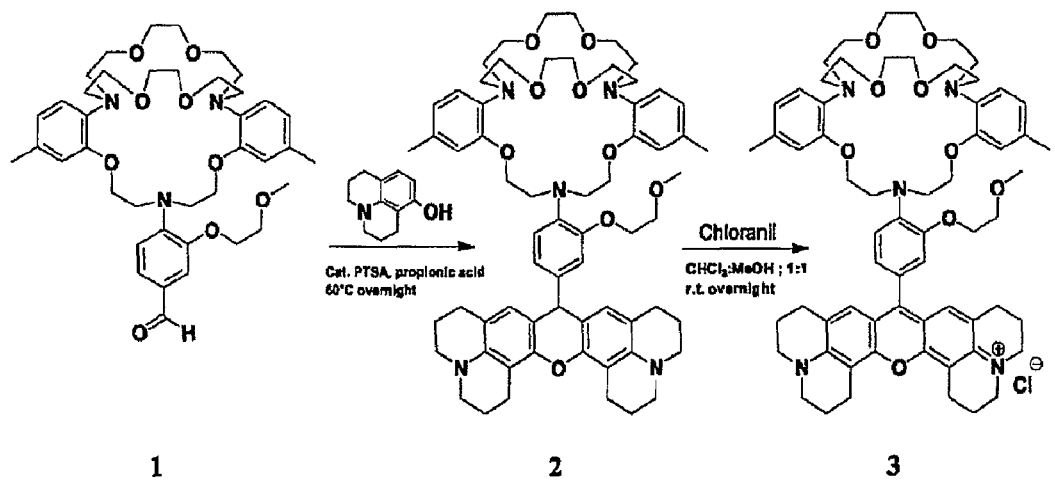
FIG. 9 illustrates a synthetic scheme for TAC-Julolidine Red or TAC-Crimson.

FIG. 9 provides a schematic for synthesis of TAC-Julolidine Red (TAC-Jr or TAC-Crimson) (1H,5H,11H,15H-Xantheno[2,3,4-ij:5,6,7-i'j']diquinolizin-18-ium, 9-[4-(6,7,9,10,12,13,20,21,23,24-decahydro-2,17-dimethyl-5,14-(ethanoxyethanoxyethano)-5H,14H,22H-dibenzo[h,q][1,4,10,16,7,13,19]tetraoxatriazacycloheneicosin-22-yl)-3-(2-methoxyethoxy)phenyl]-2,3,6,7,12,13,16,17-octahydro-, chloride).

Compound 2 of FIG. 9 was synthesized by stirring aldehyde 1 (72 mg, 0.10 mmol) and 8-hydroxyjulolidine (41 mg, 0.22 mmol) in 1 ml propionic acid with catalytic amount p-toluene sulfonic acid (PTSA) for 20 h at 60 to 70° C. After cooling, compound 2 was precipitated with 3M sodium acetate and the precipitated solid was collected by centrifugation, washed with water and dried, giving approximately 0.106 gm of a brownish-rose coloured solid, which was used immediately for subsequent reaction.

TAC-Julolidine Red or TAC-Crimson (TAC-Jr) 3, was synthesized by stirring compound 2 (106 mg, 0.1 mmol) and tetrachloro-1,4-benzoquinone (49 mg, 0.2 mmol) in methanol:chloroform (1:1) at ambient temperature for 16 to 20 hrs. Excess tetrachloro-1,4-benzoquinone was removed by filtration and reaction mixture was concentrated under reduced pressure. The residue was purified twice by chromatography on silica gel using CHCl$_3$:MeOH:AcOH (9:1:0.1) as eluent to get 7 mg of TAC-Red as a crimson to dark violet semisolid (overall yield about 5%). $^1$H NMR (400 MHz, CDCl$_3$, ppm) δ 7.9-6.4 (m, 11H), 4.8-2.5 (m, 55H), 2.25 (bs, 6H), 1.96 (bs, 8H); ESMS calculated for $^{12}$C$_{64}$$^1$H$_{80}$$^{14}$N$_5$$^{16}$O$_9$.Cl m/z 1097.5; found, m/z 1062.6 (M$^+$-Cl).

Figure 10:
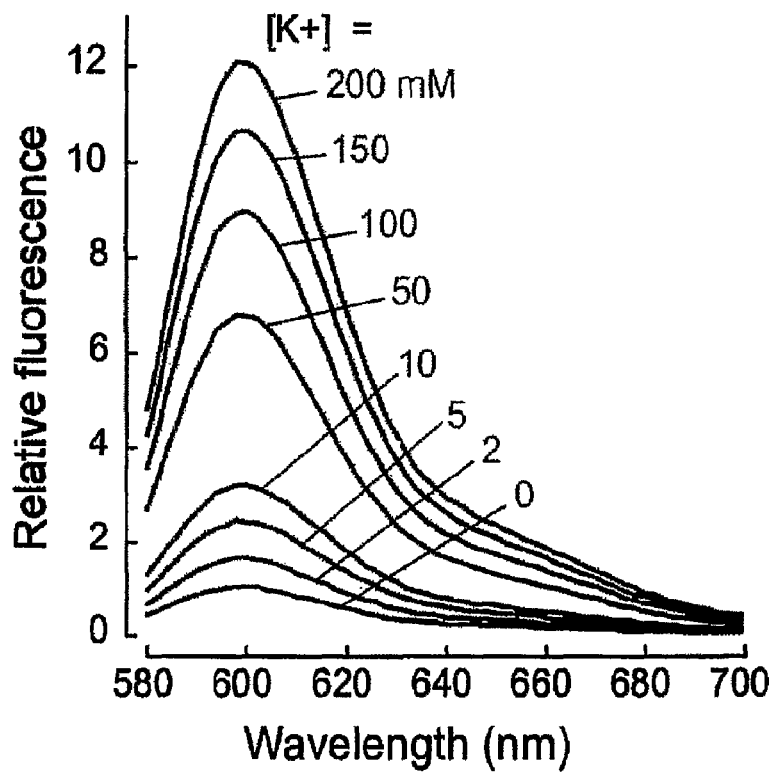
FIG. 10 is a graph showing the emission spectra of TAC-Julolidine Red or TAC-Crimson at various potassium concentrations.

The fluorescent properties of the TAC-Julolidine Red compound were assessed. Fluorescence measurements were carried out by standard procedures using a FluoroMax-3 fluorimeter. Fluorescence titrations were carried out at 570 nm excitation and 599 mm emission wavelengths using aqueous solution containing about 7 μM at pH 7.0 (buffered with 5 mM HEPES). The resulting emission spectra are shown in FIG. 10.

Example 3

TAC-Rhodamine Conjugate

A TAC-Rhodamine conjugate can be synthesized to provide a conjugate having desired characteristics of potassium sensitivity and long wavelength (e.g., excitation above about 500 nm).

Figure 11:
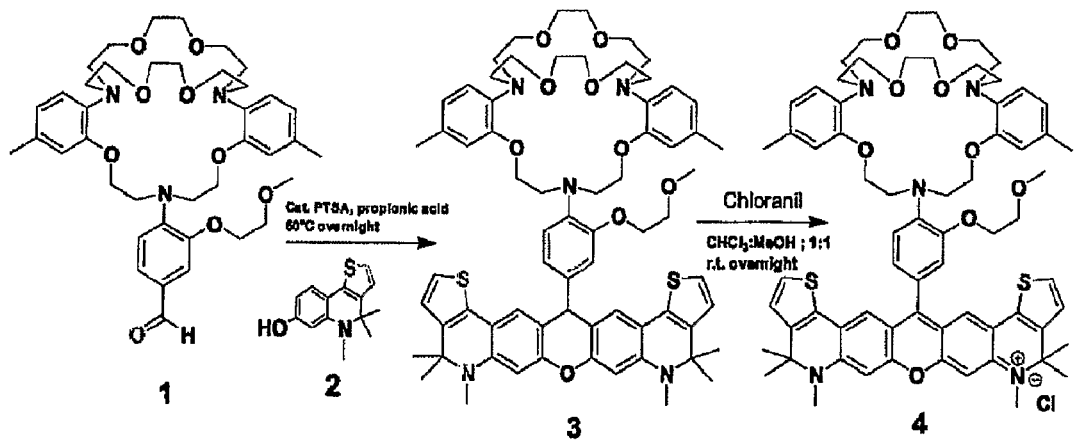
FIG. 11 illustrates a synthetic scheme for a TAC-Rhodamine conjugated sensor.
Figure 12:
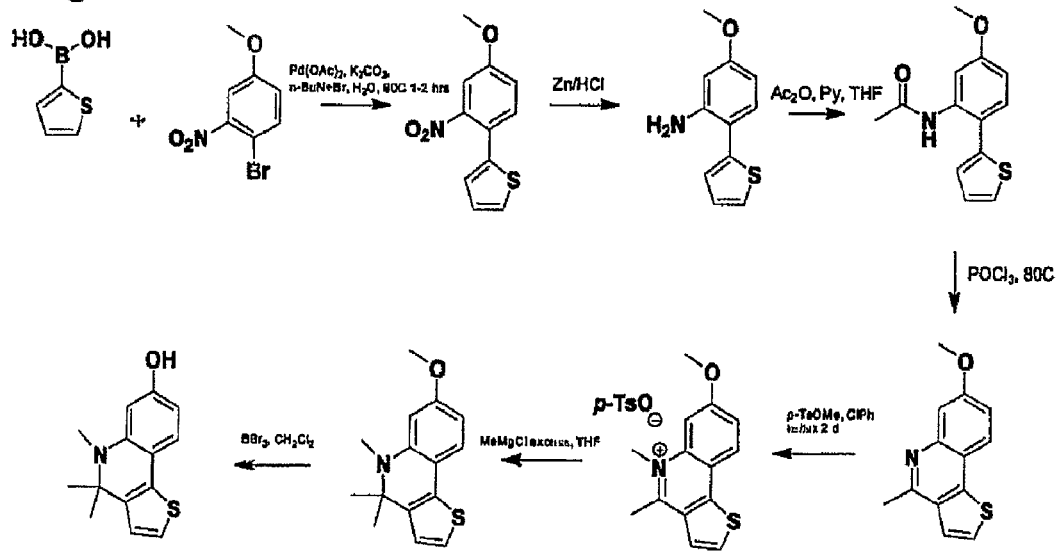
FIG. 12 illustrates a synthetic scheme for synthon 2 described in the schematic of FIG. 11.

FIG. 11 provides a schematic of an exemplary synthetic scheme which can be used to synthesize a TAC-Rhodamine conjugate of the invention. In general, the synthetic scheme for TAC-Rhodamine will be similar to that for TAC-Red and TAC-Julolidine Red or TAC-Crimson, except the starting aminophenol derivative 2 (FIG. 11) which can be synthesized according to the procedure described by Liu et. al. in *Tetrahedron Lett.* 44:4355-4359 (2003). A schematic for an exemplary synthetic scheme for the aminophenol derivative is set out in FIG. 12.

Example 4

TAC-Alexa Fluor Conjugate

Figure 13:
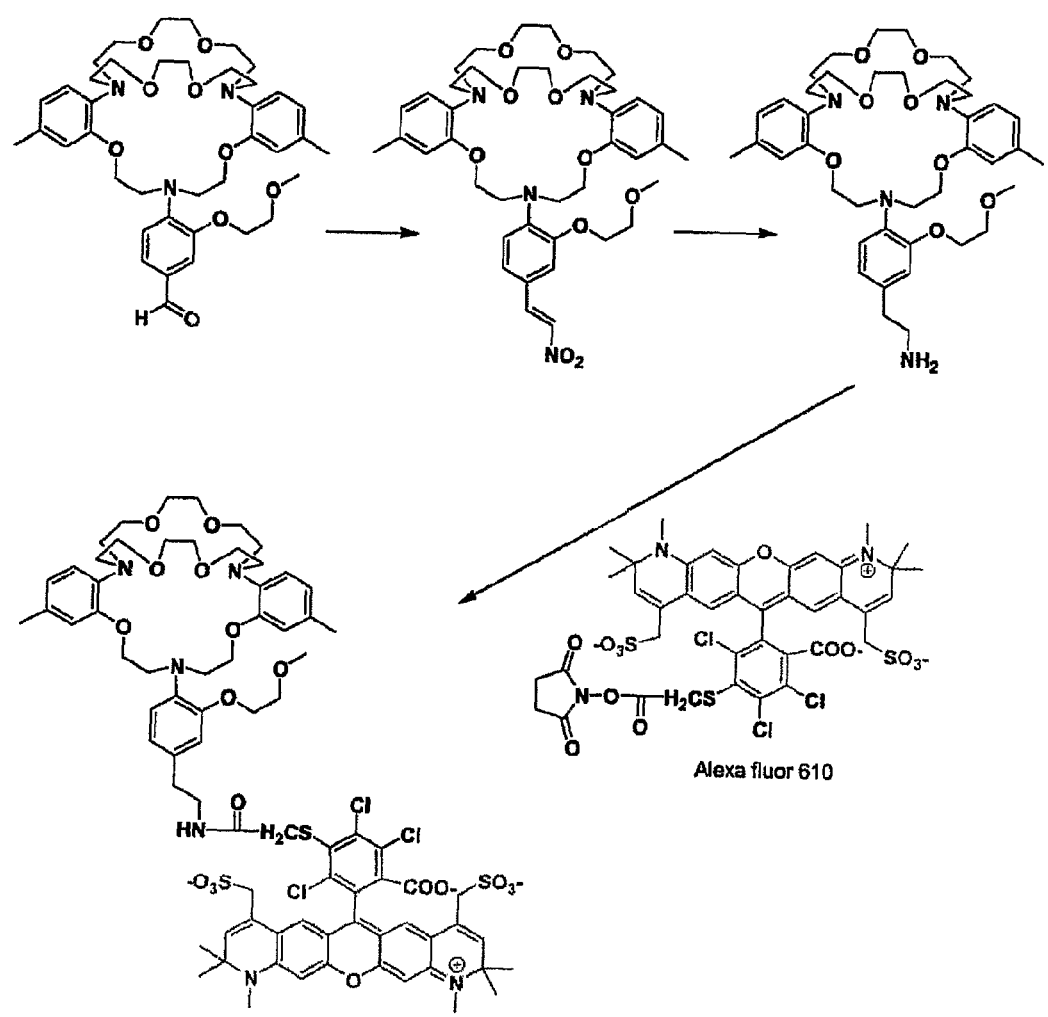
FIG. 13 illustrates a synthetic strategy for a TAC-Alexa Fluor chromoionophore of the invention.

A TAC-Alexa Fluor conjugate can be synthesized to provide a conjugate having desired characteristics of potassium sensitivity and long wavelength (e.g., excitation above about 500 nm). FIG. 13 provides a schematic of an exemplary strategy for synthesis of TAC-Alexa Fluor. Such TAC-Alex Fluor conjugates can also be generated using a succinimidyl ester derivative of alexa fluor dyes, which can be coupled with the starting TAC-aldehyde to provide a amide conjugate.

Example 5

A Near-Infrared (NIR) Potassium Indicator

Figure 16:
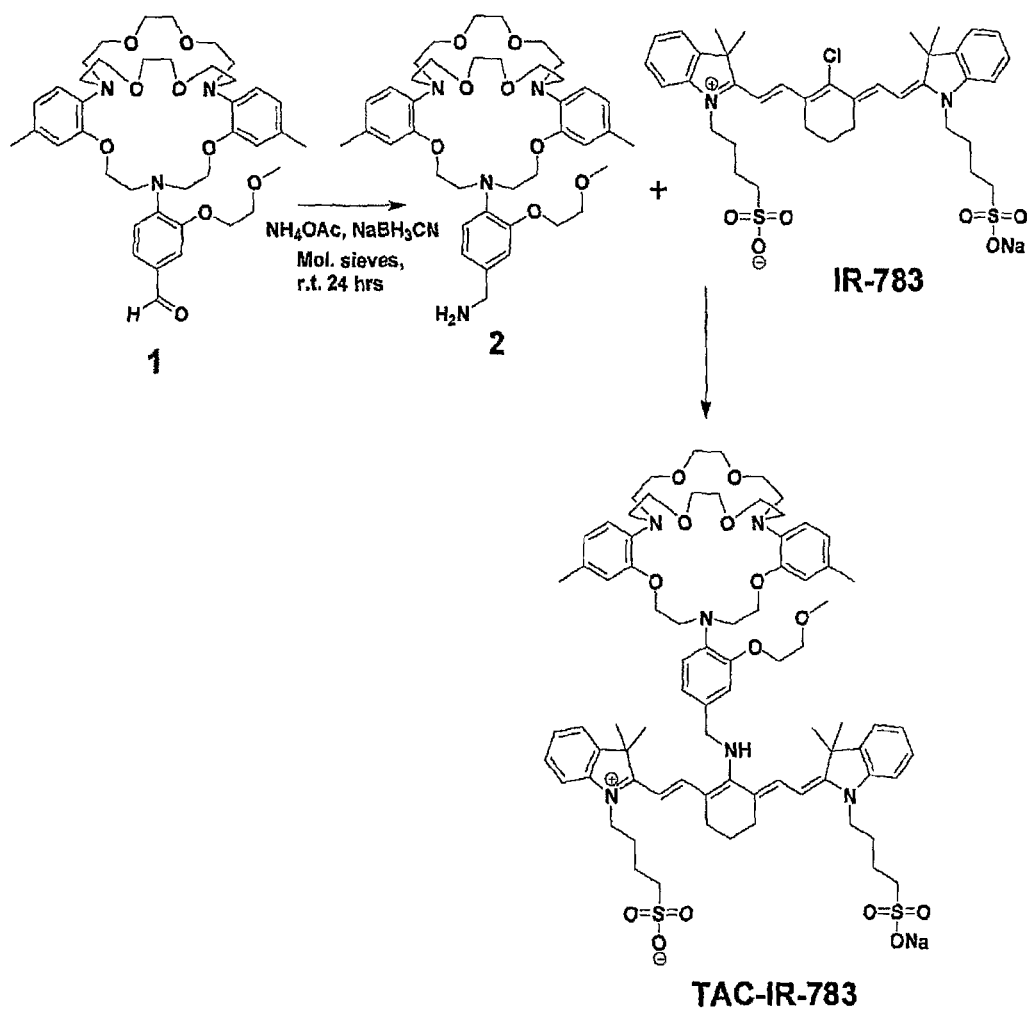
FIG. 16 illustrates a synthetic scheme for TAC-IR-783.

A NIR potassium indicator was synthesized by the reaction scheme shown in FIG. 16. TAC-aldehyde 1 was converted to primary amine 2 by treatment with ammonium acetate and sodium cyanoborohydride in the presence of molecular sieves. Amine 2 was then reacted with cyanine dye IR-783 in anhydrous DMF at 80-90° C., giving TAC-IR-783.

Other cyanine near infra-red dyes (such as IR-806, IR-1061) can be covalently conjugated to the reactive TAC moiety using a similar strategy.

Synthesis of Amine 2: TAC aldehyde 1 (60 mg, 0.08 mmol) was dissolved in 10 ml of dry methanol, and ammonium acetate (6 mg, 0.8 mmol) and sodium cynoborohydride (5 mg, 0.08 mmol) were the added and stirred at room temperature over molecular sieves for 24 hr. The molecular sieves were filtered and the methanolic reaction mixture was concentrated under reduced pressure. The residue was acidified with dilute HCl, and extracted with dichloromethane to remove any unreacted TAC-aldehyde. The aqueous layer was alkalinized with lithium hydroxide, giving a sticky mass. The mass was extracted with dichloromethane, giving purified amine 2 (15 mg). $^1$H NMR (CDCl$_3$): δ 1.80-2.00 (bs, 2H), 2.19 (s, 6H), 3.0-4.6 (m, 41H), 6.4-7.4 (m, 9H); ES-MS calculated for $^{12}C_{40}{}^1H_{58}{}^{14}N_4{}^{16}O_8$ m/z 722.91; found, m/z 724.

Synthesis of TAC-IR-783: Synthesized amine 2 (3 mg, 0.005 mmol) was reacted with IR-783 (0.4 mg, 0.0005 mmol) in 0.3 ml dry DMF and stirred at 80 to 90° C. for 4 hr. The reaction mixture cooled and precipitated by addition of ethylacetate-hexane (3:2) with vigorous stirring. A yellowish green solid (TAC-IR-783) was obtained by centrifugation.

Example 6

TAC-BODIPY Dual Wavelength Conjugate

A TAC-BODIPY conjugate can be synthesized to provide a conjugate having desired characteristics of potassium sensitivity and long wavelength (e.g., excitation above about 500 nm).

Figure 14:
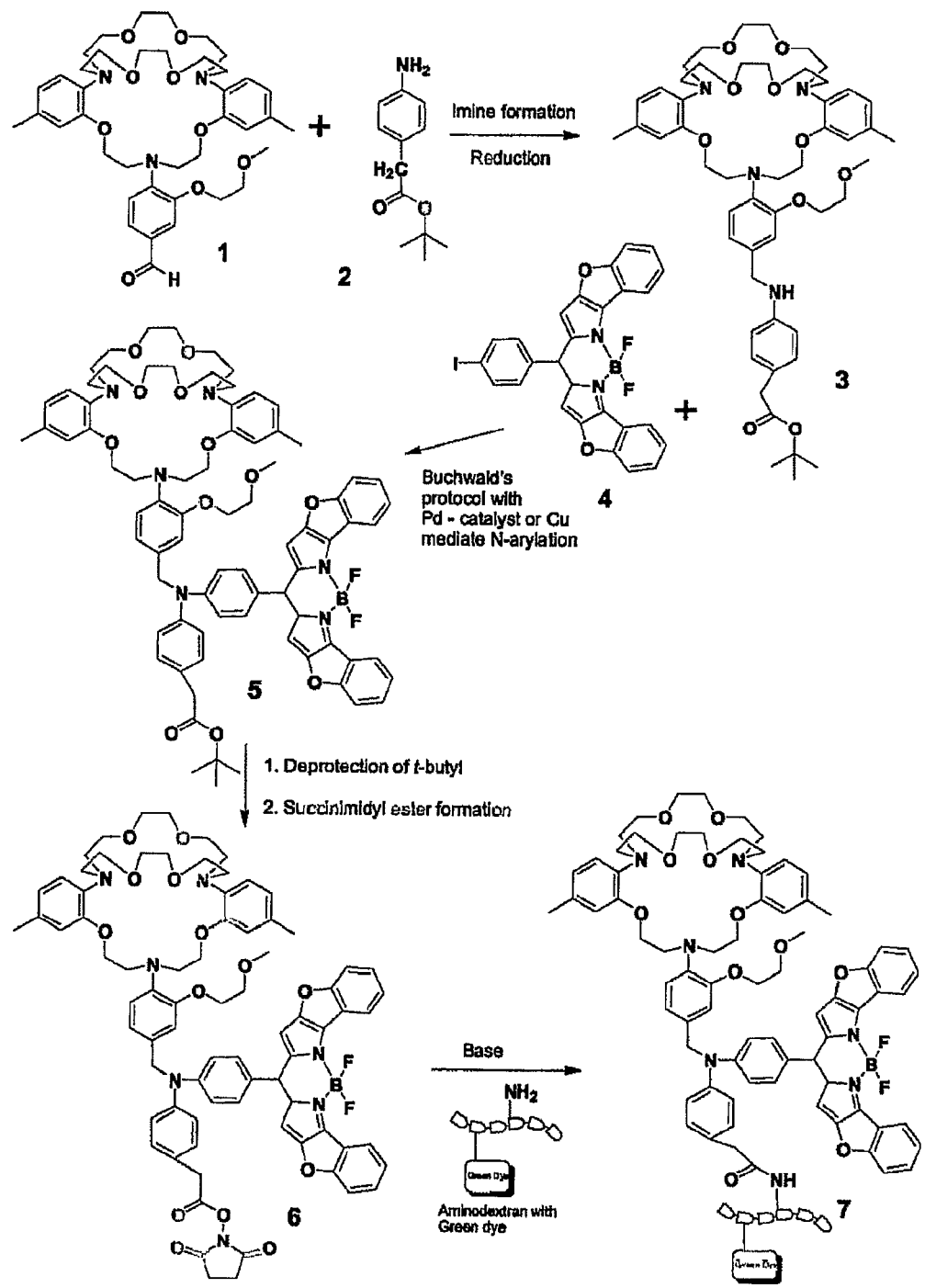
FIG. 14 illustrates a synthetic strategy for a TAC-BODIPY potassium sensor.
Figure 15:
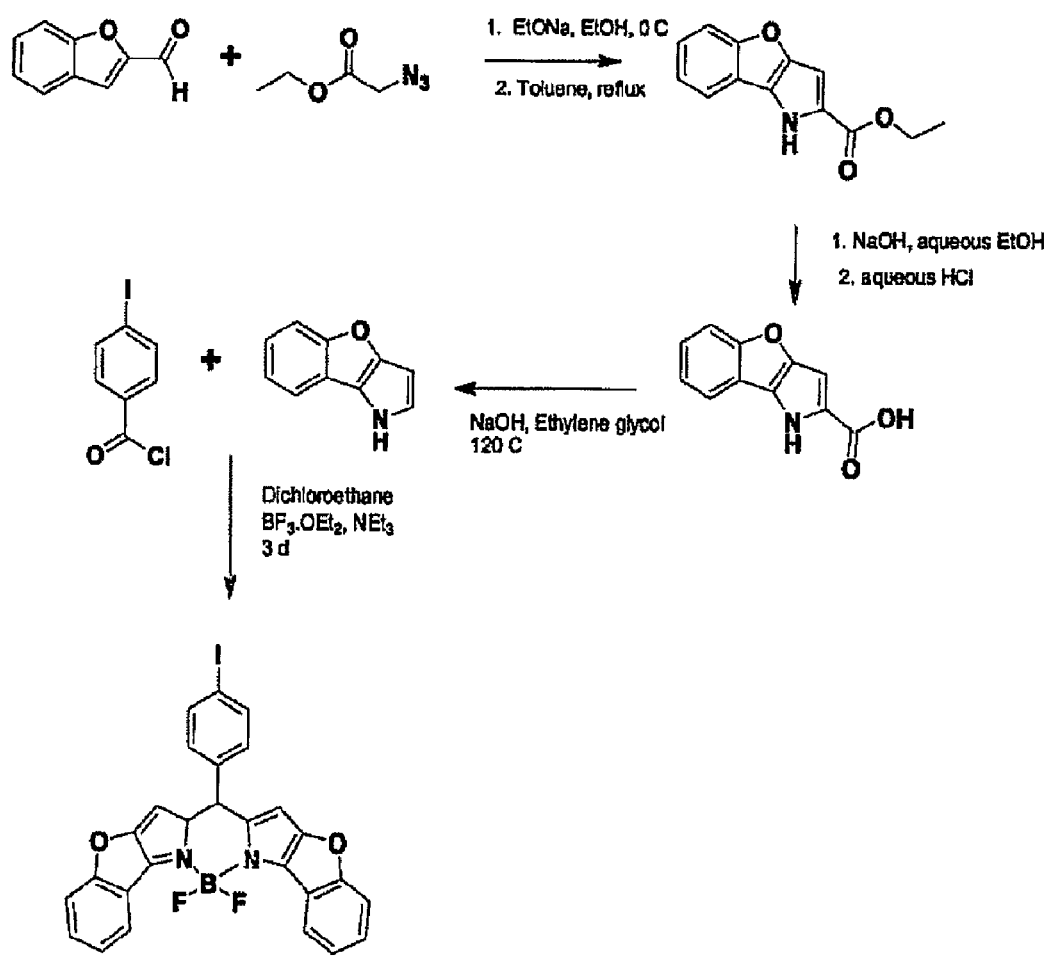
FIG. 15 illustrates a synthetic scheme for synthon 4 in FIG. 14.

FIG. 14 provides a schematic of an exemplary strategy for synthesis of TAC-BODIPY. In general, synthesis of a long wavelength BODIPY conjugated potassium sensor involves the formation of a Schiff's base using aldehyde 1 with t-butyl-4-aminophenylacetate 2 and in situ reduction to produce secondary amine 3. FIG. 15 provides a schematic of an exemplary scheme for synthesis of a reactive BODIPY dye 4 of FIG. 14. Synthesis of this compound can be carried out according to the procedure described by Chen et. al. in *J. Org. Chem.* 65:2900-2906 (2000).

As illustrated in FIG. 14, secondary amine 3 is reacted with reactive BODIPY dye 4 with palladium catalyst with ligand and base or copper mediated N-arylation, or in presence of a base, to produce compound 5. Later, deprotection of t-butyl group and formation of succinimidyl ester produced compound 6, which is then treated with an aminodextran (represented by the chain of open, rounded rectangles) conjugated to a green dye in presence of base to produce a long wavelength BODIPY conjugated sensor of compound 7. The green dye can be any suitable green dye that has an emission wavelength that is readily distinguishable from the emission wavelength of BODIPY.

Example 7

Dual Wavelength Analogue of TAC-Red/BODIPY Conjugate

Dual wavelength potassium sensors provide a ratioable sensor that contains, for example, a potassium insensitive green dye (e.g., BODIPY) and potassium sensitive red dye (e.g., an analogue of TAC-Red) covalently linked through dextran. Such dual wavelength conjugates are thus useful for precise measurement of an amount of potassium in different biological applications. The covalent linkage of the conjugate to dextran provides for a highly water soluble, membrane impermeant dye.

Figure 18:
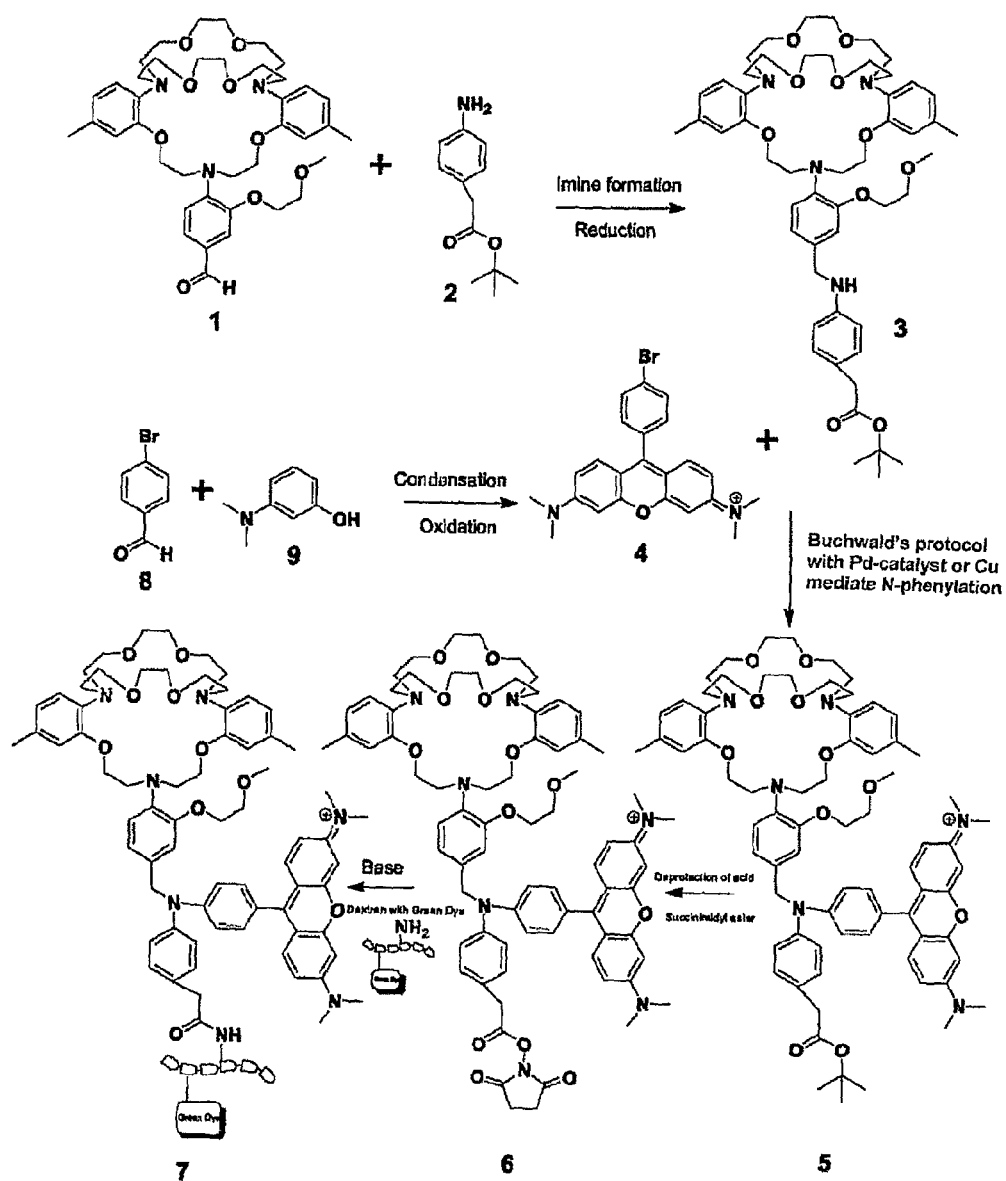
FIG. 18 is an exemplary synthetic scheme for construction of a dual wavelength potassium sensor.

An exemplary schematic for construction of a dual wavelength potassium indicator is depicted in FIG. 18. Synthesis of these conjugates can involve the formation of a Schiff's base using aldehyde 1 with t-butyl-4-aminopehnylacetate 2 and in situ reduction to produce a secondary amine 3. Bromorhodamine is synthesized by condensing 4-bromobenzaldehyde 8 with 3-(dimethylamino)phenol 9 which, on oxidation with chloranil, produces bromorhodamine 4. Secondary amine 3 is then reacted with bromorhodamine 4 with palladium catalyst with ligand in presence of base or a copper catalyst with base, or base without catalyst, to produce compound 5. Deprotection of the t-butyl group and formation of succinimidyl ester will generate compound 6, which is then treated with aminodextraten conjugated with green dye (BODIPY) in presence of base, producing dual wavelength sensor compound 7.

One advantage of dual wavelength conjugates is that the ratio analysis of fluorescence intensity from the two different dyes (e.g., an increase in the red emission spectra due to an increase in potassium concentration versus a baseline intensity of green fluorescence) provides a means for determining the absolute value of potassium concentration in biological systems. For example, dual wavelength chromoionophores of the invention can be used to provide for determination of absolute K$^+$ concentration in brain extracellular space during seizures or spreading depression, rather than just relative changes in K$^+$.

Example 8

Ratioable, Dextran-Conjugated Potassium Indicator

Figure 17:
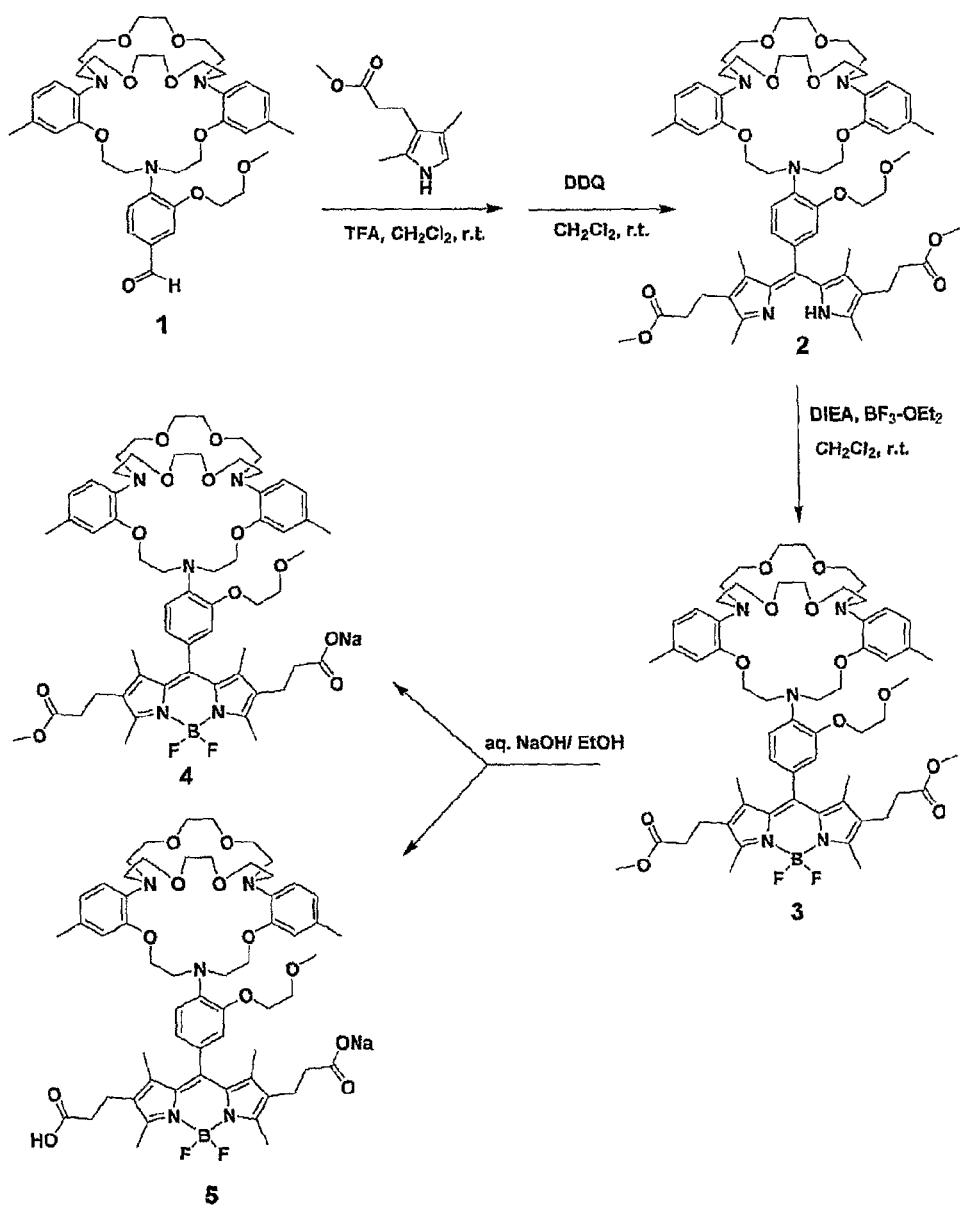
FIG. 17 illustrates a synthetic strategy for a TAC-Lime potassium sensor (compound 3), which may be used to construct a dual wavelength potassium sensor (compound 8).
Figure 17:
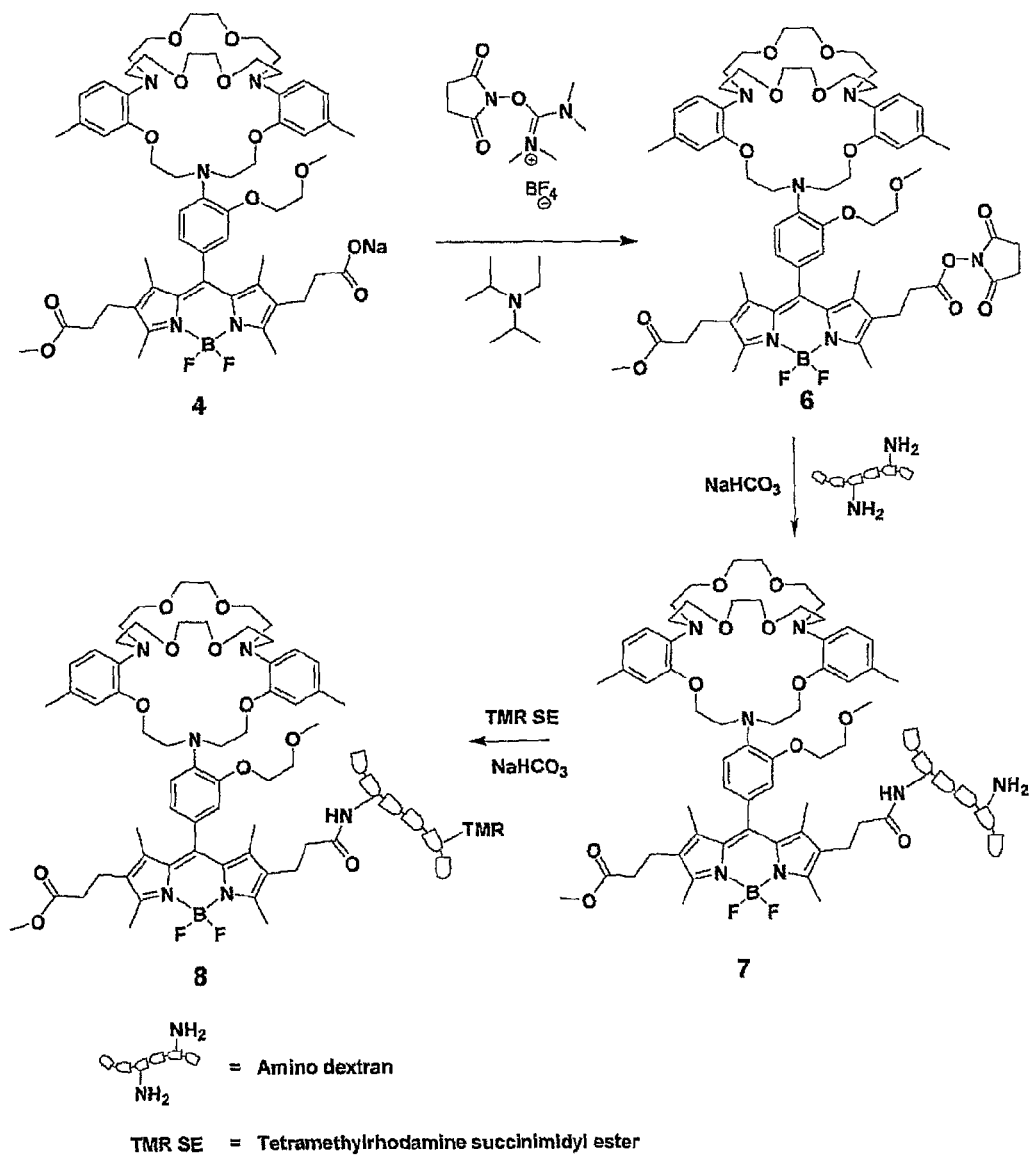

A green-fluorescing K$^+$ sensitive fluorescent indicator, TAC-Lime (compound 3) was synthesized by the scheme shown in FIG. 17. To produce a ratioable, dextran-bound indicator, TAC-Lime was derivatized and conjugated to amino dextran along with the red fluorescing, K$^+$ insensitive chromophore tetramethylrhodamine (TMR).

Synthesis of 3-(2-methoxycarbonylethyl)-2,4-dimethylpyrrole: Methyl 5-(benzyloxycarbonyl)-2,4-dimethyl-3-pyrrolepropionate (1.8 gm, 5.7 mmol) was dissolved in 60 ml of acetone and added to 30 mg of 10% Pd/C. The reaction mixture was vigorously shaken under a hydrogen atmosphere for 20 hrs. The Pd/C was filtered and washed with acetone. After evaporation of the filtrate under reduced pressure the residue was dissolved in 6 ml TFA under argon and stirred for 20 min. The reaction mixture was extracted with chloroform and water. The chloroform extract was washed in sodium carbonate and water, dried over magnesium sulfate, filtered and evaporated. The crude product was purified by column chromatography over silica gel with dichloromethane as eluent to get a yellow oil (yield 56%); $^1$H NMR (CDCl$_3$): δ 2.00 (d, 3H), 2.14 (s, 3H), 2.42 (m, 2H), 2.69 (m, 2H), 6.36 (d, 1H), 7.55 (s, 1H); ES-MS calculated for $^{12}C_{10}{}^1H_{15}{}^{14}N^{16}O_2$ m/z 181; found, m/z 182. (synthesized as per *J. Chem. Soc. Perkin Trans* 1 1987, 265-276).

Synthesis of compound 2: TAC-aldehyde 1 (130 mg, 0.180 mmol) and 3-(2-methoxycarbonylethyl)-2,4-dimethylpyrrole (65 mg, 0.360 mmol) were dissolved in 60 ml of anhydrous dichloromethane in an inert atmosphere. One drop of trifluoroacetic acid was added and the solution was stirred at room temperature for 18 hr. A solution of 2,3-dichloro-5,6-dicyano-1,4-benzoquinone (40 mg, 0.180 mmol) in dichloromethane was then added and stirred for 4 hr. The reaction mixture was washed with water, dried over magnesium sulfate, and concentrated under reduced pressure to obtain a crude residue, which was purified by column chromatography over neutral aluminum oxide using dichloromethane, giving ~200 mg of a brown semisolid. $^1$H NMR (CDCl$_3$): δ 1.22 (s, 6H), 2.1-2.8 (m, 20H), 3.2-4.4 (m, 45H), 6.4-7.4 (m, 9H, arm).

Synthesis of TAC-Lime 3: Compound 2 (160 mg, 0.150 mmol) was dissolved in 30 ml of anhydrous dichloromethane in an inert atmosphere. N,N-diisopropylethylamine (0.35 ml, 2.03 mmol) was added and the reaction mixture was stirred for 20 min. BF3-etherate (0.35 ml, 2.82 mmol) was the added and stirring continued for 2 hr. The reaction mixture was washed with water and LiOH (2N). A dichloromethane extract was dried over magnesium sulfate and concentrated on a rotary evaporator. The crude product was purified by column chromatography over neutral aluminum oxide using DCM:MeOH (9.5:0.5), giving an orange gum (~5 mg). $^1$H NMR (CDCl$_3$): δ 1.3 (s, 6H), 2.1-2.6 (m, 20H), 3.2-4.6 (m, 45H), 6.5-8.0 (m, 9H); ES-MS calculated for $^{12}C_{60}{}^{1}H_{80}{}^{10.8}B^{19}F_2{}^{14}N_5{}^{16}O_{12}$ m/z 1112.11; found m/z 1112.47.

Hydrolysis of TAC-Lime—synthesis of compounds 4 & 5: TAC-Lime 3 (5 mg, 0.004 mmol) was dissolved in ethanol and 0.2 ml of 0.2 N sodium hydroxide was added. The mixture was refluxed for 2 hr. The residue after evaporation was acidified with dilute hydrochloric acid and extracted twice with dichloromethane. The combined dichloromethane extract was dried over magnesium sulfate and purified by preparative TLC over neutral aluminum oxide using dichloromethane:methanol:acetic acid (4:1:0.1) to get the monoacid sodium salt 4 and the diacid monosodium salt 5. ES-MS of monoacid sodium salt 4 calculated for $^{12}C_{59}{}^{1}H_{77}{}^{10.8}B^{19}F_2{}^{14}N_5{}^{23}Na^{16}O_{12}$ m/z 1120; found m/z 1120.6 & 1098 (M$^+$-Na). ES-MS of diacid monosodium salt 5 calculated for $^{12}C_{58}{}^{1}H_{75}{}^{10.8}B^{19}F_2{}^{14}N_5{}^{23}Na^{16}O_{12}$ m/z 1106; found m/z 1106 & 1084 (M$^+$-Na).

Synthesis of TAC-Lime succinimidyl ester 6: TAC-Lime monoacid sodium salt 4 (1 mg) was dissolved in anhydrous DMF and treated with 1.2 equivalent of O—(N-succinimidyl) N,N,N',N'-tetramethyluronium tetrafluoroborate and catalytic amount of N,N-diisopropylethyl amine for 6 hr with stirring. The reaction mixture was then diluted with excess diethyl ether with vigorous stirring to precipitate small quantity of a sticky mass, which was centrifuged to give an orange brown sticky solid. ES-MS calculated for $^{12}C_{63}{}^{1}H_{81}{}^{10.8}B^{19}F_2{}^{14}N_6{}^{16}O_{14}$ m/z 1194.5; found m/z 1195.

Synthesis of TAC-Lime-dextran conjugate of 7: Compound 6 (0.5 mg) was dissolved in 0.2 ml of a mixture of water-DMSO (DMSO used as a co-solvent to dissolve) and added to 0.3 ml solution of 1.3 mg (3 eq) of amino dextran (avg. MW 10000, 3 mole of amine) in 0.4 M sodium bicarbonate. The reaction mixture was stirred at room temperature for 6 hr, purified by dialysis, and then lyophilized to give the dextran-TAC-Lime conjugate. The labeling ratio for 10000 dalton dextan—TAC-Lime:dextran was 2:1. A similar procedure for synthesis of a 40000 dalton dextran was done using 1 eq amino dextran (avg. MW 40000, 8 moles of amine) and 8 eq of TAC-Lime succinimidyl ester 6 to get the TAC-Lime-dextran conjugate with TAC-Lime:dextran labeling ratio of 6.4:1.

Synthesis of dual wavelength TAC-Lime-dextran-TMR conjugate 8: Compound 7 was treated with 1 eq of tetramethylrhodamine succinimidyl ester (TMR-SE) in 0.3 M aqueous sodium bicarbonate for 2 hr with stirring. The dual-labeled TAC-Lime-dextran-TMR conjugate were purified by dialysis and lyophilized.

Figure 8:
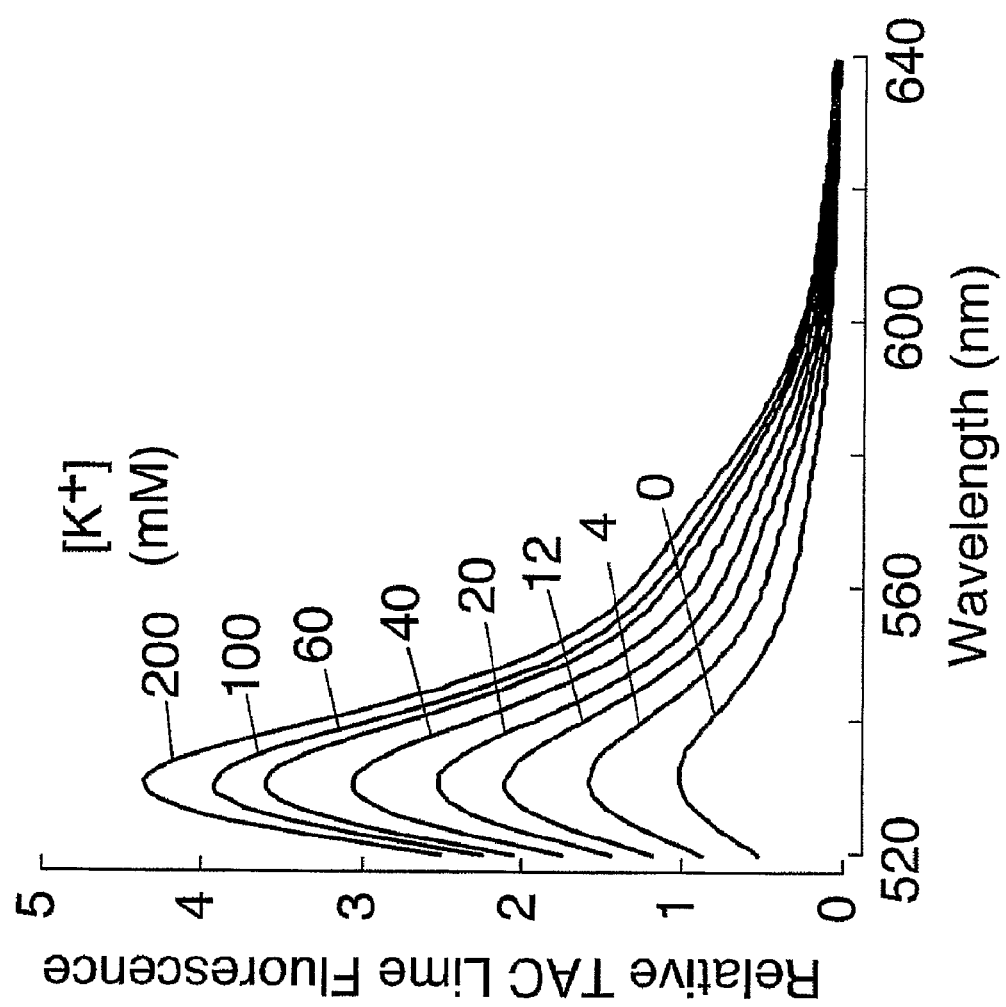
FIG. 8 illustrates fluorescence spectra of 7 µM TAC-Lime monoacid conjugate in 5 mM HEPES (pH 7.04) containing indicated [$K^+$]. Excitation wavelength 500 nm; emission wavelength, 530 nm). Relative fluorescence shown, with fluorescence in the absence of $K^+$ set to unity.

FIG. 8 shows increase in TAC-Lime fluorescence with indicated amount of potassium from the TAC-Lime monoacid conjugate (7 μM) in HEPES pH=7.04.

Example 9

Dual Wavelength TAC-Red Conjugate

Figure 19:
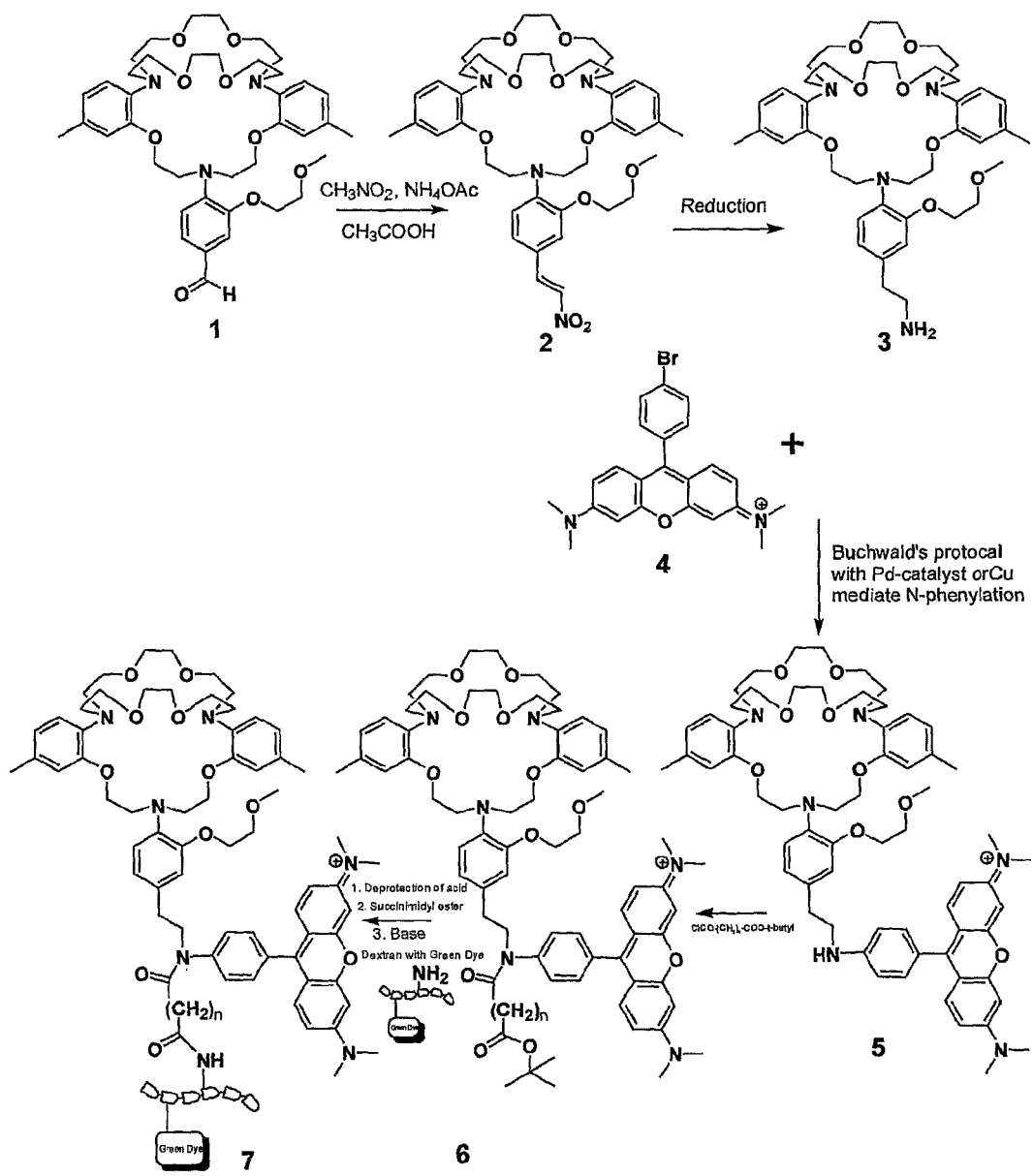
FIG. 19 illustrates a synthetic scheme for a dual wavelength potassium sensor.

An exemplary schematic for construction of a dual wavelength potassium indicator is depicted in FIG. 19. In this synthetic scheme, compound 3 is reacted with compound 4 to generate a single wavelength chromoionophore 5, which is then further modified to provide compound 7 containing two chromophores linked to dextran by an amide linkage. Compound 3 may be prepared by methods known in the art. See, e.g., He et al. *J. Am. Chem. Soc.* 125:1468-1469 (2003). This synthetic strategy then allows production of a chromoionophore having a chromophore of a desired excitation and emission wavelength. The green dye provides a potassium-insensitive detectable signal that is distinguishable from that of the potassium-sensitive.

Example 10

Dual Wavelength TAC-Red Conjugate Having Potassium-Insensitive Dyes

Figure 20:
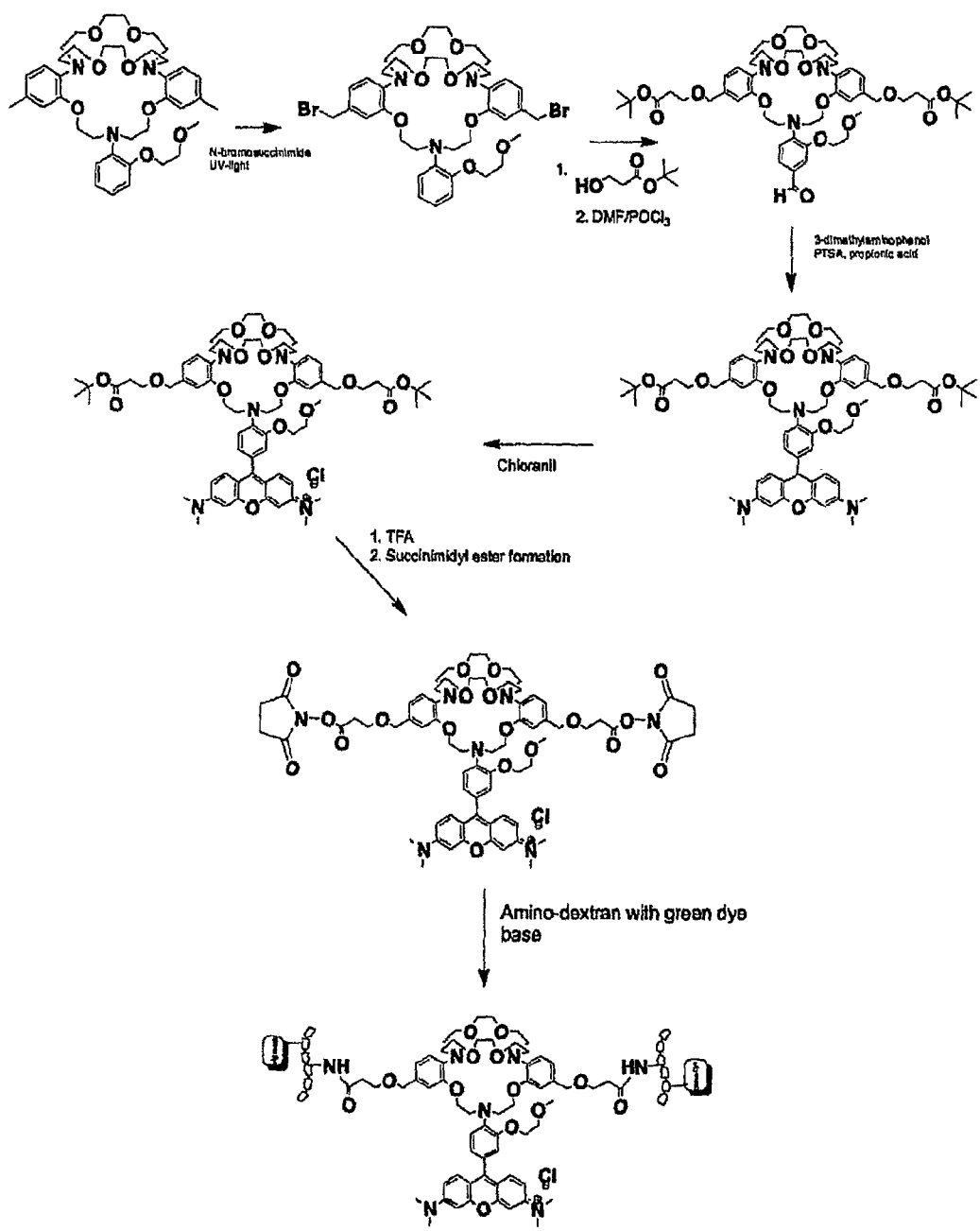
FIG. 20 illustrates a synthetic scheme for a dual wavelength potassium sensor having potassium-insensitive chromophore attached to the ionophoric moiety.

An exemplary schematic for construction of a dual wavelength potassium indicator is depicted in FIG. 20. In this example, the ionophoric moiety can be modified to have potassium binding-insensitive green dyes, which are linked to the ionophoric moiety through a water soluble polymer (represented by the chain of open, rounded rectangles).

Example 11

Dual Wavelength TAC-Red Conjugate Having Potassium-Insensitive Dyes

Figure 21:
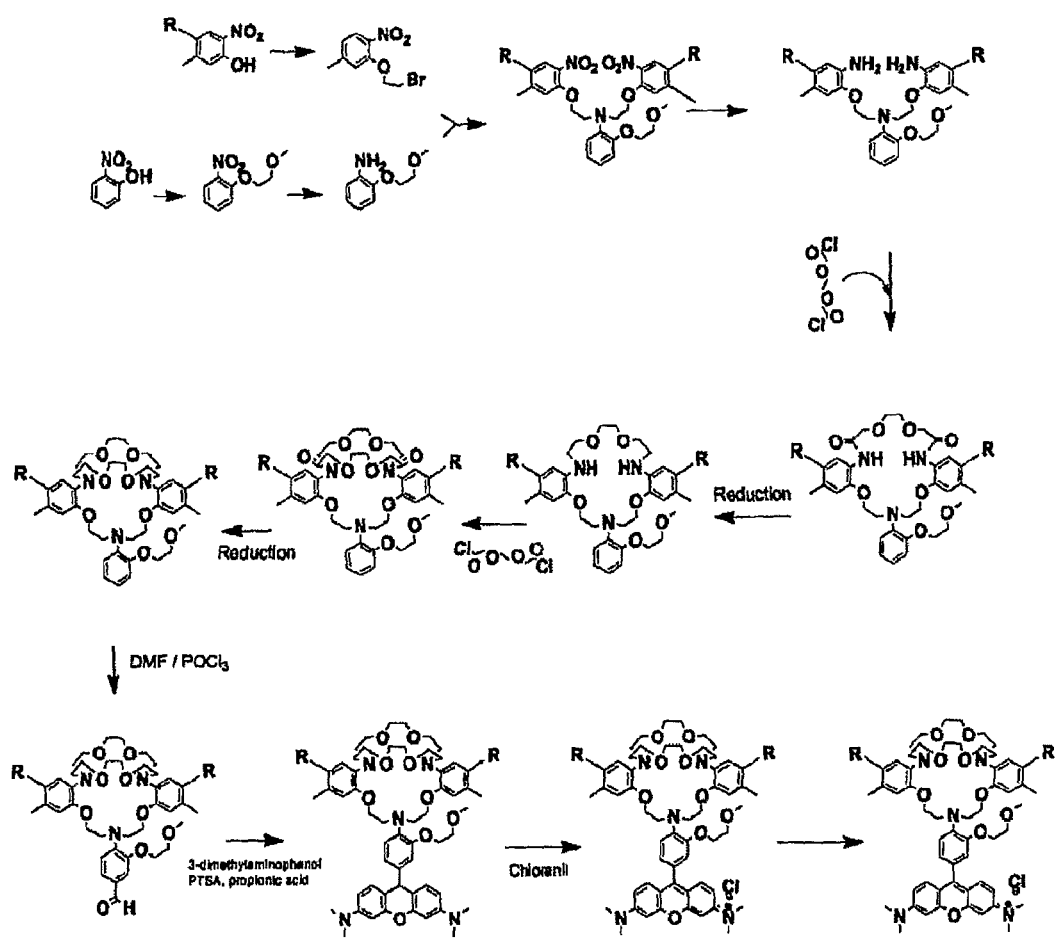
FIG. 21 illustrates a synthetic scheme for a dual wavelength potassium sensor having potassium-insensitive chromophores attached to the ionophoric moiety.

An exemplary schematic for construction of a dual wavelength potassium indicator is depicted in FIG. 21. In this example, the ionophoric moiety can be modified to have potassium binding-insensitive dyes linked to the ionophoric moiety (e.g., through a water soluble polymer). The position of the potassium insensitive dyes is shown by "R", which represents a reactive group that can be converted to succinimidyl ester for conjugation with aminodextran having a covalently bound green dye.

Example 12

TAC-Red [K$^+$]$_o$ Measurements in Brain Cortex

The ECS of mouse brain was stained with TAC-Red by exposing the intact dura (after craniectomy) for 5 minutes to an artificial cerebrospinal fluid (aCSF) solution containing 50 μM TAC-Red. Excess TAC-Red was washed. This transdural dye labeling approach was developed previously to stain the ECS with fluorescent dextrans for photobleaching measurements (Binder et al. *J. Neurosci.* 24, 8049-8056 (2004)). The TAC-red-stained brain cortex was brightly red fluorescent, with fairly uniform parenchymal staining but no staining of blood vessels. There was little influence of cerebral blood flow on the signal, with less than 2% change in TAC-Red fluorescence when mice breathed 0 vs. 5% CO$_2$.

Figure 2:
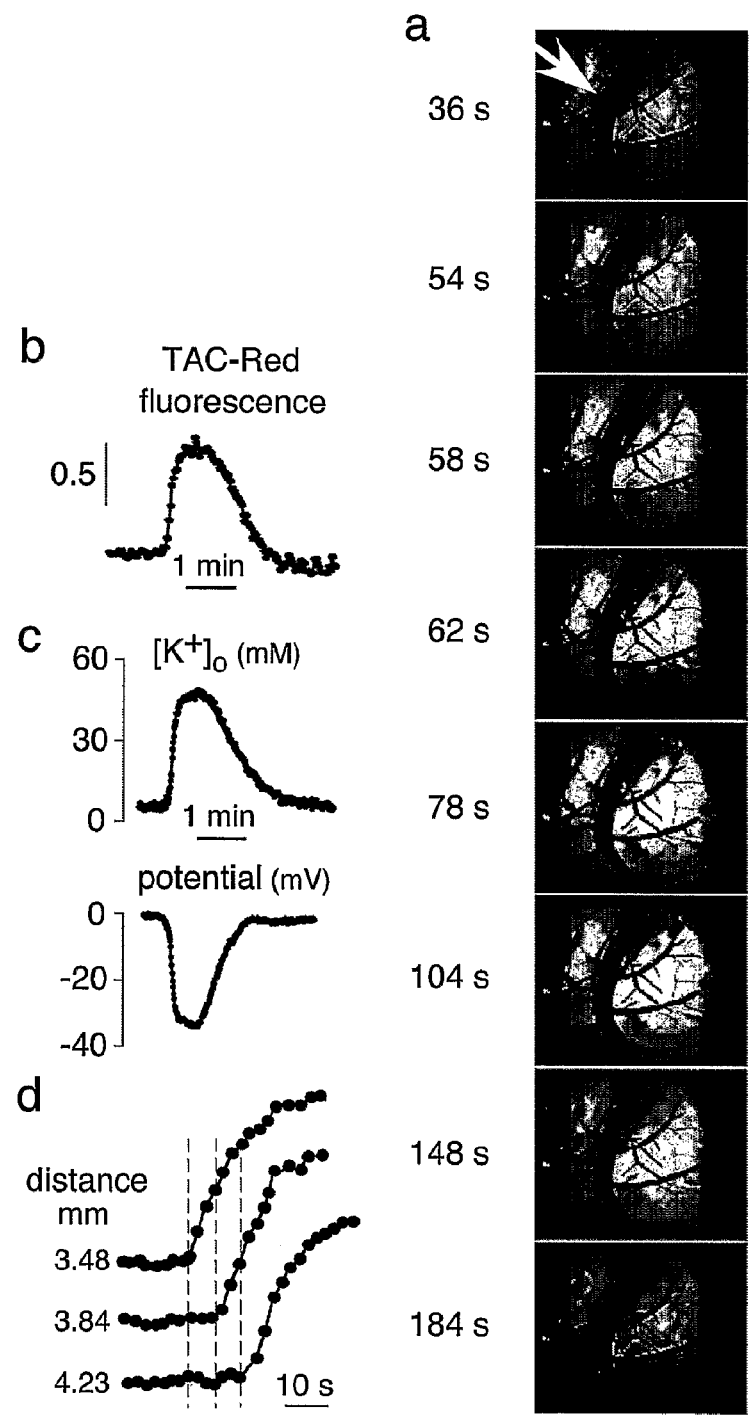
FIG. 2 provides data relating to visualization of extracellular space $K^+$ waves in spreading depression visualized at the brain surface in wild-type mice. The ECS in brain cortex was stained with TAC-Red through the dura. Panel a: Serial images of brain cortex at indicated times after initiation of spreading depression by mechanical stimulation. TAC-Red fluorescence is shown in grey scale, with increasing intensities scaled from black-dark grey-grey-light grey-white. Panel b: Representative time course of TAC-Red fluorescence at a single point. Panel c: [$K^+$]$_o$ (top) and field potential (bottom) measured using a double-barreled $K^+$-sensitive glass micropipette following initiation of spreading depression. Panel d: Expanded time courses shown at indicated locations from the site of initiation of spreading depression.

A mechanical stimulation (pin-prick) model of spreading depression produced propagating K$^+$ waves at the cortical surface. Exemplary frames of the video are provided (in grey scale) in FIG. 2, panel a, showing a wave of increasing [K$^+$]o propagating in the direction of the white arrow following mechanical stimulation about 3 mm proximal to the measurement site. Control studies showed no signal changes when a non-K$^+$-sensitive red fluorescent dye (sulforhodamine 101) was used in place of TAC-Red. FIG. 2, panel b shows a representative TAC-Red fluorescence time-profile at a fixed location. The increase in fluorescence had a half-time (t$_{1/2}$) of about 10 s, followed by a return to baseline with t$_{1/2}$ of about 30 s were shown in FIG. 3 panel b.

For comparison, separate studies were done using a double-barreled K$^+$-sensitive glass microelectrode inserted superficially in brain cortex. FIG. 2, panel c shows that the temporal patterns of [K$^+$]o and field potential were similar to those measured by TAC-Red fluorescence. The $K^+$ wave propagation velocity was 4.4±0.5 mm/min (SE, n=4 mice) as determined the temporal offset in profiles at different locations along the direction of wave advancement (FIG. 2, panel d).

Figure 3:
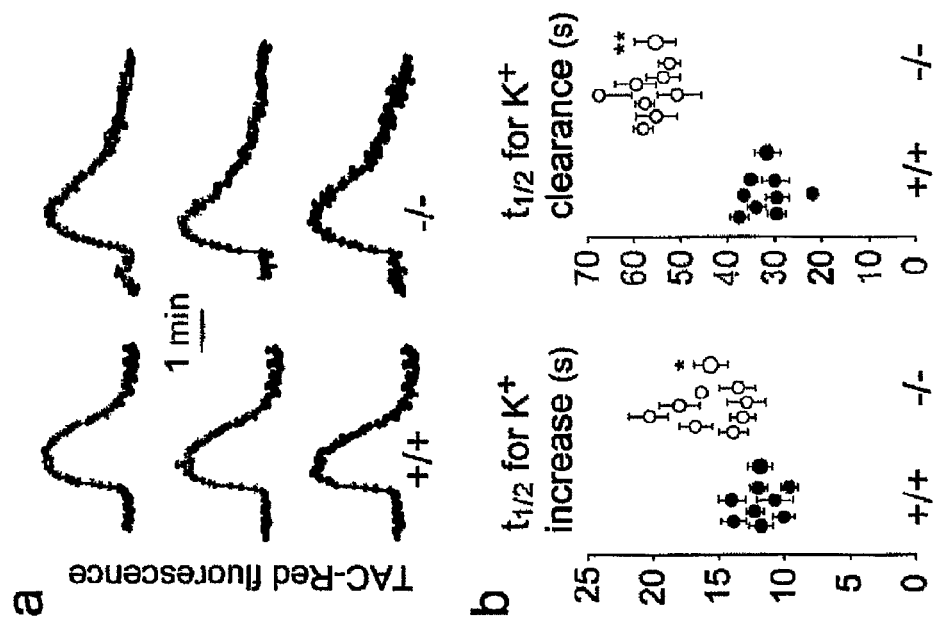
FIG. 3 provides data relating to the phenomena of slowed cellular $K^+$ release and reuptake in mice lacking astroglial water channel AQP4. Panel a: Time course of TAC-Red fluorescence in wild-type and AQP4 null mice following initiation of spreading depression. Panel b: Half-times ($t_{1/2}$) for the increase and return to baseline in TAC-Red fluorescence, representing cellular $K^+$ release and $K^+$ reuptake, respectively. Each point is the average (±SEM) of values from twelve different locations per mouse. Averaged data for n=8 mice shown (*$p<0.05$, **$p<0.001$).

Mice with primary or secondary deficiency in glial water channel AQP4 have increased seizure threshold and prolonged seizure duration (Binder et al. *Neuroreport* 15, 259-262 (2004); Amiry-Moghaddam et al. *Proc. Natl. Acad. Sci. USA* 100, 13615-13620 (2003)), and impaired evoked potential responses (Li et al. *J. Biol. Chem.* 276, 31233-31237 (2001)). To test whether AQP4 deficiency impairs the kinetics of cellular $K^+$ release into and/or reuptake, the kinetics of $[K^+]_o$ waves was compared in wildtype mice and AQP4 null mice. FIG. 3, panel a shows broader $K^+$ wave profiles in the AQP4-deficient mice. FIG. 3, panel b summarizes averaged $t_{1/2}$ values for the increasing (cellular $K^+$ release) and decreasing ($K^+$ reuptake) phases of the fluorescence profile. Though the $t_{1/2}$ for the fluorescence release phase was slightly greater in AQP4 null mice, the $t_{1/2}$ for the reuptake phase was remarkably greater (57 vs. 32 s, $p<0.001$).

The slowed elevation and return to baseline in $[K^+]_o$ in AQP4 null mice provides a possible explanation for the seizure and neural signaling phenotypes seen in AQP4 deficiency. The mildly slowed $K^+$ release into the ECS is likely related to the expanded brain ECS in AQP4 deficient mice, which was demonstrated by accelerated diffusion of fluorescently labeled dextrans in AQP4 deficiency (Binder et al. *J. Neurosci.* 24, 8049-8056 (2004)). The remarkably slowed $K^+$ reuptake from the ECS, which is largely a function of astroglia where AQP4 is expressed, likely represents an intrinsic impairment in astroglial $K^+$ reuptake in AQP4 deficiency. Impaired functioning of the inwardly rectifying $K^+$ channel Kir4.1 in AQP4-deficient astroglia has been proposed (Nagelhus, E. A. et al. *Glia* 26, 47-54 (1999); Eid, T. et al. *Proc. Natl. Acad. Sci. USA* 102, 1193-1198 (2005)), which may involve Kir4.1-AQP4 interactions (Connors et al. *J. Biol. Chem.* 279, 28387-28392 (2004)). These data thus provide evidence for altered $[K^+]_o$ dynamics in AQP4 deficiency, and are consistent with a mechanism involving impaired astroglial cell $K^+$ channel function secondary to disruption of AQP4-$K^+$ channel interactions.

This example illustrates that TAC-Red has many properties that make it useful for measurement of $K^+$ in biological environments. Its long-wavelength excitation and bright fluorescence minimizes background cellular fluorescence, interference by hemoglobin oxygenation, and light-induced injury and photobleaching. Its fluorescence is highly sensitive to $K^+$ in the range 0 to >100 mM, which is an expected range of $K^+$ concentrations found in extracellular and intracellular fluidic compartments. TAC-Red fluorescence is minimally affected by $Na^+$ and not sensitive to other biologically-relevant cations or anions, or to pH in the physiological range. The large triazacryptand moiety and the relatively polar rosamine chromophore render TAC-Red water soluble and membrane-impermeable, and thus suitable for $K^+$ measurements in many types of extracellular fluid compartments.

Example 13

TAC-Red as an Indicator for Measurement of $K^+$ Channel Function for High-Throughput Screening Applications Fluorescence microscopy: For most experiments cells on coverslips were incubated in 1 ml high $K^+$ buffer for 2 min prior to experiments. Ionophore(s) (valinomycin and/or SQI-Et) were incorporated into cell plasma membrane by addition from 10 mM stock solutions in the presence of 0.01% Pluronic F127 while vortexing for 15 to 20 s, followed by further incubation for 5 min. Just prior to measurement cells were washed thoroughly and rapidly (<10 s) with 0 $K^+$ buffer (or 0 $Na^+$ 0 $K^+$ buffer). Measurements were performed by placing a 10 μl droplet of 0 $K^+$ buffer (or 0 $Na^+$ 0 $K^+$ buffer) containing TAC-Red (150 μM) on a glass slide on the stage of an inverted epifluorescence microscope (Nikon Diaphot). The washed cells were immediately placed cell-side down on the slide and fluorescence measured continuously. TAC-Red fluorescence was excited at 545±30 nm and detected through a 610±75 nm filter (570 nm dichroic) using a long working distance 25× air objective lens.

Plate reader assay: Measurements were done using a Fluostar plate reader (BMG LabTechnologies) with syringe pump for automated solution addition. Cells were incubated with valinomycin (10 μM) in $Na^+$ $K^+$ buffer for 5 min at 37° C., extracellular buffer was withdrawn, and cells were briefly washed with 0 $K^+$ buffer. The plate was loaded onto plate reader and after 6 s of fluorescence measurement 30 μl of TAC-Red (150 μM) in 0 $K^+$ buffer was added via syringe pump. TAC-Red fluorescence was excited using an HQ545/30 filter (Chroma) and emitted fluorescence was detected through a HQ585/30 filter.

Figure 4:
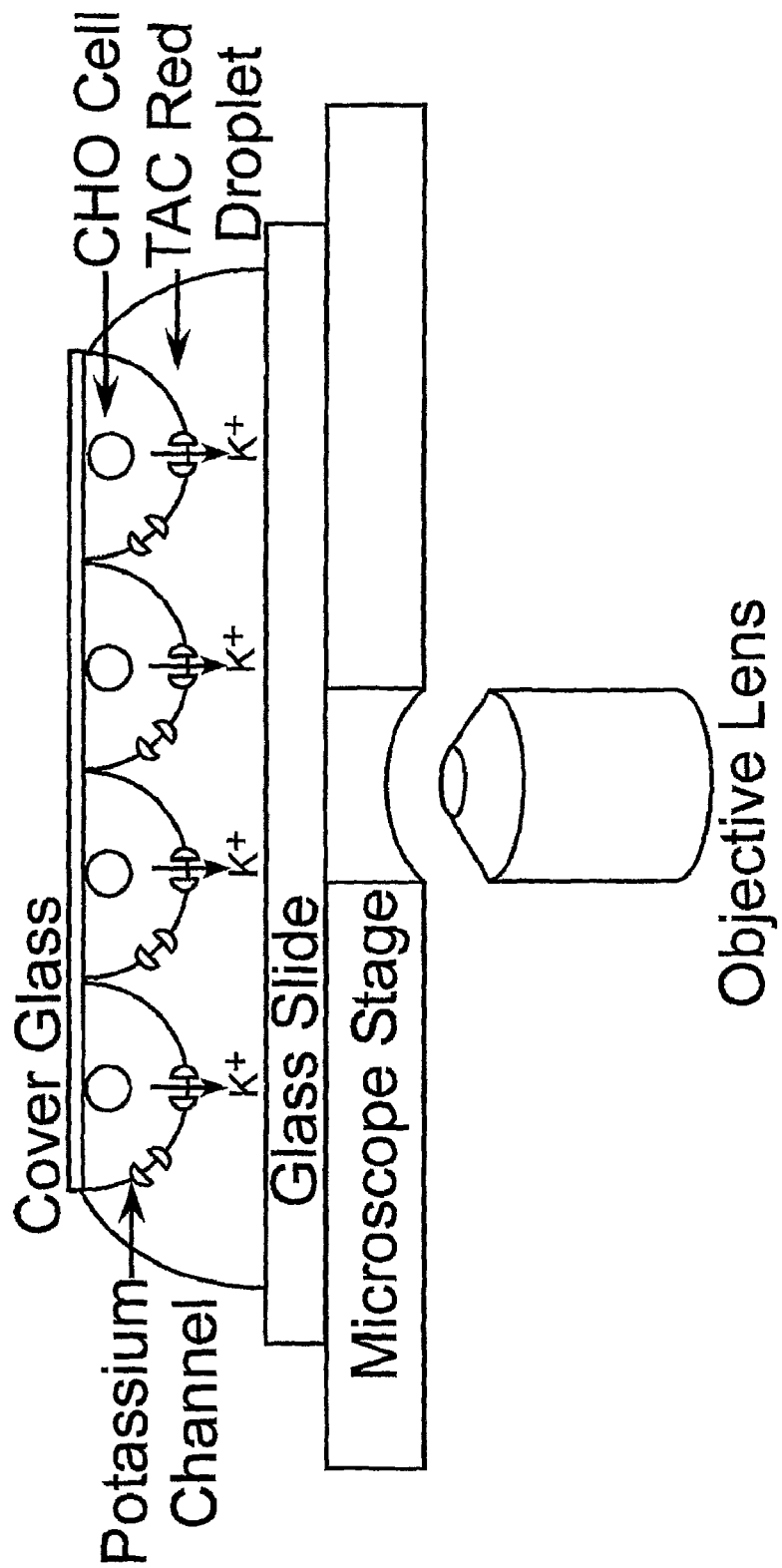
FIG. 4 illustrates a schematic of a system for cell fluorescence measurements.

The schematic for cell fluorescence measurements is shown in FIG. 4. TAC-Red was used as an indicator of extracellular $K^+$, such that the rate of initial $K^+$ efflux into a 0 $K^+$ buffer could be measured. The experimental design involved cell washing with a 0 $K^+$ buffer at which time the washed cells contacted a TAC-Red solution in a 0 $K^+$ buffer. In some experiments the $K^+$ ionophore valinomycin was used to increased cell plasma membrane $K^+$ permeability, and/or the $Na^+$ ionophore SQI-Et was used to increase membrane $Na^+$ conductance to provide a conductive counterion pathway.

Figure 5:
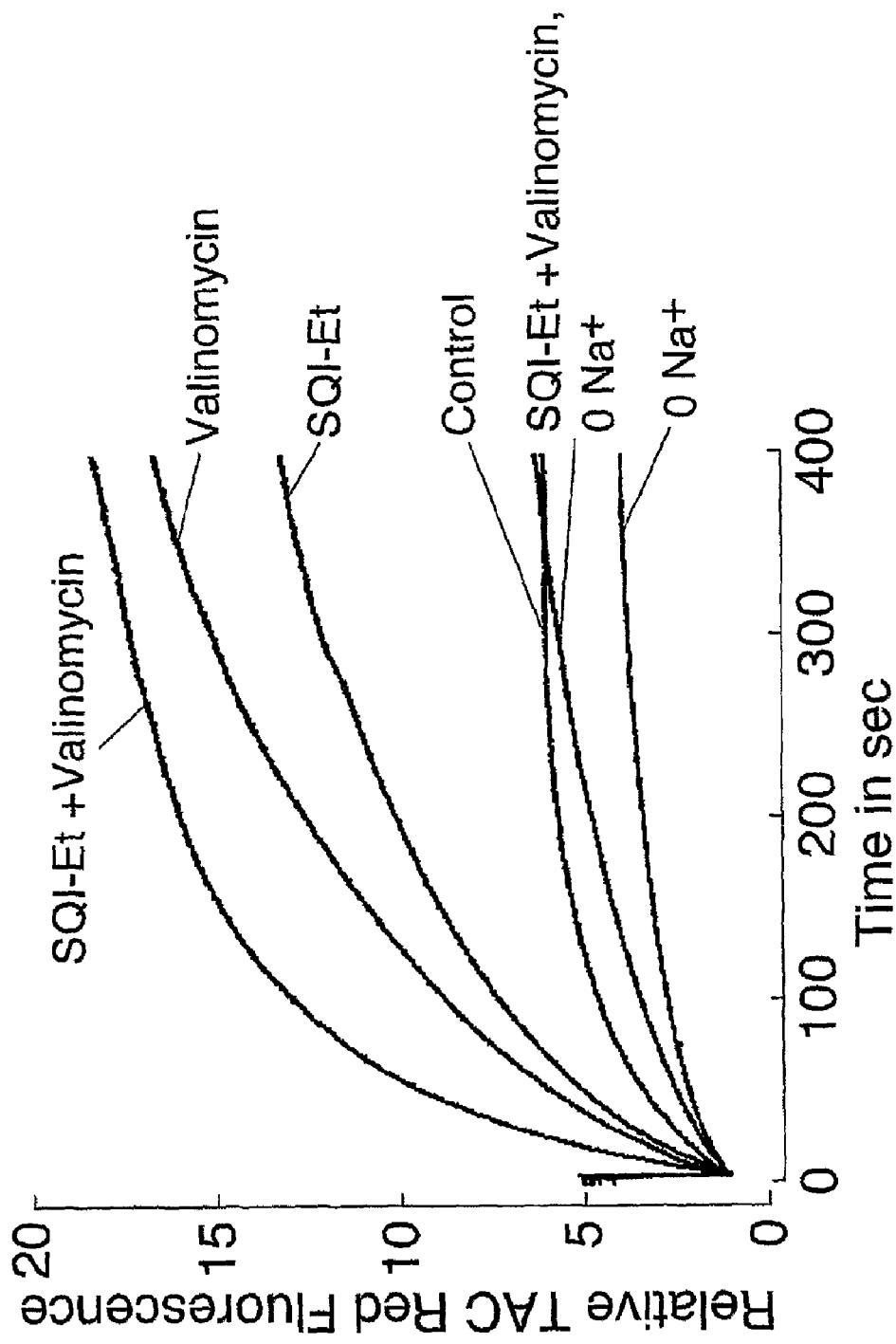
FIG. 5 illustrates $K^+$ efflux in CHO cells measured by TAC-Red fluorescence. Time course of extracellular TAC-Red fluorescence measured using an inverted epifluorescence microscope. Data shown for "control"—untreated cells washed and measured in 0 $K^+$ buffer, "SQI-Et"—cells treated with 10 µM SQI-Et then washed and measured in 0 $K^+$ buffer, "Valinomycin"—cells treated with 10 µM valinomycin then washed and measured in 0 $K^+$ buffer, "SQI-Et-valinomycin"—cells treated with 10 µM SQI-Et plus 10 µM valinomycin then washed and measured in 0 $K^+$ buffer, "SQI-Et-valinomycin, 0 $Na^+$"—cells treated with 10 µM SQI-Et plus 10 µM valinomycin then washed and measured in 0 $Na^+$ 0 $K^+$ buffer. "0 $Na^+$"—untreated cells washed and measured in 0 $Na^+$ 0 $K^+$ buffer.
Figure 6:
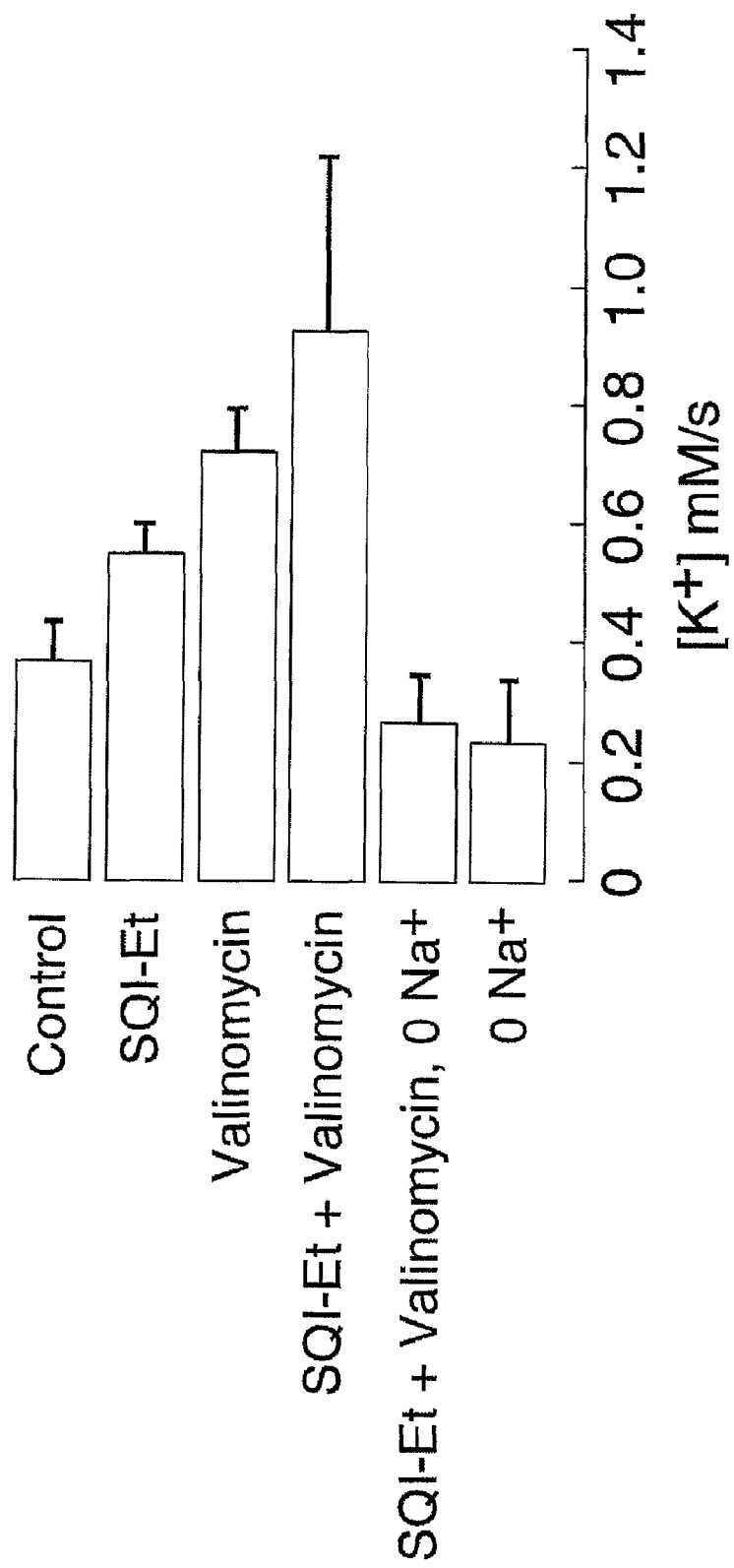
FIG. 6 illustrates $K^+$ efflux rate in mM/sec measured from the initial slope (10 s) of fluorescence increase by fluorescence measurements indicated in FIG. 5. (Error bars represent s.d., n=3).

FIG. 5 shows the kinetics of TAC-Red fluorescence increase indicating $K^+$ efflux from CHO cells. Addition of the cell-containing coverglass produced an initial decrease in measured fluorescence as the 10 μl droplet thinned, followed by fluorescence increase due to $K^+$ efflux. FIG. 6 shows deduced rates of $K^+$ efflux from initial slopes.

Pre-incubation with valinomycin increased $K^+$ efflux, indicating the ability to measure plasma membrane $K^+$ conductance. Replacement of extracellular $Na^+$ by choline$^+$ reduced $K^+$ efflux because $Na^+$ is the principal counterion that moves into the cell to maintain electroneutrality to allow $K^+$ efflux. Increasing plasma membrane $Na^+$ conductance by SQI-Et increases $K^+$ efflux if membrane $Na^+$ conductance is relatively low compared to $K^+$ conductance, in which case $Na^+$ conductance can be rate-limiting.

Figure 7:
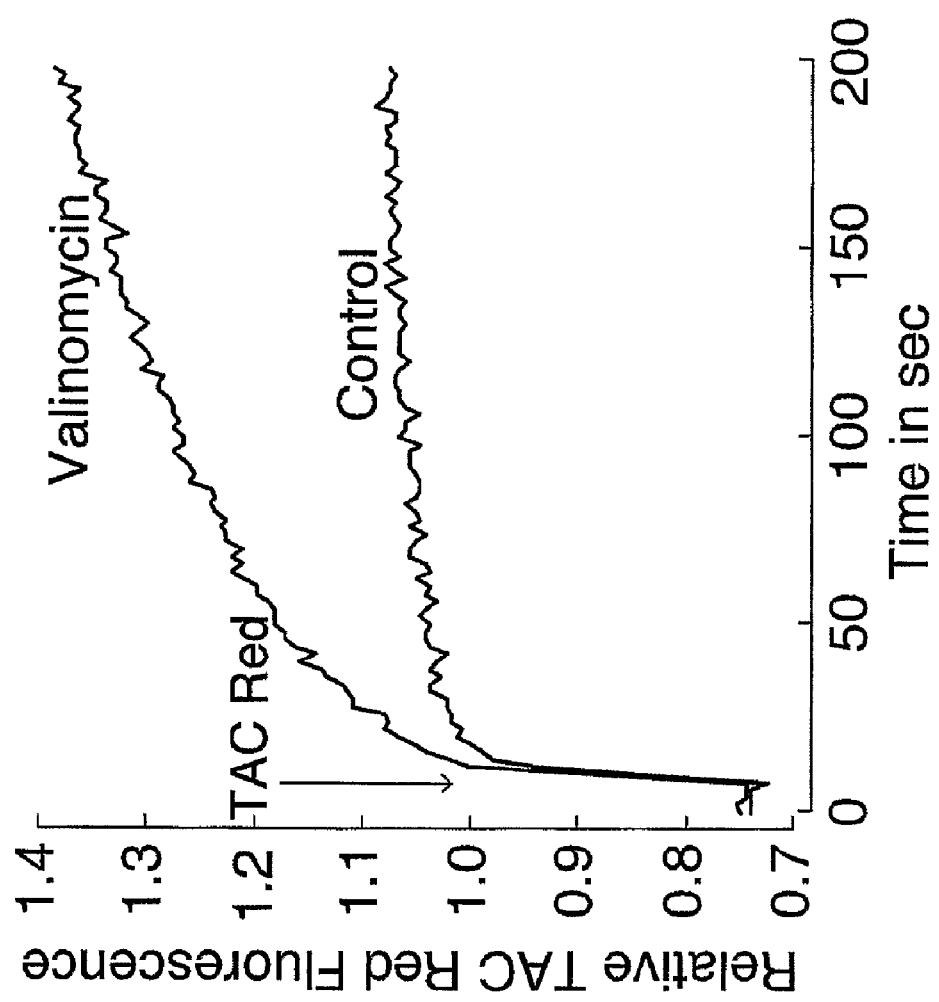
FIG. 7 illustrates TAC-Red in control and valinomycin-treated cells measured in a commercial fluorescence plate reader.

FIG. 7 shows a similar measurement done using a commercial fluorescence plate reader. Preincubation of cells with valinomycin increased $K^+$ efflux as seen from the increase in TAC-Red fluorescence.

What is claimed is:

1. A potassium-sensitive chromoionophore comprising the formula:

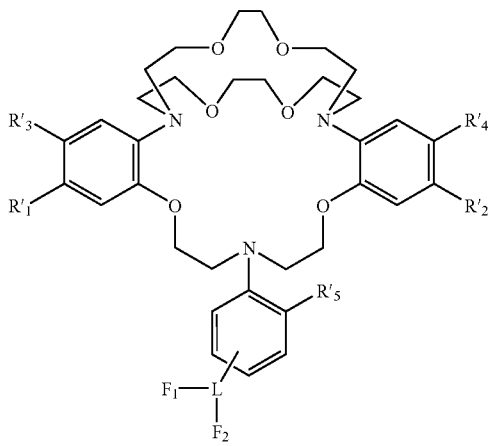

wherein $F_1$ and $F_2$ each represent a chromophoric moiety, where $F_2$ may be present or absent;

$R'_1$ and $R'_2$ are lower alkyls and $R'_3$ and $R'_4$ independently selected from H or a lower alkyl; or, when $F_2$ is absent, $R'_1$ and $R'_2$ are independently selected from a lower alkyl or $F_3$, and $R'_3$ and $R'_4$ are independently H or lower alkyls; or when $F_2$ is absent, $R'_1$ and $R'_2$ are lower alkyls, and $R'_3$ and $R'_4$ are independently selected from a lower alkyl or $F_3$, wherein $F_3$ is of the formula $$X'—P_H—F'_3$$

where

X' is a reactive group, selected from an amine, amide, succinimidyl ester, or aldehyde, $P_H$ is selected from a hydrophilic, water-soluble polymer; and $F'_3$ is a chromophoric moiety insensitive to pH and to potassium binding by the chromoionophore, where $F'_3$ provides a detectable signal that is different from a detectable signal of $F_1$;

$R'_5$ is a substituted or unsubstituted alkyl, alkoxy, alkoxyalkyl, alkoxyaryl, t-alkyl ester of carboxyalkoxy, t-alkyl ester of carboxyalkoxyalkoxy, succinimidylester of carboxyalkoxy, succinimidylester of carboxyalkoxyalkoxy, aminoalkoxy, aminoalkoxyalkoxy, mercaptoalkoxy, or mercaptoalkoxyalkoxy;

L is a linker selected from a substituted or unsubstituted lower alkyl of the formula $—(CH_2)_v—$ or $—(CH_2)_w—NH—$, where v is 0, 1, or 2 and w is 1 or 2; a substituted phenyl group; or a bifunctional group; and $F_1$ is a chromophoric moiety which provides a detectable fluorescent signal upon excitation when potassium is bound to the ionophore, wherein when $F_2$ and $F_3$ are absent, $F_1$ comprises the formula:

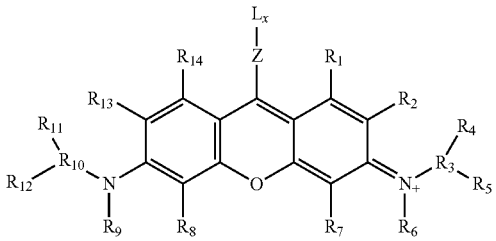

where $L_x$ indicates binding to the linker L;

$R_1$ and $R_{14}$ are each independently selected from H or a lower alkyl;

$R_2$ and $R_{13}$ are each independently selected from H or a lower alkyl unless:

$R_2$ and $R_{13}$ are joined to form substituted or unsubstituted quinolizine ring systems that include $R_3$, $R_6$, and $R_7$, and $R_8$, $R_9$, and $R_{10}$, respectively, to provide one or two quinolizine ring systems in the compound; or $R_2$ and $R_{13}$ are joined to form in the compound pyridine or thieno-pyridine ring systems that include $R_3$ and $R_{10}$, respectively, to provide one or two pyridine ring systems or one or two thieno-pyridine ring systems in the compound, and wherein the thieno-pyridine ring systems are thieno-quinoline ring systems;

wherein when $R_2$ and $R_{13}$ are present in ring structures, at least one of the ring structures contains a positively charged amine, and when $R_2$ and $R_{13}$ are joined to form one or two pyridine ring systems that include $R_3$ and $R_{10}$, respectively, the pyridine ring systems are substituted by a methylene or polymethylene group that is substituted by an anionic moiety;

$R_4$, $R_5$, $R_{11}$, and $R_{12}$ are independently selected from H or a lower alkyl, and are present when $R_2$ and $R_{13}$ are joined in a ring structure with $R_3$ and $R_{10}$, respectively, otherwise $R_4$, $R_5$, $R_{11}$, and $R_{12}$ are absent;

$R_3$, $R_6$, $R_9$, and $R_{10}$ are independently selected from a lower alkyl if "N" is not part of a ring structure; and $R_7$ and $R_8$ are independently selected from H or a lower alkyl if $R_7$ and $R_8$ are not part of a ring structure with $R_6$ and $R_9$, respectively; and Z is of the formula:

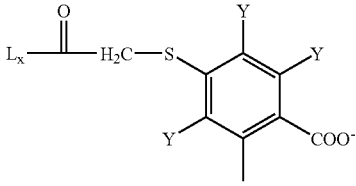

wherein Y are each independently halides, and $L_x$ indicates binding to the linker L, and Z is present when $R_2$ and $R_{13}$ are joined to form pyridine ring systems that include $R_3$ and $R_{10}$, respectively; and $F_2$, when present, is of the formula $X—P_H—F_2'$, where X is an alkyl benzamide, succinimidyl ester, or aldehyde;

$P_H$ is a hydrophilic, water-soluble polymer, and $F_2$ is a chromophoric moiety that provides a stable detectable signal insensitive to potassium binding and pH, where $F'_2$ provides a detectable signal distinguishable from the detectable signal of $F'_1$;

and pharmaceutically acceptable salts thereof.

2. The chromoionophore of claim 1, wherein R'$_5$ is of the formula:

—[OCH$_2$CH$_2$]$_n$OCH$_3$;

—[OCH$_2$CH$_2$]$_n$O—(CH$_2$)$_m$—COO-t-butyl;

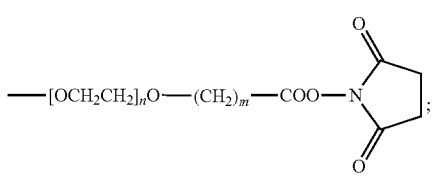

—[OCH$_2$CH$_2$]$_n$O—(CH$_2$)$_m$—NH$_2$; or

—[OCH$_2$CH$_2$]$_n$O—(CH$_2$)$_m$—SH n is 0 or 1, and m is an integer from 1 to 6.

3. The chromoionophore of claim 1, wherein P$_H$ of X'—P$_H$—F'$_3$ or X—P$_H$—F'$_2$ is dextran, polyethylene oxide, polyethyleneimine (PEI), polylactide, polyglycolide, or polylactic polylactide glycolide acid (PLGA).

4. The chromoionophore of claim 1, wherein an X' of the formula X'—P$_H$—F'$_3$ or X or the formula X—P$_H$—F'$_2$ is

[CH$_2$]$_q$O—(CH$_2$)$_s$—CO—NH— or —O—[CH$_2$]$_s$—CO—NH— wherein q is an integer from 1 to 2; and s is an integer from 2 to 6.

5. The chromoionophore of claim 1, wherein F$_2$ is absent, R'$_1$ and R'$_2$ are lower alkyls, R'$_3$ and R'$_4$ are H or lower alkyls, and F$_1$ comprises the formula:

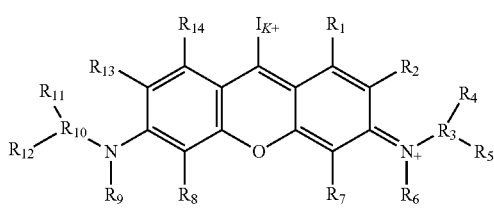

(II)

where:
R$_1$ and R$_{14}$ are each independently selected from H or a lower alkyl;
R$_2$ and R$_{13}$ are each independently selected from H or a lower alkyl unless:
R$_2$ and R$_{13}$ are joined to form substituted or unsubstituted quinolizine ring systems that include R$_3$, R$_6$, and R$_7$, and R$_8$, R$_9$, and R$_{10}$, respectively, to provide one or two quinolizine ring systems in the compound; or
R$_2$ and R$_{13}$ are joined to form in the compound pyridine or thieno-pyridine ring systems that include R$_3$ and R$_{10}$, respectively, to provide one or two pyridine ring systems or one or two thieno-pyridine ring systems in the compound, and wherein the thieno-pyridine ring systems are thieno-quinoline ring systems;
wherein when R$_2$ and R$_{13}$ are present in ring structure, at least one of the ring structures contains a positively charged amine;
R$_4$, R$_5$, R$_{11}$, and R$_{12}$ are independently selected from H or a lower alkyl, and are present when R$_2$ and R$_{13}$ are joined in a ring structure with R$_3$ and R$_{10}$, respectively, otherwise R$_4$, R$_5$, R$_{11}$, and R$_{12}$ are absent;
R$_3$, R$_6$, R$_9$, and R$_{10}$ are independently selected from a lower alkyl if "N" is not part of a ring structure;
R$_7$ and R$_8$ are independently selected from H or a lower alkyl if R$_7$ and R$_8$ are not part of a ring structure with R$_6$ and R$_9$, respectively; and
I$_{K+}$ represents the position of binding to the ionophore through L.

6. The chromoionophore of claim 5, wherein
R$_1$, R$_2$, R$_7$, R$_8$, R$_{13}$, and R$_{14}$ are each independently selected from H or a lower alkyl;
R$_3$, R$_6$, R$_9$, and R$_{10}$ are independently selected from a lower alkyl; and
R$_4$, R$_5$, R$_{11}$, and R$_{12}$ are absent.

7. The chromoionophore of claim 5, wherein
R$_1$ and R$_{14}$ are each independently selected from H or a lower alkyl;
R$_2$ and R$_{13}$ are joined to form quinolizine ring systems that include R$_3$, R$_6$, and R$_7$, and R$_8$, R$_9$, and R$_{10}$, respectively, to provide one or two quinolizine ring systems in the compound; and R$_4$, R$_5$, R$_{11}$, and R$_{12}$ are independently selected from H or a lower alkyl.

8. The chromoionophore of claim 5, wherein:
R$_1$ and R$_{14}$ are each independently selected from H or a lower alkyl;
R$_2$ and R$_{13}$ are joined to form in the compound pyridine or thieno-pyridine ring systems that include R$_3$ and R$_{10}$, respectively, to provide one or two pyridine ring systems or one or two thieno-pyridine ring systems in the compound, and wherein the thieno-pyridine ring systems are thieno-quinoline ring systems; and
R$_4$, R$_5$, R$_{11}$, and R$_{12}$ are independently selected from H or a lower alkyl.

9. The chromoionophore of claim 1, wherein R'$_1$ and R'$_2$ are each methyl, and R'$_5$ is —O(CH$_2$)$_2$O—CH$_3$.

10. The chromoionophore of claim 8, wherein F$_2$ is absent.

11. The chromoionophore of claim 10, wherein F$_1$ is in the para position.

12. The chromoionophore of claim 1, wherein the chromoionophore comprises the formula:

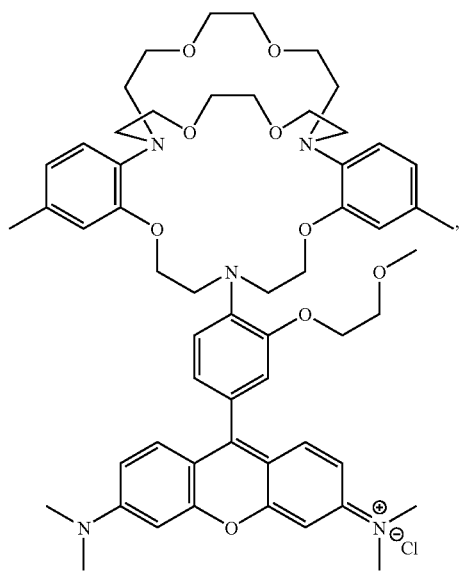

-continued

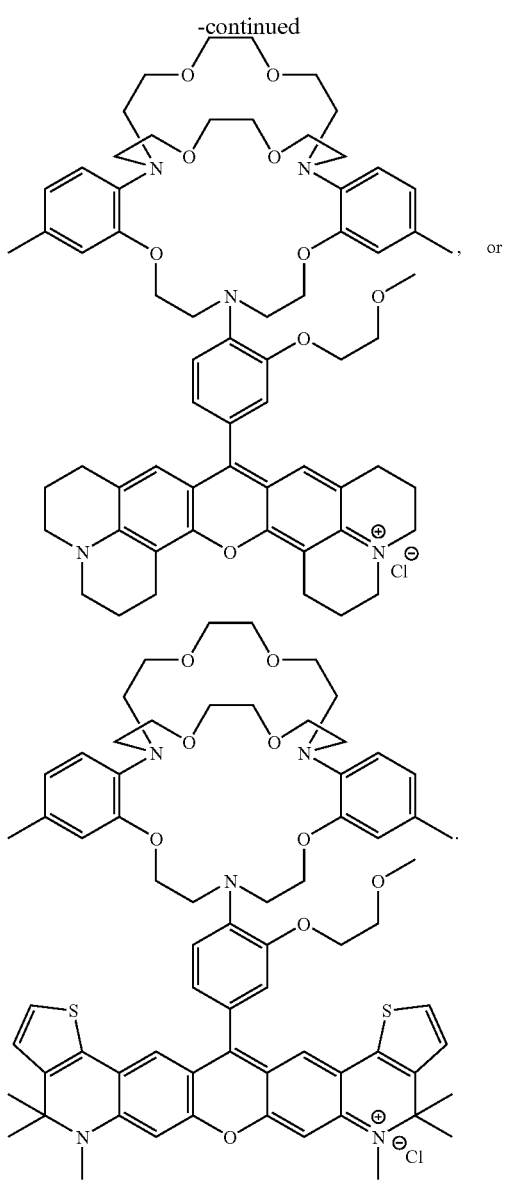

13. A potassium-sensitive chromoionophore comprising the formula:

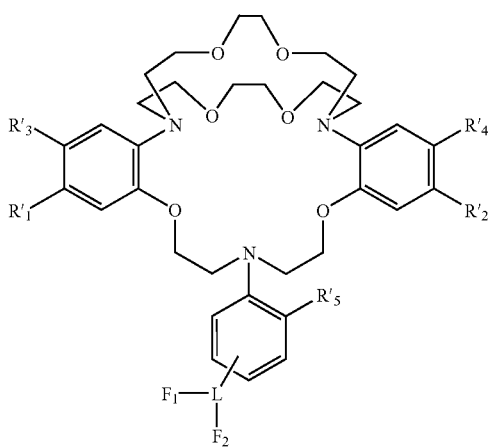

wherein

F$_1$ and F$_2$ each represent a chromophoric moiety, where F$_2$ may be present or absent;

R'$_1$ and R'$_2$ are lower alkyls and R'$_3$ and R'$_4$ independently selected from H or a lower alkyl; or, when F$_2$ is absent, R'$_1$ and R'$_2$ are independently selected from a lower alkyl or F$_3$, and R'$_3$ and R'$_4$ are independently H or lower alkyls; or when F$_2$ is absent, R'$_1$ and R'$_2$ are lower alkyls, and R'$_3$ and R'$_4$ are independently selected from a lower alkyl or F$_3$, wherein F$_3$ is of the formula

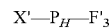

where X' is a reactive group, selected from an amine, amide, succinimidyl ester, or aldehyde; P$_H$ is selected from a hydrophilic, water-soluble polymer; and F'$_3$ is a chromophoric moiety insensitive to pH and to potassium binding by the chromoionophore, where F'$_3$ provides a detectable signal that is different from a detectable signal of F$_1$;

R'$_5$ is a substituted or unsubstituted alkyl, alkoxy, alkoxyalkoxy, alkoxyaryl, t-alkyl ester of carboxyalkoxy, t-alkyl ester of carboxyalkoxyalkoxy, succinimidylester of carboxyalkoxy, succinimidylester of carboxyalkoxyalkoxy, aminoalkoxy, aminoalkoxyalkoxy, mercaptoalkoxy, or mercaptoalkoxyalkoxy;

L is a linker selected from a substituted or unsubstituted lower alkyl of the formula —(CH$_2$)$_v$— or —(CH$_2$)$_w$—NH—, where v is 0, 1, or 2 and w is 1 or 2; and F$_1$ is a chromophoric moiety which provides a detectable fluorescent signal upon excitation when potassium is bound to the ionophore, wherein when F$_2$ and F$_3$ are absent, F$_1$ is selected from a moiety of the formula:

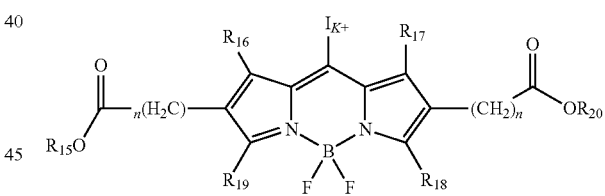

where:

each of R$_{15}$, R$_{16}$, R$_{17}$, R$_{18}$, R$_{19}$ and R$_{20}$ is independently selected from H or lower alkyl, and wherein R$_{15}$ and R$_{20}$ are further independently selected from an alkali metal cation, n is an integer from 0 to 6;

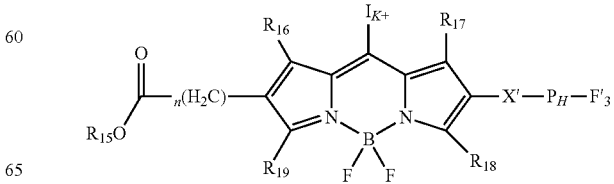

where:
each of $R_{15}$, $R_{16}$, $R_{17}$, $R_{18}$, and $R_{19}$ is independently selected from H or lower alkyl, and wherein $R_{15}$ is further independently selected from an alkali metal cation,
n is an integer from 0 to 6;
$I_{K+}$ represents the position of binding to the ionophore through L; and

X'—$P_H$—F'$_3$ is defined above; and

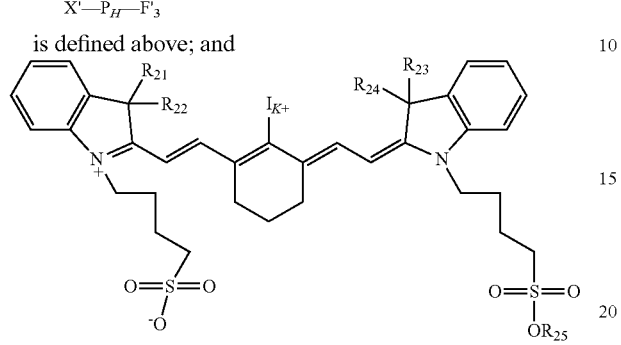

where:
each of $R_{21}$, $R_{22}$, $R_{23}$, $R_{24}$, and $R_{25}$ is independently selected from H or lower alkyl, and $R_{25}$ is further independently selected from an alkali metal cation,
n is an integer from 0 to 6; and
$I_{K+}$ represents the position of binding to the chromoionophore through L; and
$F_2$, when present, is of the formula X—$P_H$—$F_2'$, where X is an alkyl benzamide, succinimidyl ester, or aldehyde;
$P_H$ is a hydrophilic, water-soluble polymer, and
$F'_2$ is a chromophoric moiety that provides a stable detectable signal insensitive to potassium binding and pH, where $F'_2$ provides a detectable signal distinguishable from the detectable signal of $F'_1$;
and pharmaceutically acceptable salts thereof.

14. The chromoionophore of claim 13, wherein X' of the formula X'—$P_H$—$F'_3$ or X or the formula X—$P_H$—$F'_2$ is —[CH$_2$]$_q$O—(CH$_2$)$_s$—CO—NH—,
—O—[CH$_2$]$_s$-CO—NH—, or —[CH$_2$]$_s$-CO—NH—,
where q is an integer from 1 to 2 and s is an integer from 2 to 6.

15. The chromoionophore of claim 13, wherein the chromoionophore comprises the formula:

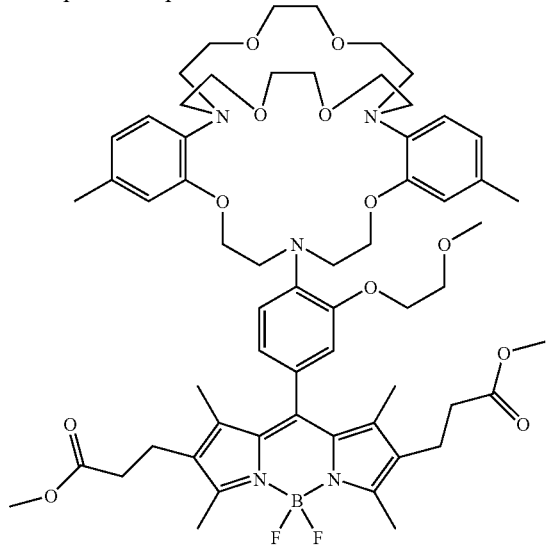

16. The chromoionophore of claim 13, wherein the chromoionophore comprises the formula:

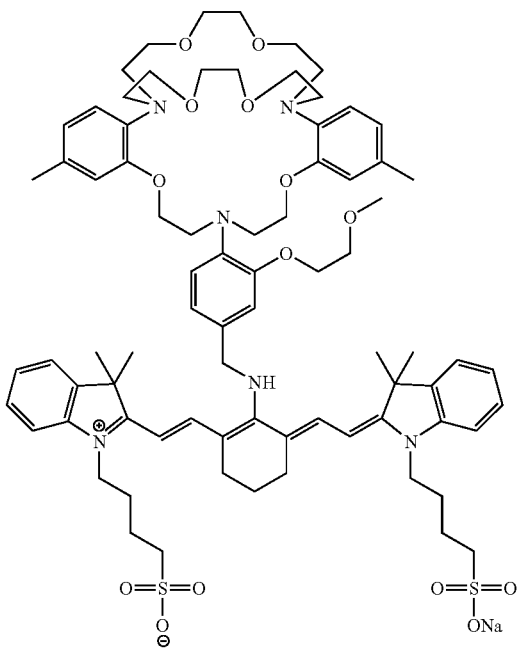

17. A potassium-sensitive chromoionophore comprising a conjugate of an ionophoric moiety, a first chromophoric moiety and a second chromophoric moiety, the chromoionophore comprising the formula:

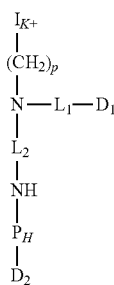

where
$I_{K+}$ is a triazacryptand (TAC) ionophoric moiety;
p is 0, 1 or 2;
$L_1$ is a first linker selected from a substituted aryl group, an unsubstituted aryl group or —CO—(CH2)-COO-t-butyl;
$L_2$ is a second linker selected from a substituted or unsubstituted aryl group;
$P_H$ is a hydrophilic, water soluble polymer; and
$D_1$ and $D_2$ are different chromophoric moieties having detectably distinct emission wavelengths, where $D_1$ is potassium sensitive chromophoric moiety and $D_2$ is a potassium insensitive chromophoric moiety.

18. The chromoionophore of claim 17, wherein:
p is 1;
$L_1$ and $L_2$ are independently a substituted or unsubstituted phenyl group; and
$P_H$ is bound to $L_2$ through a nitrogen of an amide group.

19. The chromoionophore of claim 18, wherein $L_1$ and $L_2$ are unsubstituted phenyl groups.

20. The chromoionophore of claim 17, wherein the compound is of the formula:

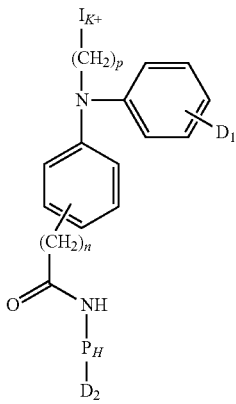

where
$I_{K+}$ is a triazacryptand (TAC) ionophoric moiety;
n and p are independently selected from 0, at least 1, or at least 2;
$P_H$ is a water soluble polymer, wherein $L_2$ and $P_H$ are covalently bound through a secondary amine; and
$D_1$ and $D_2$ are different chromophoric moieties having detectably distinct emission wavelengths, where $D_1$ is potassium sensitive chromophoric moiety and $D_2$ is a potassium insensitive chromophoric moiety.

21. The chromoionophore of claim 17, wherein $D_1$ comprises the formul:

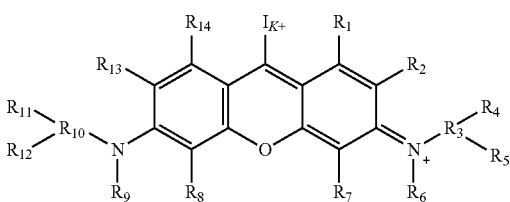

where
$I_{K+}$ represents a covalent linkage to the ionophore;
$R_1$ and $R_{14}$ are each independently selected from H or a lower alkyl;
$R_2$ and $R_{13}$ are each independently selected from H or a lower alkyl unless:
$R_2$ and $R_{13}$ are joined to form substituted or unsubstituted quinolizine ring systems that include $R_3$, $R_6$, and $R_7$, and $R_8$, $R_9$, and $R_{10}$, respectively, to provide one or two quinolizine ring systems in the compound; or
$R_2$ and $R_{13}$ are joined to form in the compound pyridine or thieno-pyridine ring systems that include $R_3$ and $R_{10}$, respectively, to provide one or two pyridine ring systems or one or two thieno-pyridine ring systems in the compound, and wherein the thieno-pyridine ring systems are thieno-quinoline ring systems;

wherein when $R_2$ and $R_{13}$ are present in ring structures, at least one of the ring structures contains a positively charged amine, and when $R_2$ and $R_{13}$ are joined to form pyridine ring systems that include $R_3$ and $R_{10}$, respectively, the pyridine ring systems are substituted by a methylene or polymethylene group that is substituted by an anionic moiety;

$R_4$, $R_5$, $R_{11}$, and $R_{12}$ are independently selected from H or a lower alkyl, and are present when $R_2$ and $R_{13}$ are joined in a ring structure with $R_3$ and $R_{10}$, respectively, otherwise $R_4$, $R_5$, $R_{11}$, and $R_{12}$ are absent;

$R_3$, $R_6$, $R_9$, and $R_{10}$ are independently selected from a lower alkyl if "N" is not part of a ring structure; and $R_7$ and $R_8$ are independently selected from H or a lower alkyl if $R_7$ and $R_8$ are not part of a ring structure with $R_6$ and $R_9$, respectively.

22. The chromoionophore of claim 21, wherein
$R_1$, $R_2$, $R_7$, $R_8$, $R_{13}$, and $R_{14}$ are each independently selected from H or a lower alkyl;
$R_3$, $R_6$, $R_9$, and $R_{10}$ are independently selected from a lower alkyl; and
$R_4$, $R_5$, $R_{11}$, and $R_{12}$ are absent.

23. The chromoionophore of claim 22, wherein
$R_1$ and $R_{14}$ are each independently selected from H or a lower alkyl;
$R_2$ and $R_{13}$ are joined to form quinolizine ring systems that include $R_3$, $R_6$, and $R_7$, and $R_8$, $R_9$, and $R_{10}$, respectively, to provide one or two quinolizine ring systems in the compound; and
$R_4$, $R_5$, $R_{11}$, and $R_{12}$ are independently selected from H or a lower alkyl.

24. The chromoionophore of claim 22, wherein:
$R_1$ and $R_{14}$ are each independently selected from H or a lower alkyl;
$R_2$ and $R_{13}$ are joined to form in the compound pyridine or thieno-pyridine ring systems that include $R_3$ and $R_{10}$, respectively, to provide one or two pyridine ring systems or one or two thieno-pyridine ring systems in the compound, and wherein the thieno-pyridine ring systems are thieno-quinoline ring systems; and
$R_4$, $R_5$, $R_{11}$, and $R_{12}$ are independently selected from H or a lower alkyl.

25. The chromoionophore of claim 17, wherein $D_1$ comprises the formula:

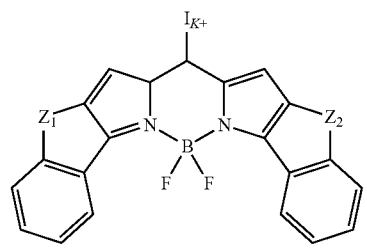

where $Z_1$ and $Z_2$ are O or S, and $I_{K+}$ represents the position of covalent attachment to $L_1$.

26. The chromoionophore of claim 17, where the TAC ionophoric moiety comprises the formula:

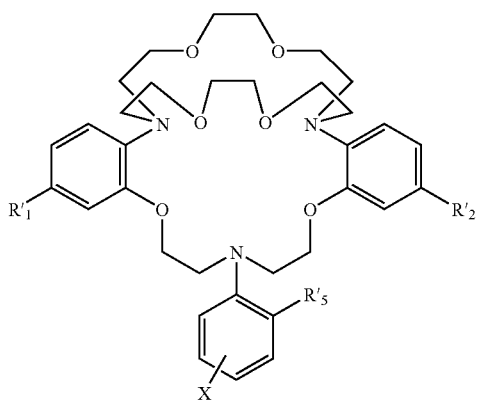

where: $R'_1$, $R'_2$ are independently H or a lower alkyl;
$R'_5$ is —[OCH$_2$CH$_2$]$_n$OCH$_3$, where n=1, and
X represents the position at which the TAC ionophoric moiety is bound in the chromoionophore.

27. The chromoionophore of claim 26, wherein the TAC ionophoric moiety comprises the formula:

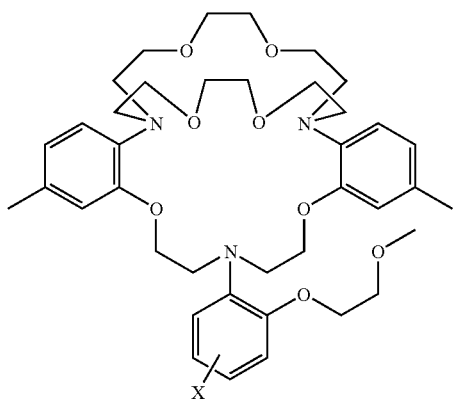

where X represents the position at which the TAC ionophoric moiety is bound in the chromoionophore.

28. The compound of claim 21, wherein the TAC ionophoric moiety is bound in the chromoionophore in the para position relative to the amine group.

29. The chromoionophore of claim 17, wherein the chromoionophore comprises the formula:

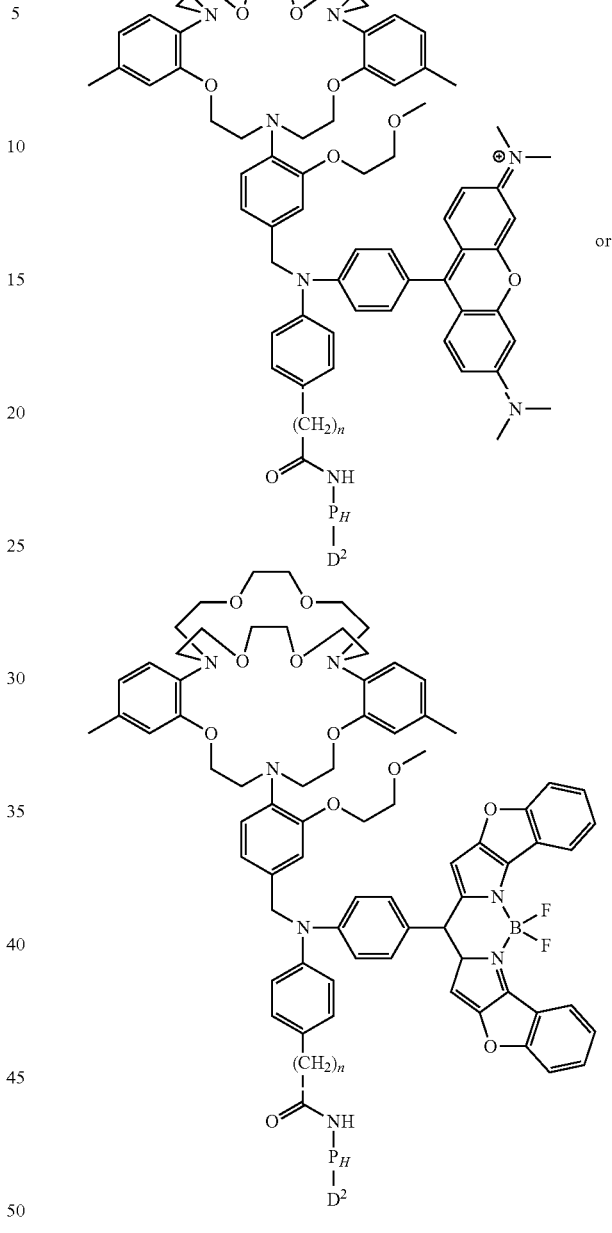

where
n is 0 or at least 1;
$P_H$ is a water soluble polymer; and
$D_2$ is a chromophoric moiety having a emission wavelength different from the chromophoric moiety at position $D_1$.

30. A potassium-sensitive chromoionophore comprising a conjugate of an ionophoric moiety, a first chromophoric moiety and a second chromophoric moiety, the chromoionophore comprising the formula:

$$I_{K+}\text{—}(CH_2)_p\text{-}D_1\text{-}(CH_2)_p\text{—}NH\text{—}P_H\text{-}D_2$$

where
$I_{K+}$ is a triazacryptand (TAC) ionophoric moiety;
p is 0, 1 or 2;
$P_H$ is a hydrophilic, water soluble polymer; and $D_1$ and $D_2$ are different chromophoric moieties having detectably distinct emission wavelengths, where $D_1$ is potassium sensitive chromophoric moiety and $D_2$ is a potassium insensitive chromophoric moiety.

31. The chromoionophore of claim 30, wherein the TAC ionophoric moiety comprises the formula:

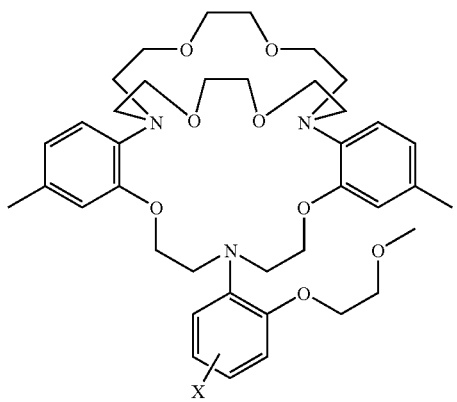

where X represents the position at which the TAC ionophoric moiety is bound in the chromoionophore.

32. The chromoionophore of claim 31, wherein the TAC ionophoric moiety is bound in the chromoionophore in the para position relative to the amine group.

33. The chromoionophore of claim 30, wherein the chromoionophore comprises the formula:

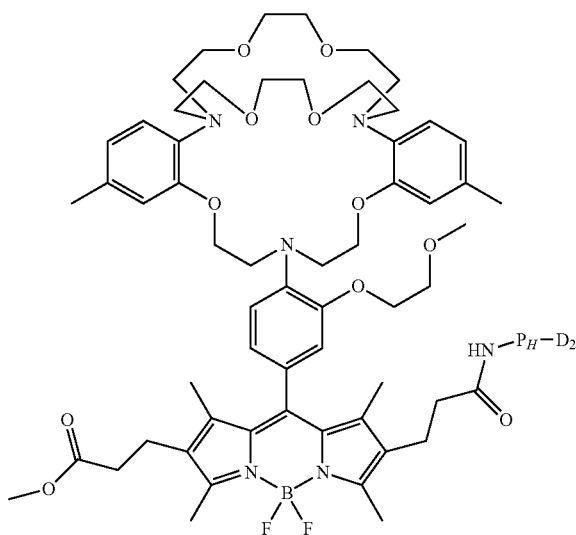

where
$P_H$ is a water soluble polymer; and
$D_2$ is a chromophoric moiety having a emission wavelength different from the chromophoric moiety at position $D_1$.

34. A composition for assessing extracellular potassium ion concentrations, the composition comprising a physiologically compatible solution and a chromoionophore of claim 1.

35. A method for assessing extracellular potassium ion concentrations in vivo, the method comprising:
delivering a chromoionophore according to claim 1 to an extracellular fluid compartment of a subject; and
detecting the presence of absence of a potassium-sensitive detectable signal emitted from the chromoionophore,
wherein intensity of the detectable signal is indicative of the concentration of potassium ions in the compartment.

36. The method of claim 35, wherein said detecting is by imaging through one or more tissues of the subject.

37. The method of claim 35, wherein the method further comprises administering a candidate agent to the subject to assess the effect of the candidate agent upon extracellular potassium concentrations in the extracellular fluid compartment.

38. The method of claim 35, wherein the chromoionophore is contained in a physiologically acceptable solution comprising one or more components of a biological sample of the subject.

39. A method for assessing extracellular potassium ion concentrations in a cell or tissue culture, the method comprising:
contacting a cell or tissue culture with a chromoionophore of claim 1; and
detecting the presence or absence of a potassium-sensitive detectable signal emitted from the chromoionophore;
wherein intensity of the detectable signal is indicative of the extracellular concentration of potassium ions in the culture.

40. The method of claim 39, wherein the method further comprises contacting the cell or tissue culture with a candidate agent to assess the effect of the candidate agent upon extracellular potassium concentrations.

41. A kit for the assessing extracellular potassium ion concentrations, the kit comprising a chromoionophore of claim 1 in a container.

42. A composition for assessing extracellular potassium ion concentrations, the composition comprising a physiologically compatible solution and a chromoionophore of claim 13.

43. A method for assessing extracellular potassium ion concentrations in vivo, the method comprising:
delivering a chromoionophore according to claim 13 to an extracellular fluid compartment of a subject; and
detecting the presence or absence of a potassium-sensitive detectable signal emitted from the chromoionophore,
wherein intensity of the detectable signal is indicative of the concentration of potassium ions in the compartment.

44. The method of claim 43, wherein said detecting is by imaging through one or more tissues of the subject.

45. The method of claim 43, wherein the method further comprises administering a candidate agent to the subject to assess the effect of the candidate agent upon extracellular potassium concentrations in the extracellular fluid compartment.

46. The method of claim 43, wherein the chromoionophore is contained in a physiologically acceptable solution comprising one or more components of a biological sample of the subject.

47. A method for assessing extracellular potassium ion concentrations in a cell or tissue culture, the method comprising:
contacting a cell or tissue culture with a chromoionophore of claim 13; and
detecting the presence of absence of a potassium-sensitive detectable signal emitted from the chromoionophore;
wherein intensity of the detectable signal is indicative of the extracellular concentration of potassium ions in the culture.

48. The method of claim 47, wherein the method further comprises contacting the cell or tissue culture with a candidate agent to assess the effect of the candidate agent upon extracellular potassium concentrations.

49. A kit for the assessing extracellular potassium ion concentrations, the kit comprising a chromoionophore of claim 13 in a container.

50. A hydrophilic potassium-sensitive chromoionophore, wherein the chromoionophore comprises the formula:

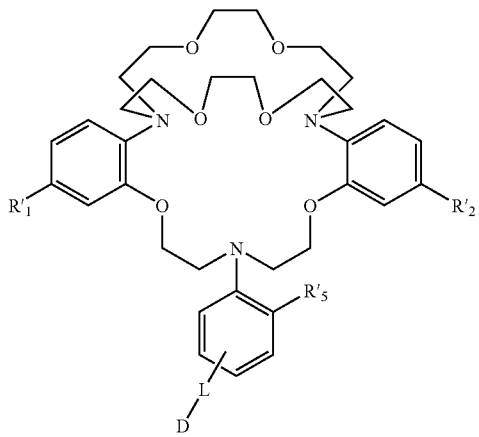

where:
$R'_1$ and $R'_2$ are independently selected from a lower alkyl;
L is a linker selected from a substituted or unsubstituted lower alkyl of the formula —$(CH_2)_v$— or —$(CH_2)_w$—NH—, where v is 0, 1, or 2 and w is 1 or 2;
$R'_5$ is a substituted or unsubstituted alkyl, alkoxy, alkoxyalkoxy, alkoxyaryl, t-alkyl ester of carboxyalkoxy, t-alkyl ester of carboxyalkoxyalkoxy, succinimidylester of carboxyalkoxy, succinimidylester of carboxyalkoxyalkoxy, aminoalkoxy, aminoalkoxyalkoxy, mercaptoalkoxy, or mercaptoalkoxyalkoxy; and
D is a chromophore moiety, and
wherein a water-soluble polymer is covalently bound to D, and wherein the water-soluble polymer is dextran.

51. The chromoionophore of claim 50, wherein $R'_5$ is of the formula:

—[OCH$_2$CH$_2$]$_n$OCH$_3$;

—[OCH$_2$CH$_2$]$_n$O—(CH$_2$)$_m$—COO-t-butyl;

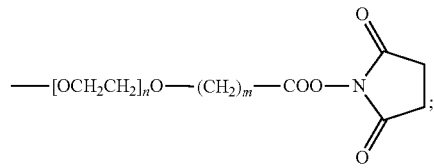

—[OCH$_2$CH$_2$]$_n$O—(CH$_2$)$_m$—NH$_2$; or

—[OCH$_2$CH$_2$]$_n$O—(CH$_2$)$_m$—SH;

n is 0 or 1; and m is an integer from 1 to 6.

52. The chromoionophore of claim 50, wherein:
$R'_1$ and $R'_2$ are each methyl;
$R'_5$ is —(OCH$_2$CH$_2$)OCH$_3$; and
D is in the para position.

53. The chromoionophore of claim 50, wherein D is bound to the dextran through an amide linkage.

54. The chromoionophore of claim 50, wherein the chromoionophore is TAC-Lime-dextran.

* * * * *